US012672928B2

(12) United States Patent
Cohen et al.

(10) Patent No.: US 12,672,928 B2
(45) Date of Patent: Jul. 7, 2026

(54) MODULAR DEVICE COMPRISING MECHANICAL ARMS

(71) Applicant: Momentis Surgical Ltd, Or-Yehuda (IL)

(72) Inventors: Dvir Cohen, Or-Yehuda (IL); Yaron Levinson, Or-Yehuda (IL)

(73) Assignee: MOMENTIS SURGICAL LTD., Or Yehuda (IL)

( * ) Notice: Subject to any disclaimer, the term of this patent is extended or adjusted under 35 U.S.C. 154(b) by 0 days.

(21) Appl. No.: 18/373,352

(22) Filed: Sep. 27, 2023

(65) Prior Publication Data

US 2024/0016564 A1    Jan. 18, 2024

Related U.S. Application Data

(63) Continuation of application No. 16/841,848, filed on Apr. 7, 2020, now Pat. No. 11,771,511, which is a
(Continued)

(51) Int. Cl.
*A61B 34/00*        (2016.01)
*A61B 17/00*        (2006.01)
(Continued)

(52) U.S. Cl.
CPC ........ *A61B 34/70* (2016.02); *A61B 17/00234* (2013.01); *A61B 17/28* (2013.01);
(Continued)

(58) Field of Classification Search
CPC ........... A61B 2017/00477; A61B 2017/00991; A61B 2017/2906; A61B 2034/302;
(Continued)

(56) References Cited

U.S. PATENT DOCUMENTS

| | | | |
|---|---|---|---|
| 2,165,478 A | 7/1939 | Gross | |
| 3,913,573 A | 10/1975 | Gutnick | |

(Continued)

FOREIGN PATENT DOCUMENTS

| | | |
|---|---|---|
| CN | 101040773 | 9/2007 |
| CN | 102465957 | 5/2012 |

(Continued)

OTHER PUBLICATIONS

Requisition by the Examiner Dated Oct. 3, 2023 From the Innovation, Science and Economic Development Canada, Canadian Intellectual Property Office Re. Application No. 2,957,362. (4 Pages).
(Continued)

*Primary Examiner* — Scott Luan
(74) *Attorney, Agent, or Firm* — S.J. INTELLECTUAL PROPERTY LTD.

(57)        ABSTRACT

A method of constructing a system comprising one or more surgical arms, comprising: providing: a plurality of modular units, each modular unit comprising at least one surgical arm attached to at least one motor unit configured for actuating movement of the surgical arm; coupling one or more modular units to each other in an attachment configuration; displaying on a user interface one or both of an indication of the attachment configuration and a selection of an attachment configuration.

11 Claims, 44 Drawing Sheets

Related U.S. Application Data continuation of application No. 15/454,116, filed on Mar. 9, 2017, now Pat. No. 10,617,481, which is a continuation-in-part of application No. 15/501,862, filed as application No. PCT/IL2016/050976 on Sep. 4, 2016, now abandoned.

(60) Provisional application No. 62/305,613, filed on Mar. 9, 2016, provisional application No. 62/305,631, filed on Mar. 9, 2016.

(51) Int. Cl.

| | | |
|---|---|---|
| *A61B 17/28* | (2006.01) | |
| *A61B 34/30* | (2016.01) | |
| *A61B 90/00* | (2016.01) | |
| *A61B 90/50* | (2016.01) | |
| *A61B 17/29* | (2006.01) | |
| *A61B 90/57* | (2016.01) | |

(52) U.S. Cl.

CPC .............. *A61B 34/30* (2016.02); *A61B 34/72* (2016.02); *A61B 34/74* (2016.02); *A61B 90/361* (2016.02); *A61B 90/50* (2016.02); *A61B 2017/00216* (2013.01); *A61B 2017/003* (2013.01); *A61B 2017/00314* (2013.01); *A61B 2017/00353* (2013.01); *A61B 2017/00398* (2013.01); *A61B 2017/00477* (2013.01); *A61B 2017/00991* (2013.01); *A61B 2017/2906* (2013.01); *A61B 2034/302* (2016.02); *A61B 2090/0808* (2016.02); *A61B 2090/571* (2016.02)

(58) Field of Classification Search

CPC ...... A61B 2090/0808; A61B 2090/571; A61B 34/30; A61B 34/70; A61B 34/72; A61B 34/74; A61B 90/361; A61B 90/50

See application file for complete search history.

(56) References Cited

U.S. PATENT DOCUMENTS

| | | | |
|---|---|---|---|
| 4,054,131 | A | 10/1977 | Kessel |
| 4,364,535 | A | 12/1982 | Itoh et al. |
| 4,954,952 | A | 9/1990 | Ubhayakar et al. |
| 5,184,601 | A | 2/1993 | Putman |
| 5,597,146 | A | 1/1997 | Putman |
| 5,624,398 | A | 4/1997 | Smith et al. |
| 5,749,828 | A | 5/1998 | Solomon et al. |
| 5,810,716 | A | 9/1998 | Mukherjee et al. |
| 5,876,325 | A | 3/1999 | Mizuno et al. |
| 6,168,611 | B1 | 1/2001 | Rizvi |
| 6,231,565 | B1 | 5/2001 | Tovey et al. |
| 6,331,181 | B1 | 12/2001 | Tierney et al. |
| 6,425,865 | B1 | 7/2002 | Salcudean et al. |
| 7,008,362 | B2 | 3/2006 | Fitzgibbon |
| 7,371,210 | B2 | 5/2008 | Brock et al. |
| 7,678,117 | B2 | 3/2010 | Hinman et al. |
| 7,766,821 | B2 | 8/2010 | Brunnen et al. |
| 7,833,156 | B2 | 11/2010 | Williams et al. |
| 7,918,845 | B2 | 4/2011 | Saadat et al. |
| 8,114,050 | B2 | 2/2012 | Kaal et al. |
| 8,224,485 | B2 | 7/2012 | Unsworth |
| 8,347,754 | B1 | 1/2013 | Veltri et al. |
| 8,518,024 | B2 | 8/2013 | Williams et al. |
| 8,543,240 | B2 | 9/2013 | Itkowitz et al. |
| 8,562,610 | B2 | 10/2013 | Chabansky et al. |
| 9,010,214 | B2 | 4/2015 | Markvicka et al. |
| 9,033,998 | B1 | 5/2015 | Schaible et al. |
| 9,662,176 | B2 | 5/2017 | Cooper et al. |
| 9,895,200 | B2 | 2/2018 | Yeung et al. |
| 10,092,344 | B2 | 10/2018 | Mohr et al. |
| 10,278,683 | B2 | 5/2019 | Robert et al. |
| 10,299,866 | B2 | 5/2019 | Cohen et al. |
| 10,463,438 | B2 | 11/2019 | Cohen et al. |
| 10,470,831 | B2 | 11/2019 | Cohen et al. |
| 10,646,291 | B2 | 5/2020 | Turner |
| 10,667,877 | B2 | 6/2020 | Kapadia |
| 11,406,464 | B2 | 8/2022 | Peine |
| 11,850,093 | B2 | 12/2023 | Williams et al. |
| 2001/0021854 | A1 | 9/2001 | Donnez et al. |
| 2002/0087048 | A1 | 7/2002 | Brock et al. |
| 2003/0004610 | A1 | 1/2003 | Niemeyer et al. |
| 2003/0013949 | A1 | 1/2003 | Moll et al. |
| 2003/0060927 | A1 | 3/2003 | Gerbi et al. |
| 2003/0109780 | A1 | 6/2003 | Coste-Maniere et al. |
| 2003/0109857 | A1 | 6/2003 | Sanchez et al. |
| 2003/0109957 | A1 | 6/2003 | Sanchez et al. |
| 2004/0044350 | A1 | 3/2004 | Martin et al. |
| 2004/0128026 | A1 | 7/2004 | Harris et al. |
| 2004/0138525 | A1 | 7/2004 | Saadat et al. |
| 2004/0199052 | A1 | 10/2004 | Banik et al. |
| 2004/0236316 | A1 | 11/2004 | Danitz et al. |
| 2005/0059960 | A1 | 3/2005 | Simaan et al. |
| 2005/0096694 | A1 | 5/2005 | Lee |
| 2005/0272977 | A1 | 12/2005 | Saadat et al. |
| 2006/0095022 | A1 | 5/2006 | Moll et al. |
| 2006/0142657 | A1 | 6/2006 | Quaid et al. |
| 2006/0206101 | A1 | 9/2006 | Lee |
| 2006/0241414 | A1 | 10/2006 | Nowlin et al. |
| 2007/0156019 | A1 | 7/2007 | Larkin et al. |
| 2007/0216131 | A1 | 9/2007 | Potappel |
| 2007/0221700 | A1 | 9/2007 | Ortiz et al. |
| 2007/0287992 | A1 | 12/2007 | Diolaiti et al. |
| 2008/0033597 | A1 | 2/2008 | Kraft |
| 2008/0045857 | A1 | 2/2008 | Miller et al. |
| 2008/0064921 | A1 | 3/2008 | Larkin et al. |
| 2008/0065108 | A1 | 3/2008 | Diolaiti |
| 2008/0119868 | A1 | 5/2008 | Sharp et al. |
| 2008/0125869 | A1 | 5/2008 | Paz et al. |
| 2009/0000626 | A1 | 1/2009 | Quaid et al. |
| 2009/0012531 | A1 | 1/2009 | Quaid et al. |
| 2009/0054733 | A1 | 2/2009 | Marescaux et al. |
| 2009/0099554 | A1 | 4/2009 | Forster et al. |
| 2009/0171373 | A1 | 7/2009 | Farritor et al. |
| 2010/0016659 | A1 | 1/2010 | Weitzner |
| 2010/0022837 | A1 | 1/2010 | Ishiguro et al. |
| 2010/0170361 | A1 | 7/2010 | Bennett et al. |
| 2010/0191278 | A1 | 7/2010 | Lee et al. |
| 2010/0225209 | A1 | 9/2010 | Goldberg et al. |
| 2010/0274087 | A1 | 10/2010 | Diolaiti et al. |
| 2010/0292558 | A1 | 11/2010 | Saadat et al. |
| 2010/0318100 | A1 | 12/2010 | Okamoto et al. |
| 2011/0015650 | A1 | 1/2011 | Choi et al. |
| 2011/0022052 | A1 | 1/2011 | Jorgensen |
| 2011/0046441 | A1 | 2/2011 | Wiltshire et al. |
| 2011/0066156 | A1 | 3/2011 | McGahan et al. |
| 2011/0082462 | A1 | 4/2011 | Suarez et al. |
| 2011/0082468 | A1 | 4/2011 | Hagag et al. |
| 2011/0105843 | A1 | 5/2011 | Mueller |
| 2011/0106141 | A1 | 5/2011 | Nakamura |
| 2011/0118748 | A1 | 5/2011 | Itkowitz |
| 2011/0130718 | A1 | 6/2011 | Kidd et al. |
| 2011/0144656 | A1 | 6/2011 | Lee et al. |
| 2011/0238079 | A1 | 9/2011 | Hannaford et al. |
| 2011/0264136 | A1 | 10/2011 | Choi et al. |
| 2011/0276038 | A1 | 11/2011 | Mcintyre et al. |
| 2011/0277775 | A1 | 11/2011 | Holop et al. |
| 2011/0282356 | A1 | 11/2011 | Solomon et al. |
| 2011/0296353 | A1 | 12/2011 | Ahmed et al. |
| 2012/0010629 | A1 | 1/2012 | Mire et al. |
| 2012/0059391 | A1 | 3/2012 | Diolaiti |
| 2012/0059392 | A1 | 3/2012 | Diolaiti |
| 2012/0071891 | A1 | 3/2012 | Itkowitz et al. |
| 2012/0123207 | A1 | 5/2012 | Vargas |
| 2012/0143211 | A1 | 6/2012 | Kishi |
| 2012/0253131 | A1 | 10/2012 | Malkowski et al. |
| 2012/0265007 | A1 | 10/2012 | Moriyama et al. |
| 2013/0006267 | A1 | 1/2013 | Odermatt et al. |
| 2013/0018303 | A1 | 1/2013 | Webster et al. |
| 2013/0030428 | A1 | 1/2013 | Worrell et al. |
| 2013/0035697 | A1 | 2/2013 | Ogawa et al. |

(56) References Cited

U.S. PATENT DOCUMENTS

| | | | |
|---|---|---|---|
| 2013/0060239 A1 | 3/2013 | Hinman et al. | |
| 2013/0172904 A1 | 7/2013 | Ikits | |
| 2013/0178867 A1* | 7/2013 | Farritor | H04L 41/0631 |
| | | | 606/130 |
| 2013/0296882 A1 | 11/2013 | Kim et al. | |
| 2013/0345717 A1 | 12/2013 | Markvicka et al. | |
| 2014/0039517 A1 | 2/2014 | Bowling et al. | |
| 2014/0046340 A1* | 2/2014 | Wilson | A61B 34/30 |
| | | | 606/130 |
| 2014/0052061 A1 | 2/2014 | Weisshaupt et al. | |
| 2014/0062113 A1 | 3/2014 | Kovarik et al. | |
| 2014/0114293 A1 | 4/2014 | Jeong et al. | |
| 2014/0222198 A1 | 8/2014 | Emami et al. | |
| 2014/0243849 A1 | 8/2014 | Saglam et al. | |
| 2014/0276943 A1 | 9/2014 | Bowling et al. | |
| 2014/0316432 A1 | 10/2014 | Malkowski | |
| 2014/0330432 A1 | 11/2014 | Simaan et al. | |
| 2015/0012134 A1 | 1/2015 | Robinson et al. | |
| 2015/0038981 A1 | 2/2015 | Kilroy et al. | |
| 2015/0230697 A1 | 8/2015 | Phee et al. | |
| 2015/0293596 A1 | 10/2015 | Krausen et al. | |
| 2016/0045271 A1 | 2/2016 | McGrogan et al. | |
| 2016/0081714 A1 | 3/2016 | Kobayashi et al. | |
| 2016/0128790 A1 | 5/2016 | Ogawa et al. | |
| 2016/0135909 A1 | 5/2016 | Ogawa et al. | |
| 2016/0135911 A1 | 5/2016 | Yanagihara et al. | |
| 2016/0144504 A1 | 5/2016 | Kuth et al. | |
| 2016/0166343 A1 | 6/2016 | Poon et al. | |
| 2017/0071587 A1 | 3/2017 | Harshman et al. | |
| 2017/0071687 A1 | 3/2017 | Cohen et al. | |
| 2017/0071688 A1 | 3/2017 | Cohen et al. | |
| 2017/0095236 A1 | 4/2017 | Sharma et al. | |
| 2017/0095299 A1 | 4/2017 | Hendrick et al. | |
| 2017/0112581 A1 | 4/2017 | Cohen et al. | |
| 2017/0112583 A1 | 4/2017 | Cohen et al. | |
| 2017/0119483 A1 | 5/2017 | Cohen et al. | |
| 2017/0135771 A1 | 5/2017 | Auld et al. | |
| 2017/0135776 A1 | 5/2017 | Cohen et al. | |
| 2017/0156808 A1 | 6/2017 | Auld | |
| 2017/0165002 A1 | 6/2017 | Sharma et al. | |
| 2017/0189126 A1 | 7/2017 | Weir | |
| 2017/0231701 A1 | 8/2017 | Cohen et al. | |
| 2017/0239005 A1 | 8/2017 | Cohen et al. | |
| 2017/0258538 A1 | 9/2017 | Cohen et al. | |
| 2017/0258539 A1 | 9/2017 | Cohen et al. | |
| 2017/0273702 A1 | 9/2017 | Dewaele et al. | |
| 2017/0274533 A1 | 9/2017 | Berghofer et al. | |
| 2017/0296170 A1 | 10/2017 | Shelton, IV et al. | |
| 2017/0340399 A1 | 11/2017 | Ogawa | |
| 2018/0078034 A1 | 3/2018 | Savall et al. | |
| 2018/0235719 A1 | 8/2018 | Jarc | |
| 2018/0256235 A1 | 9/2018 | Cohen et al. | |
| 2018/0256241 A1 | 9/2018 | Cohen et al. | |
| 2018/0256265 A1 | 9/2018 | Cohen et al. | |
| 2018/0256266 A1 | 9/2018 | Cohen et al. | |
| 2018/0256267 A1 | 9/2018 | Cohen et al. | |
| 2018/0256268 A1 | 9/2018 | Cohen et al. | |
| 2019/0000574 A1 | 1/2019 | Dvir et al. | |
| 2019/0167363 A1 | 6/2019 | Cohen et al. | |
| 2019/0167364 A1 | 6/2019 | Cohen et al. | |
| 2019/0231445 A1 | 8/2019 | Cohen et al. | |
| 2019/0357918 A1 | 11/2019 | Otto et al. | |
| 2020/0170736 A1 | 6/2020 | Cohen et al. | |
| 2020/0289225 A1 | 9/2020 | Cohen et al. | |
| 2021/0196407 A1 | 7/2021 | Cohen et al. | |
| 2021/0338345 A1 | 11/2021 | Cohen et al. | |
| 2022/0054205 A1 | 2/2022 | Cohen et al. | |
| 2023/0052027 A1 | 2/2023 | Cohen et al. | |

FOREIGN PATENT DOCUMENTS

| | | |
|---|---|---|
| CN | 102596062 | 7/2012 |
| CN | 103120596 | 5/2013 |
| DE | 10122316 | 11/2002 |
| EP | 2550926 | 9/2017 |
| JP | 2006-516910 | 7/2006 |
| JP | 2007-509698 | 4/2007 |
| JP | 2008-501477 | 1/2008 |
| JP | 2008-132352 | 6/2008 |
| JP | 2009-136684 | 6/2009 |
| JP | 2010-099530 | 5/2010 |
| JP | 2011-004880 | 1/2011 |
| JP | 2011-172766 | 9/2011 |
| JP | 2011-528576 | 11/2011 |
| JP | 2012-525916 | 10/2012 |
| JP | 2013-126464 | 6/2013 |
| JP | 2014-000265 | 1/2014 |
| JP | 2014-516657 | 7/2014 |
| JP | 5744455 | 7/2015 |
| JP | 2019-187994 | 10/2019 |
| WO | WO 88/04544 | 6/1988 |
| WO | WO 2010/096580 | 8/2010 |
| WO | WO 2013/116869 | 8/2013 |
| WO | WO 2015/019675 | 2/2015 |
| WO | WO 2015/023793 | 2/2015 |
| WO | WO 2016/035084 | 3/2016 |
| WO | WO 2016/035086 | 3/2016 |
| WO | WO 2016/035085 | 8/2016 |
| WO | WO 2017/037723 | 3/2017 |
| WO | WO 2021/111394 | 6/2021 |
| WO | WO 2023/286066 | 1/2023 |

OTHER PUBLICATIONS

Advisory Action Before the Filing of An Appeal Brief Dated Feb. 13, 2019 From the US Patent and Trademark Office Re. U.S. Appl. No. 15/454,116. (4 pages).

Advisory Action Before the Filing of an Appeal Brief Dated Jul. 13, 2018 From the US Patent and Trademark Office Re. U.S. Appl. No. 15/454,123. (3 pages).

Advisory Action Before the Filing of An Appeal Brief Dated May 21, 2019 From the US Patent and Trademark Office Re. U.S. Appl. No. 15/312,732. (23 pages).

Advisory Action Before the Filing of An Appeal Brief Dated Jan. 24, 2019 From the US Patent and Trademark Office Re. U.S. Appl. No. 15/454,116. (5 pages).

Advisory Action Dated Sep. 10, 2021 From the US Patent and Trademark Office Re. U.S. Appl. No. 15/358,331. (6 Pages).

Applicant-Initiated Interview Summary Dated Oct. 2, 2017 From the US Patent and Trademark Office Re. U.S. Appl. No. 15/358,331. (3 pages).

Applicant-Initiated Interview Summary Dated Oct. 6, 2017 From the US Patent and Trademark Office Re. U.S. Appl. No. 15/454,123. (2 pages).

Applicant-Initiated Interview Summary Dated Mar. 7, 2018 From the US Patent and Trademark Office Re. U.S. Appl. No. 15/312,732. (3 pages).

Applicant-Initiated Interview Summary Dated Jul. 19, 2017 From the US Patent and Trademark Office Re. U.S. Appl. No. 15/418,891. (3 pages).

Applicant-Initiated Interview Summary Dated Nov. 22, 2019 From the US Patent and Trademark Office Re. U.S. Appl. No. 15/501,862. (3 pages).

Applicant-Initiated Interview Summary Dated Apr. 24, 2019 From the US Patent and Trademark Office Re. U.S. Appl. No. 15/358,331. (3 Pages).

Applicant-Initiated Interview Summary Dated Jan. 26, 2018 From the US Patent and Trademark Office Re. U.S. Appl. No. 15/418,891. (3 pages).

Application-Initiated Interview Summary Dated May 31, 2019 From the US Patent and Trademark Office Re. U.S. Appl. No. 16/271,915. (3 Pages).

Communication Pursuant to Article 94(3) EPC Dated Mar. 4, 2019 From the European Patent Office Re. Application No. 15838758.9. (9 Pages).

Communication Pursuant to Article 94(3) EPC Dated Apr. 8, 2019 From the European Patent Office Re. Application No. 15838126.9. (15 Pages).

(56) References Cited

OTHER PUBLICATIONS

Communication Pursuant to Article 94(3) EPC Dated Mar. 11, 2019 From the European Patent Office Re. Application No. 17160061.2. (6 Pages).

Communication Pursuant to Article 94(3) EPC Dated Oct. 13, 2022 From the European Patent Office Re. Application No. 20176879.3. (10 Pages).

Communication Pursuant to Article 94(3) EPC Dated Oct. 26, 2022 From the European Patent Office Re. Application No. 20187025.0. (6 Pages).

Decision of Rejection Dated Apr. 10, 2019 From the State Intellectual Property Office of the People's Republic of China Re. Application No. 201580052098.8. (3 Pages).

European Search Report and the European Search Opinion Dated Nov. 4, 2020 From the European Patent Office Re. Application No. 20187025.0. (10 Pages).

European Search Report and the European Search Opinion Dated Oct. 21, 2020 From the European Patent Office Re. Application No. 20176879.3. (12 Pages).

European Search Report and the European Search Opinion Dated Aug. 22, 2017 From the European Patent Office Re. Application No. 17160061.2. (9 Pages).

Ex Parte Quayle OA Dated Nov. 7, 2018 From the US Patent and Trademark Office Re. U.S. Appl. No. 15/501,862. (8 pages).

Examiner's Answer Dated Sep. 9, 2019 Before The Patent Trial and Appeal Board of the US Patent and Trademark Office Re. U.S. Appl. No. 15/312,732. (12 pages).

Final Official Action Dated Jan. 6, 2023 From the US Patent and Trademark Office Re. U.S. Appl. No. 16/377,280. (31 Pages).

Final Official Action Dated Jun. 9, 2021 From the US Patent and Trademark Office Re. U.S. Appl. No. 15/358,331. (42 Pages).

Final Official Action Dated Oct. 8, 2020 from the US Patent and Trademark Office Re. U.S. Appl. No. 15/916,304. (12 pages).

International Preliminary Report on Patentability Dated Mar. 15, 2018 From the International Bureau of WIPO Re. Application No. PCT/IL2015/050892. (9 Pages).

International Preliminary Report on Patentability Dated Mar. 16, 2017 From the International Bureau of WIPO Re. Application No. PCT/IL2015/050891. (16 Pages).

International Preliminary Report on Patentability Dated Mar. 16, 2017 From the International Bureau of WIPO Re. Application No. PCT/IL2015/050892. (7 Pages).

International Preliminary Report on Patentability Dated Mar. 16, 2017 From the International Bureau of WIPO Re. Application No. PCT/IL2015/050893. (11 Pages).

International Search Report and the Written Opinion Dated Dec. 6, 2016 From the International Searching Authority Re. Application No. PCT/IL2015/050892. (36 Pages).

International Search Report and the Written Opinion Dated Mar. 10, 2016 From the International Searching Authority Re. Application No. PCT/IL2015/050893. (20 Pages).

International Search Report and the Written Opinion Dated Mar. 11, 2016 From the International Searching Authority Re. Application No. PCT/IL2015/050892. (14 Pages).

International Search Report and the Written Opinion Dated Feb. 26, 2016 From the International Searching Authority Re. Application No. PCT/IL2015/050891. (26 Pages).

International Search Report and the Written Opinion Dated Nov. 27, 2022 From the International Searching Authority Re. Application No. PCT/IL2022/050763 (22 Pages).

Interview Summary Dated Aug. 11, 2020 from the US Patent and Trademark Office Re. U.S. Appl. No. 15/358,331. (3 pages).

Interview Summary Dated Jan. 20, 2022 from US Patent and Trademark Office Re. U.S. Appl. No. 15/358,331. (2 pages).

Invitation to Pay Additional Fees Dated Dec. 3, 2015 From the International Searching Authority Re. Application No. PCT/IL2015/050891. (2 Pages).

Invitation to Pay Additional Fees Dated Jan. 12, 2016 From the International Searching Authority Re. Application No. PCT/IL2015/050893. (3 Pages).

Notice Of Allowance Dated Jul. 3, 2019 From the US Patent and Trademark Office Re. U.S. Appl. No. 16/271,922. (26 pages).

Notice of Allowance Dated May 12, 2023 from the US Patent and Trademark Office Re. U.S. Appl. No. 16/841,848. (24 pages).

Notice Of Allowance Dated Jun. 15, 2022 From the US Patent and Trademark Office Re. U.S. Appl. No. 15/358,331. (23 pages).

Notice of Allowance Dated May 17, 2021 From the US Patent and Trademark Office Re. U.S. Appl. No. 16/121,704. (9 Pages).

Notice of Allowance Dated Nov. 19, 2020 from the US Patent and Trademark Office Re. U.S. Appl. No. 15/916,304. (4 pages).

Notice Of Allowance Dated Nov. 21, 2019 From the US Patent and Trademark Office Re. U.S. Appl. No. 15/454,116. (36 pages).

Notice of Allowance Dated Aug. 23, 2023 from the US Patent and Trademark Office Re. U.S. Appl. No. 16/672,579. (38 pages).

Notice Of Allowance Dated Jul. 25, 2019 From the US Patent and Trademark Office Re. U.S. Appl. No. 16/271,915. (27 Pages).

Notice Of Allowance Dated Jun. 26, 2019 From the US Patent and Trademark Office Re. U.S. Appl. No. 15/454,123. (24 Pages).

Notice of Allowance Dated May 26, 2023 From the US Patent and Trademark Office Re. U.S. Appl. No. 15/916,302. (17 Pages).

Notice Of Allowance Dated Jan. 28, 2019 From the US Patent and Trademark Office Re. U.S. Appl. No. 15/924,635. (15 pages).

Notice of Allowance Dated Nov. 3, 2022 from the US Patent and Trademark Office Re. U.S. Appl. No. 15/916,302. (19 pages).

Notice of Allowance Dated Mar. 31, 2021 From the US Patent and Trademark Office Re. U.S. Appl. No. 15/924,546. (18 Pages).

Notice of Reason for Rejection Dated Dec. 15, 2020 From the Japan Patent Office Re. Application No. 2019-215144 and Its Translation Into English. (16 Pages).

Notice of Reason(s) for Rejection Dated Mar. 7, 2023 From the Japan Patent Office Re. Application No. 2021-117181 and Its Translation Into English. (7 Pages).

Notice of Reasons for Rejection Dated Jul. 2, 2019 From the Japan Patent Office Re. Application No. 2017-532229 and Its Translation Into English. (11 Pages).

Notice of Reasons for Rejection Dated Jul. 26, 2022 From the Japan Patent Office Re. Application No. 2021-117181 and Its Translation Into English. (14 Pages).

Notification of Office Action and Search Report Dated Dec. 2, 2019 From the State Intellectual Property Office of the People's Republic of China Re. Application No. 201580052098.8 and Its Summary in English. (7 Pages).

Notification of Office Action and Search Report Dated Jan. 15, 2021 From the State Intellectual Property Office of the People's Republic of China Re. Application No. 202011456521.X and Its English Summery. (5 Pages).

Notification of Office Action and Search Report Dated Jul. 20, 2020 From the State Intellectual Property Office of the People's Republic of China Re. Application No. 201580052098.8 and Its Translation of Office Action Into English. (6 Pages).

Notification of Office Action and Search Report Dated Sep. 25, 2023 From the National Intellectual Property Administration of the People's Republic of China Re. Application No. 202011456521.X and Its Translation Into English. (14 Pages).

Notification of Office Action Dated Sep. 3, 2018 From the State Intellectual Property Office of the People's Republic of China Re. Application No. 201580052098.8. (4 Pages).

Notification of Office Action Dated Jan. 19, 2018 From the State Intellectual Property Office of the People's Republic of China Re. Application No. 201580052098.8. (4 Pages).

Office Action Dated Aug. 20, 2023 From the Israel Patent Office Re. Application No. 302177. (5 Pages).

Office Action Dated Dec. 23, 2021 From the Israel Patent Office Re. Application No. 283641 and Its Translation Into English. (6 Pages).

Office Action Dated Apr. 28, 2020 From the Israel Patent Office Re. Application No. 250896 and Its Translation Into English. (4 Pages).

Official Action Dated May 3, 2023 from the US Patent and Trademark Office Re. U.S. Appl. No. 17/976,954. (44 pages).

Official Action Dated Apr. 4, 2019 From the US Patent and Trademark Office Re. U.S. Appl. No. 16/271,915. (12 Pages).

Official Action Dated Dec. 4, 2017 From the US Patent and Trademark Office Re. U.S. Appl. No. 15/358,325. (20 pages).

(56) References Cited

OTHER PUBLICATIONS

Official Action Dated Feb. 4, 2021 From the US Patent and Trademark Office Re. U.S. Appl. No. 16/121,704. (74 Pages).
Official Action Dated Oct. 4, 2022 from US Patent and Trademark Office Re. U.S. Appl. No. 16/672,579. (86 pages).
Official Action Dated Jul. 5, 2019 From the US Patent and Trademark Office Re. U.S. Appl. No. 15/501,862. (7 Pages).
Official Action Dated Jun. 5, 2017 From the US Patent and Trademark Office Re. U.S. Appl. No. 15/418,891. (28 pages).
Official Action Dated Jul. 6, 2023 from the US Patent and Trademark Office Re. U.S. Appl. No. 17/468,745. (87 pages).
Official Action Dated Aug. 7, 2017 From the US Patent and Trademark Office Re. U.S. Appl. No. 15/358,325. (25 pages).
Official Action Dated Aug. 7, 2019 From the US Patent and Trademark Office Re. U.S. Appl. No. 15/358,331. (46 Pages).
Official Action Dated Jul. 7, 2022 from US Patent and Trademark Office Re. U.S. Appl. No. 16/377,280. (110 pages).
Official Action Dated Jan. 9, 2019 From the US Patent and Trademark Office Re. U.S. Appl. No. 15/358,331. (40 pages).
Official Action Dated Mar. 9, 2017 From the US Patent and Trademark Office Re. U.S. Appl. No. 15/401,045. (23 pages).
Official Action Dated Jul. 10, 2017 From the US Patent and Trademark Office Re. U.S. Appl. No. 15/358,331. (32 pages).
Official Action Dated Mar. 10, 2017 From the US Patent and Trademark Office Re. U.S. Appl. No. 15/402,342. (25 pages).
Official Action Dated Jul. 11, 2023 from the US Patent and Trademark Office Re. U.S. Appl. No. 16/377,280. (24 pages).
Official Action Dated Dec. 13, 2017 From the US Patent and Trademark Office Re. U.S. Appl. No. 15/402,257. (44 pages).
Official Action Dated Jan. 13, 2020 From the US Patent and Trademark Office Re. U.S. Appl. No. 15/501,862. (6 pages).
Official Action Dated Dec. 14, 2018 From the US Patent and Trademark Office Re. U.S. Appl. No. 15/454,116. (27 pages).
Official Action Dated Nov. 14, 2018 From the US Patent and Trademark Office Re. U.S. Appl. No. 15/312,732. (25 pages).
Official Action Dated Dec. 17, 2020 From the US Patent and Trademark Office Re. U.S. Appl. No. 15/924,546. (78 Pages).
Official Action Dated Jun. 17, 2022 from US Patent and Trademark Office Re. U.S. Appl. No. 15/916,302. (120 pages).
Official Action Dated Feb. 20, 2020 From the US Patent and Trademark Office Re. U.S. Appl. No. 15/358,331. (33 pages).
Official Action Dated Mar. 20, 2018 From the US Patent and Trademark Office Re. U.S. Appl. No. 15/454,123. (36 pages).
Official Action Dated May 21, 2020 from the US Patent and Trademark Office Re. U.S. Appl. No. 15/916,304. (82 pages).
Official Action Dated Mar. 22, 2019 From the US Patent and Trademark Office Re. U.S. Appl. No. 15/454,123. (32 pages).
Official Action Dated Jul. 23, 2018 From the US Patent and Trademark Office Re. U.S. Appl. No. 15/924,635. (20 pages).
Official Action Dated Jan. 26, 2018 From the US Patent and Trademark Office Re. U.S. Appl. No. 15/312,732. (50 pages).
Official Action Dated Nov. 27, 2017 From the US Patent and Trademark Office Re. U.S. Appl. No. 15/418,891. (35 pages).
Official Action Dated Aug. 28, 2017 From the US Patent and Trademark Office Re. U.S. Appl. No. 15/454,123. (32 pages).
Official Action Dated Feb. 28, 2018 From the US Patent and Trademark Office Re. U.S. Appl. No. 15/358,331. (34 pages).
Official Action Dated Jun. 28, 2018 From the US Patent and Trademark Office Re. U.S. Appl. No. 15/454,116. (67 pages).
Official Action Dated Sep. 28, 2020 from the US Patent and Trademark Office Re. U.S. Appl. No. 15/358,331. (35 pages).
Official Action Dated Jun. 29, 2018 From the US Patent and Trademark Office Re. U.S. Appl. No. 15/312,732. (34 pages).
Official Action Dated Jan. 30, 2019 From the US Patent and Trademark Office Re. U.S. Appl. No. 15/501,862. (6 pages).
Official Action Dated Sep. 30, 2022 from US Patent and Trademark Office Re. U.S. Appl. No. 16/841,848. (83 pages).

Requisition by the Examiner Dated May 4, 2022 From the Innovation, Science and Economic Development Canada, Canadian Intellectual Property Office Re. Application No. 2,957,624 with Claims. (9 Pages).
Requisition by the Examiner Dated Dec. 7, 2022 From the Innovation, Science and Economic Development Canada, Canadian Intellectual Property Office Re. Application No. 2,957,362.(20 pages).
Requisition by the Examiner Dated Sep. 8, 2023 From the Innovation, Science and Economic Development Canada, Canadian Intellectual Property Office Re. Application No. 2,960,354. (7 Pages).
Requisition by the Examiner Dated Oct. 14, 2021 From the Innovation, Science and Economic Development Canada, Canadian Intellectual Property Office Re. Application No. 2,957,622. (37 Pages).
Requisition by the Examiner Dated Oct. 14, 2021 From the Innovation, Science and Economic Development Canada, Canadian Intellectual Property Office Re. Application No. 2,957,624. (22 Pages).
Requisition by the Examiner Dated Apr. 28, 2022 From the Innovation, Science and Economic Development Canada, Canadian Intellectual Property Office Re. Application No. 2,957,622. (3 Pages).
Requisition of the Examiner Dated Oct. 4, 2021 From the Innovation, Science and Economic Development Canada, Canadian Intellectual Property Office Re. Application No. 2,957,620. (7 Pages).
Requisition of the Examiner Dated Apr. 6, 2022 From the Innovation, Science and Economic Development Canada, Canadian Intellectual Property Office Re. Application No. 2,957,620 togethr with Claims. (25 Pages).
Restriction Official Action Dated May 2, 2018 From the US Patent and Trademark Office Re. U.S. Appl. No. 15/501,862. (6 pages).
Restriction Official Action Dated Aug. 7, 2018 From the US Patent and Trademark Office Re. U.S. Appl. No. 15/501,862. (6 pages).
Restriction Official Action Dated Feb. 7, 2018 From the US Patent and Trademark Office Re. U.S. Appl. No. 15/454,116. (6 pages).
Restriction Official Action Dated Oct. 16, 2020 from the US Patent and Trademark Office Re. U.S. Appl. No. 16/121,704. (6 pages).
Restriction Official Action Dated Mar. 17, 2017 From the US Patent and Trademark Office Re. U.S. Appl. No. 15/418,891. (7 pages).
Restriction Official Action Dated Mar. 28, 2022 from US Patent and Trademark Office Re. U.S. Appl. No. 16/672,579. (6 pages).
Restriction Official Action Dated Dec. 30, 2021 from US Patent and Trademark Office Re. U.S. Appl. No. 15/916,302. (5 pages).
Restriction Official Action Dated Dec. 30, 2021 from US Patent and Trademark Office Re. U.S. Appl. No. 16/377,280. (6 pages).
Summons to Attend Oral Proceedings Pursuant to Rule 115(1) EPC and Communication From the Examining Division Dated May 14, 2019 From the European Patent Office Re. Application No. 16840991.0 (5 Pages).
Summons to Attend Oral Proceedings Pursuant to Rule 115(1) EPC Dated Dec. 2, 2019 From the European Patent Office Re. Application No. 15838758.9. (14 Pages).
Summons to Attend Oral Proceedings Pursuant to Rule 115(1) EPC Dated Sep. 16, 2019 From the European Patent Office Re. Application No. 15838758.9. (14 Pages).
Summons to Attend Oral Proceedings Pursuant to Rule 115(1) EPC Dated Nov. 19, 2019 From the European Patent Office Re. Application No. 17160061.2. (6 Pages).
Summons to Attend Oral Proceedings Pursuant to Rule 115(1) EPC Dated Sep. 27, 2019 From the European Patent Office Re. Application No. 17160061.2. (8 Pages).
Supplementary European Search Report and the European Search Opinion Dated Apr. 9, 2018 From the European Patent Office Re. Application No. 15838758.9. (12 Pages).
Supplementary European Search Report and the European Search Opinion Dated Jun. 11, 2018 From the European Patent Office Re. Application No. 15838126.9. (11 Pages).
Supplementary European Search Report and the European Search Opinion Dated Jun. 21, 2018 From the European Patent Office Re. Application No. 16840991.0 (7 Pages).

(56) References Cited

OTHER PUBLICATIONS

Translation Dated Dec. 5, 2019 of Notification of Office Action Dated Dec. 2, 2019 From the State Intellectual Property Office of the People's Republic of China Re. Application No. 201580052098. 8. 4 Pages).

Translation Dated Sep. 13, 2018 of Notification of Office Action Dated Sep. 3, 2018 From the State Intellectual Property Office of the People's Republic of China Re. Application No. 201580052098.8. (3 Pages).

Translation Dated Apr. 22, 2019 of Decision of Rejection Dated Apr. 10, 2019 From the State Intellectual Property Office of the People's Republic of China Re. Application No. 201580052098.8. (4 Pages).

Translation of Notification of Office Action Dated Jan. 19, 2018 From the State Intellectual Property Office of the People's Republic of China Re. Application No. 201580052098.8. (2 Pages).

Box et al. "Rapid Communciation: Robot-Assisted Notes Nephrectomy: Initial Report", Journal of Endourology, 22(3): 503-506, Mar. 2008.

Domingo et al. "Overview of Current Trends in Hysterectomy", Expert Reviews of Obstetrics & Gynaecology, 4(6): 673-685, 2009.

Hubens et al. "What Have We Learnt After Two Years Working With the Da Vinci Robot System in Digestive Surgery?", Acta Chirurgica Belgica, 104(6): 609-614, Nov.-Dec. 2004.

Irvine et al. "Anaesthesia for Robot-Assisted Laporoscopic Surgery", Continuing Education in Anaesthesia, Critical Care & Pain, 9(4): 125-129, Advance Access Published Jun. 25, 2009.

Kho et al. "Vaginal Versus Laparoscopic Hysterectomy. Vaginal Hysterectomy: The Best Minimally Invasive Approach", Contemporary OB/GYNObstetrics & Women's Health, 7 P., Oct. 1, 2013.

Komura et al. "An Inverse Kinematics Method for 3D Figures With Motion Data", Proceedings of the Computer Graphics International, CGI'03, Jul. 9-11, 2003, p. 266-271, Jul. 2003.

Lee "Anesthetic Considerations for Robotic Surgery", Korean Journal of Anesthesiology, 66(1): 3-11, Jan. 2014.

Piccigallo et al. "Design of A Novel Bimanual Robotic System for Single-Port Laparoscopy", IEEE/ASME Transactions on Mechatronics, 15(6): 871-878, Dec. 13, 2010.

Ramos et al. "Human Hybrid Notes Transvaginal Sleeve Gastrectomy: Initial Experience", Surgery for Obesity and Related Diseases, 4: 660-663, 2008.

Teljeur et al. "Economic Evaluation of Robot-Assisted Hysterectomy: A Cost-Minimisation Analysis", BJOG: An International Journal of Obstetrics and Gynaecology, 121(12): 1546-1555, Published Online May 9, 2014.

* cited by examiner

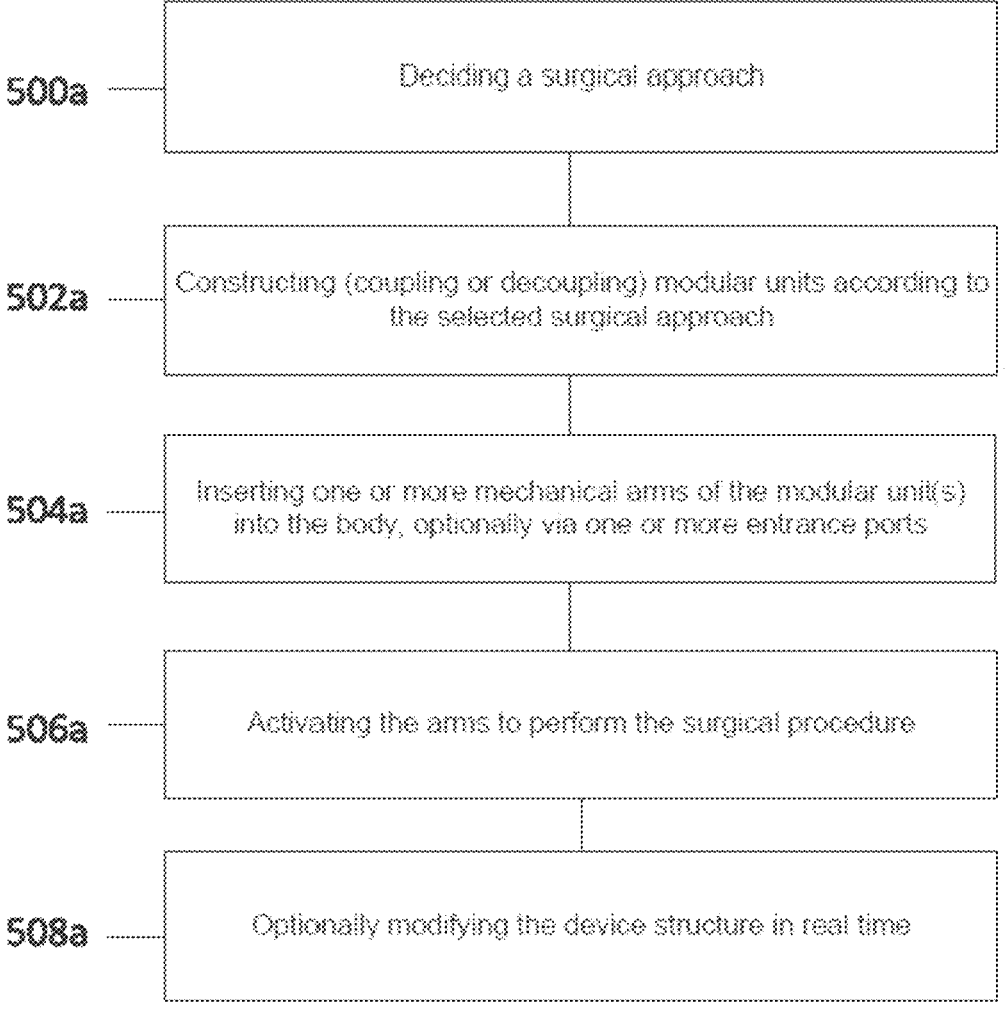

500a — Deciding a surgical approach

502a — Constructing (coupling or decoupling) modular units according to the selected surgical approach 504a — Inserting one or more mechanical arms of the modular unit(s) into the body, optionally via one or more entrance ports 506a — Activating the arms to perform the surgical procedure 508a — Optionally modifying the device structure in real time

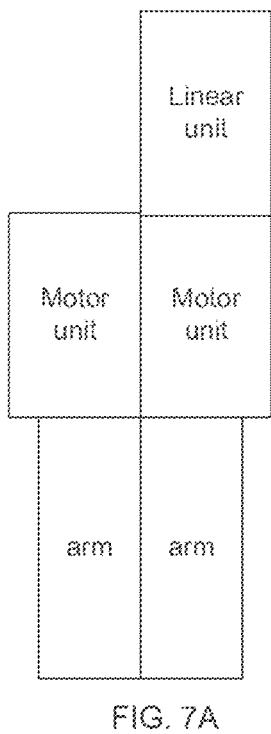
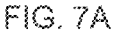
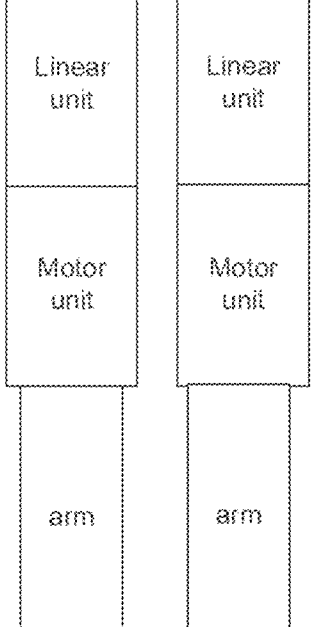
FIG. 7A
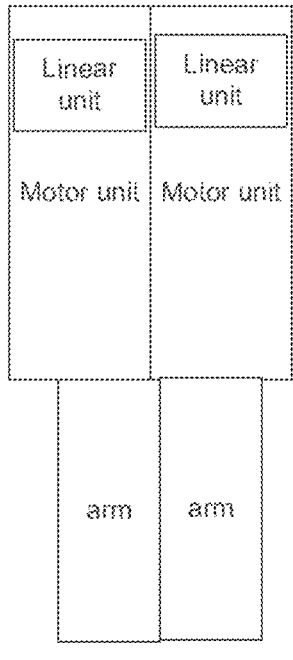
FIG. 7B
FIG. 7C
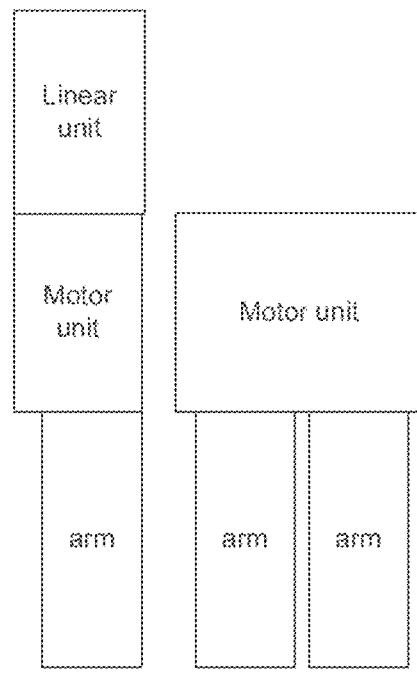
FIG. 7D

1000

1002

1004          1000          1006     1007

α

1402          1412          1400

1402          1414          1400
1406          1404

2102

2104

2202b 2204a-d

X

2204b

2204a

2204d

2204c

3100

3104

3106

3102

3108

3108b

31

3114

3108a

3108

3108b

3112

3108a

3108

3108b

3118

3120

3116

MODULAR DEVICE COMPRISING MECHANICAL ARMS

RELATED APPLICATIONS

This application is a continuation of U.S. patent application Ser. No. 16/841,848, filed on Apr. 7, 2020, which is a continuation of U.S. patent application Ser. No. 15/454,116 filed on Mar. 9, 2017 now U.S. Pat. No. 10,617,481, which claims the benefit of priority under 35 USC § 119(e) of U.S. Provisional Patent Application No. 62/305,631 filed on Mar. 9, 2016, and which also is a Continuation-in-Part (CIP) of U.S. patent application Ser. No. 15/501,862 filed on Feb. 6, 2017, which is a National Phase of PCT Patent Application No. PCT/IL2016/050976 having International Filing Date of Sep. 4, 2016, which claims the benefit of priority under 35 USC § 119(e) of U.S. Provisional Patent Application No. 62/305,613 filed on Mar. 9, 2016.

This application is also related to PCT Patent Application Nos. PCT/IL2015/050891, PCT/IL2015/050892, and PCT/IL2015/050893, all having International Filing Dates of Sep. 4, 2015.

The contents of the above applications are all incorporated by reference as if fully set forth herein in their entirety.

FIELD AND BACKGROUND OF THE INVENTION

The present invention, in some embodiments thereof, relates to actuation of a device including at least one surgical arm and, more particularly, but not exclusively, to a motor unit configured for actuating at least one surgical arm.

Background art includes: "Design of a Compact Robotic Manipulator for Single-Port Laparoscopy" by Claudio Quaglia et al, Paper No: MD-13-1148 in J. Mech. Des. 136(9), 095001 (Jun. 13, 2014); "An inverse kinematics method for 3D FIGs. with motion data" by Taku Komura et al, Proceedings of the Computer Graphics International (CGI' 03);

Hubens et al., 2004, "What Have we Learnt after Two Years Working with the Da Vinci Robot System in Digestive Surgery?", Acta chir belg;

Michael Irvine, 2009, "Anaesthesia for Robot-Assisted Laparoscopic Surgery", Cont Edu Anaesth Crit Care and Pain;

Jeong Rim Lee, 2014, "Anesthetic considerations for robotic surgery", Korean Journal of Anesthesiology;

Teljeur et al., 2014, "Economic evaluation of robot-assisted hysterectomy: a cost-minimisation analysis", BJOG;

Box et al., 2008, "Rapid communication: robot-assisted NOTES nephrectomy: initial report", J Endourol;

DR. Domigo, 2009, "Overview of current hysterectomy trends", Expert Review of Obstetrics & Gynecology; and DR. Kho, "Vaginal versus laparoscopic hysterectomy", Contemporary OB/GYN Expert Advice, 2013.

Additional background art includes U.S. Pat. Nos. 8,224, 485, 8,347,754, 7,833,156, 8,518,024, International Patent Application Publication No. WO 2010096580, and International Patent Application Publication No. WO 2013116869.

SUMMARY OF THE INVENTION

According to an aspect of some embodiments of the present invention there is provided a surgical system comprising:

at least two modular units, the modular units each comprising:

a surgical arm; and a motor unit configured for actuating movement of the surgical arm, the motor unit configured to be operably attached to the surgical arm, where a first face of a motor unit housing generally defines a plane which is at an angle of 60-120° to a long axis of the surgical arm;

wherein the motor unit is configured to be aligned adjacent a motor unit of at least one second modular unit;

wherein a second face of a housing of the motor unit generally defines a plane which is at an angle to the first face and which comprises a connection geometry suitable for connecting the housing of the motor unit to a housing of the motor unit of the second modular unit.

According to some embodiments of the invention, the motor unit is configured to be operably attached to the surgical arm such that the surgical arm extends from the first face of the motor unit housing.

According to some embodiments of the invention, the second face is 60-120° to the first face.

According to some embodiments of the invention, the motor unit housing has an elongated shape, wherein the second face is a longitudinal face of the motor unit housing.

According to some embodiments of the invention, a central long axis of the motor unit is parallel to a central long axis of at least a portion of the surgical arm extending from the motor unit, the motor unit comprising a proximal extension of the surgical arm.

According to some embodiments of the invention, the connection geometry is configured such that when the modular unit is connected to the second modular unit a separation between the second face of the modular unit housing and second face of the second modular unit housing is less than 2 mm.

According to some embodiments of the invention, the connection geometry is configured such that when the modular unit is connected to the second modular unit the second face of the modular unit housing directly contacts a second face of the second modular unit housing.

According to some embodiments of the invention, the modular unit is attached to the second modular unit at the connection geometry, a distance between long axes of the surgical arms adjacent to the motor unit housings is less than 5 mm.

According to some embodiments of the invention, the system includes a plurality of the modular units.

According to some embodiments of the invention, the connection geometry comprises one or both of protrusions and indentations for engaging respective indentations and protrusions of the housing of the motor unit of the second modular unit.

According to some embodiments of the invention, the connection geometry comprises one or both of protrusions and indentations for engaging respective indentations and protrusions of one or more connector.

According to some embodiments of the invention, the protrusions and indentions extend in a substantially perpendicular direction relative to the second face of the housing.

According to some embodiments of the invention, the surgical arm is positioned at a lateral distance smaller than 1 mm from the second face of the housing.

According to some embodiments of the invention, modular units are each configured to operate independently.

According to some embodiments of the invention, the second face is a portion of the motor unit housing where 90-99% of a surface are of a portion of the housing varies by at most 0.1-1 mm from a planar tangent.

According to some embodiments of the invention, at least one of the motor units comprises an integral linear unit, the linear unit configured for actuating at least one of advancement and retraction of the modular unit.

According to some embodiments of the invention, at least one of the motors unit is configured to be coupled to a linear unit, the linear unit configured for actuating at least one of advancement and retraction of the modular unit.

According to some embodiments of the invention, the linear unit comprises:

an elongated rail comprising a proximal end and a distal end;

a sliding element positionable on the rail, the sliding element couplable to the motor unit; the sliding element configured to move proximally and distally on the rail to move the motor unit.

According to some embodiments of the invention, the system comprises a plurality of modular units and wherein a single linear unit is configured to actuate linear movement of the plurality of modular units.

According to some embodiments of the invention, the system comprising two modular units, wherein motor units of the two modular units, attached at the connection geometries and additionally interlocked to each other.

According to some embodiments of the invention, at least a third face of the housing comprises a connection geometry suitable for engaging a face of an additional modular unit.

According to some embodiments of the invention, at least a third longitudinal face of the housing comprises a connection geometry suitable for engaging a face of an additional modular unit.

According to some embodiments of the invention, each longitudinal face of the housing comprises a connection geometry suitable for engaging a longitudinal face of an additional modular unit.

According to some embodiments of the invention, a coupling between the motor units comprises a quick release mechanism comprising a latch configured to release a lock of the motor units.

According to some embodiments of the invention, the motor unit is configured for actuating one or both of rotation and bending of at least a portion of the surgical arm.

According to some embodiments of the invention, the system further comprises a third arm.

According to some embodiments of the invention, the system comprises three modular units, a third modular unit comprising a third motor unit and the third arm.

According to some embodiments of the invention, the third arm carries a camera.

According to some embodiments of the invention, the linear unit comprises a sensor for detecting if the unit is connected to an external device or system.

According to some embodiments of the invention, the modular unit comprises a sensor for detecting if the modular unit is connected to an additional unit or units.

According to an aspect of some embodiments of the present invention there is provided a method of constructing a system comprising one or more surgical arms, comprising:

providing:

a plurality of modular units, each modular unit comprising at least one surgical arm attached to at least one motor unit configured for actuating movement of the surgical arm;

coupling one or more modular units to each other in an attachment configuration;

displaying on a user interface one or both of an indication of the attachment configuration and a selection of an attachment configuration.

According to some embodiments of the invention, the method comprises selecting a surgical approach using the user interface.

According to some embodiments of the invention, the coupling is in accordance with the selected surgical approach.

According to some embodiments of the invention, the coupling is performed during one or both of: set-up of the system prior to the surgery, and during the surgery.

According to some embodiments of the invention, the selecting a surgical approach comprises deciding a number of surgical ports for accessing a patient's body.

According to some embodiments of the invention, the selecting a surgical approach comprises deciding a location on a patient's body for each port for accessing a patient's body.

According to some embodiments of the invention, a number of the modular units is selected in accordance with the number of surgical ports through which the surgery is performed.

According to some embodiments of the invention, a spatial arrangement of modular units is selected in accordance with a number of surgical ports through which the surgery is performed.

According to some embodiments of the invention, a number of surgical arms is selected in accordance with a number of surgical ports through which the surgery is performed.

According to some embodiments of the invention, a port comprises a natural body orifice or an incised opening.

According to some embodiments of the invention, the natural body orifice is a vagina.

According to some embodiments of the invention, the method comprises introducing one or more surgical arms through the ports.

According to some embodiments of the invention, the method comprises introducing two surgical arms through the ports.

According to some embodiments of the invention, the method comprises introducing two surgical arms through a single port.

According to some embodiments of the invention, the method comprises comprising modifying an architecture of the system in real time by coupling or decoupling modular units.

According to an aspect of some embodiments of the present invention there is provided a surgical system comprising:

a plurality of surgical arms, a plurality of motor units, each motor unit configured for actuating movement of a surgical arm, where at least two of the plurality of motor units are each configured to attach to another motor unit; and a memory configured to store a model of an attachment configuration of the plurality of motor units.

According to some embodiments of the invention, the system comprises a processor connected to the memory.

According to some embodiments of the invention, the system comprises a user interface through which a user inputs a selected attachment configuration of the plurality of motor units, wherein the user interface is connected to the processor.

According to some embodiments of the invention, the selected attachment configuration is received by the processor and stored in the memory.

According to some embodiments of the invention, the memory stores a plurality of possible attachment configurations and the user selects, through the user interface, one of the plurality of attachment configurations.

According to some embodiments of the invention, the system comprises at least one sensor configured to detect attachment of a motor unit to another motor unit and to send a signal indicating attachment or lack thereof to the processor, wherein the processor derives an attachment configuration from the signal.

According to some embodiments of the invention, the system comprises a user interface;
    wherein the processor is configured to instruct the user interface to display an indication of the attachment configuration of the plurality of motor units.

According to an aspect of some embodiments of the present invention there is provided a method of constructing a system comprising one or more surgical arms, comprising:
    providing:
        a plurality of modular units, each modular unit comprising at least one surgical arm attached to at least one motor unit configured for actuating movement of the surgical arm;
        selecting a surgical approach; and
        coupling one or more modular units to each other in an attachment configuration in accordance with the selected surgical approach.

According to an aspect of some embodiments of the present invention there is provided a surgical system comprising:
    a first separably operable modular motor unit;
    a second separably operable modular motor unit configured to attach to the first modular motor unit;
    two modular surgical mechanical arms, each arm configured to attach to and be actuated by at least one of the motor units;
    an input system;
    a controller configured to receive measured movement from the input system and to send a control signal based on the measured movement of the input system to the motor units.

According to some embodiments of the invention the input system includes a first input device arm and a second input device arm;
    wherein the controller is configured to receive measured movement of the input device arms and to send:
        a first control signal based on the measured movement of the first input device arm to the first motor unit; and
        a second control signal based on measured movement of the second input device arm to the second motor unit.

According to an aspect of some embodiments of the present invention there is provided a modular motor unit configured to actuate an elongate surgical arm comprising a plurality of coaxial surgical arm gears, the modular motor unit comprising:
    a motor unit housing;
    a plurality of motor gears disposed within the housing, each motor gear configured to actuate a surgical arm gear disposed within the housing, where surgical arm gears are coaxial with each other and are coaxial with a long axis of the surgical arm;

wherein the motor gears are sized and positioned such that the long axis of the surgical arm extends from the housing a small distance from a face of the housing.

According to an aspect of some embodiments of the present invention there is provided a surgical system comprising:
    a plurality of modular units, each modular unit comprising:
        a surgical arm;
        a motor unit configured to attach to and actuate the surgical arm; and
        a motor unit housing including a plurality of faces, where more than one face includes at least one connection geometry configured to connect the motor unit housing to a housing of another motor unit.

According to some embodiments of the invention the motor unit housing has rotational symmetry.

According to an aspect of some embodiments of the present invention there is provided a surgical system comprising:
    a plurality of surgical arms;
    a plurality of separably operable motor units, each motor unit configured to attach to and actuate at least one of the surgical arms;
    a plurality of modular user interfaces, each user interface configured to generate an input signal;
    a controller configured to receive the input signals and configured to generate a control signal based on each input signal and send the each control signal to a different motor unit;
    wherein one or more of the motor units is configured to attach to at least another of the motor units.

According to an aspect of some embodiments of the present invention there is provided a system comprising:
    at least one surgical arm, the arm comprising at least one movable joint;
    a motor unit configured for actuating movement of the surgical arm, the motor unit comprising a linear extension of the surgical arm; and
    wherein a portion of the extension configured between the motor unit and the at least one moveable joint comprises a mechanically fixed curvature.

According to some embodiments of the invention the portion of the extension comprises a flexible shaft segment overlaid by a more rigid over tube.

According to some embodiments of the invention a proximal end of the over tube is fixedly attached to the motor unit.

According to some embodiments of the invention the system comprises two surgical arms, wherein at least one of the arms is curved such that the arms converge towards each other or diverge away from each other.

According to some embodiments of the invention the system comprises a third arm.

According to some embodiments of the invention the arm carries a camera.

According to an aspect of some embodiments of the present invention there is provided a unit for actuating linear movement of a system comprising one more surgical arms, comprising:
    an elongated rail comprising a proximal end and a distal end;
    a sliding element positionable on the rail, the sliding element couplable to a motor unit of the system; the sliding element configured to move proximally and distally on the rail to move the motor unit.

According to some embodiments of the invention linear movement of the system on the rail is actuated by a motor configured in the motor unit.

According to some embodiments of the invention the motor comprises a brake.

According to some embodiments of the invention the unit comprises a sensor for detecting if the unit was connected to an external device or system.

According to an aspect of some embodiments of the present invention there is provided a surgical system comprising:

two surgical arm;

a motor construct comprising two motor units arranged side by side, each motor unit configure for actuating movement of one of the surgical arms;

wherein each surgical arm extends distally from its respective motor unit; and wherein the motor units are aligned with respect to each other on opposing sides of central long axis of the motor construct, holding the surgical arms at lateral distance of less than 5 mm between the arms.

According to an aspect of some embodiments of the invention, there is provided a modular unit comprising:

a surgical mechanical arm;

an elongate motor unit comprising: one or more actuating elements configured to actuate the arm and an elongate recess sized and shaped to receive a portion of the surgical arm such that the actuating elements contact the surgical arm.

According to some embodiments of the invention the one or more actuating element is a gear driven by a motor;

wherein the surgical mechanical arm comprises one or more arm gear rotation of which results in movement of a portion of the surgical arm;

wherein, when the arm is within the recess, the gear contacts the arm gear.

According to some embodiments of the invention the surgical mechanical arm incudes a plurality of gears and the motor unit includes a plurality of gears configured to actuate the arm gears, when the arm is within the recess.

According to some embodiments of the invention a long axis of the recess is at an angle of less than 20° of a long axis of the motor unit.

According to some embodiments of the invention the motor unit is activated by insertion of a portion of the surgical arm into the recess.

According to an aspect of some embodiments of the invention, there is provided a method of controlling movement of a surgical mechanical arm comprising:

moving including one or more of bending and rotating portions of the surgical mechanical arm using a motor unit coupled to the surgical mechanical arm;

linearly moving the surgical arm using a linear unit coupled to the arm.

According to some embodiments of the invention the linear unit is coupled to the motor unit.

According to some embodiments of the invention the linear unit is an integral part of the motor unit.

According to some embodiments of the invention the linearly moving includes linearly advancing and retracting the surgical arm.

According to some embodiments of the invention the linearly moving includes linearly moving the surgical arm by linearly moving the motor unit.

According to an aspect of some embodiments of the invention, there is provided a surgical system comprising: a surgical device sized and shaped for insertion into a human body comprising: at least one surgical device articulated limb, which limb comprises: a support portion; a separably bendable first flexible portion coupled to the support portion; a second flexible portion, separably bendable of the first flexible portion, coupled to the first flexible portion; and at least one actuator configured to bend the first and the second flexible portions, an input device, comprising at least one input device articulated limb, which input device limb comprises: a support segment; a first segment coupled to the support segment by a first joint; a second segment coupled to the first segment by a second joint; and at least one sensor configured to measure a first input device angle between the first segment and the support segment and measures a second input device angle between the first segment and the second segment; and a controller configured to: receive a signal from the at least one sensor; send at least one control signal instructing the at least one actuator to: bend the first flexible portion, based on the first input device angle; and bend the second flexible portion, based the second input device angle.

In some embodiments, the control signal instructs the actuator: to bend the first flexible portion such that an surgical device first angle measured between a surgical device effective first segment and a surgical device support segment corresponds to the first input device angle; and to bend the second flexible portion such that an surgical device second angle measured between the surgical device effective first segment and a surgical device effective second segment corresponds to the second input device angle; wherein the surgical device first effective segment is a straight line connecting a long axis center point of the first flexible portion to a long axis midpoint of the second flexible portion; wherein the surgical device second effective segment is a straight line connecting a long axis midpoint of the second flexible portion to a distal end of the second flexible portion.

In some embodiments, the at least one sensor is configured to measure an orientation of the first segment with respect to the second segment and an orientation of the first segment with respect to the support segment; wherein the at least one actuator is configured to rotate the first flexible portion about a first flexible portion long axis and to rotate the second flexible portion about a second flexible portion long axis; wherein the control signal instructs the actuator: to rotate the first flexible portion based on the measured orientation of the first segment with respect to the second segment; and to rotate the second flexible portion based on the measured orientation of the second segment with respect to the first segment.

In some embodiments, the at least one sensor is a motion sensor attached to the articulated limb. In some embodiments, the at least one sensor is a magnetic differential encoder. In some embodiments, the at least one sensor comprises: a first sensor configured to measure the first input device angle; and a second sensor configured to measure the second input device angle. In some embodiments, the first sensor is configured to measure the orientation of the first segment with respect to the second segment; wherein the second sensor is configured to measure orientation of the second segment with respect to the first segment. In some embodiments, the at least one sensor comprises: a third sensor configured to measure the orientation of the first segment with respect to the second segment; and a fourth sensor configured to measure orientation of the second segment with respect to the first segment.

In some embodiments, the first flexible portion is bendable in a first flexible portion single bending plane; wherein the second flexible portion is bendable in a second flexible portion single bending plane.

In some embodiments, the first segment is bendable with respect to the support segment in a first joint single bending plane about the first joint; wherein the second segment is bendable with respect to the first segment in a second joint single bending plane about the second joint. In some embodiments, the first joint and the second joint are pivot joints. In some embodiments, the surgical device comprises a tool coupled to the second flexible portion. In some embodiments, actuation of the tool is controlled by one or more user interface on the input device.

In some embodiments, a ratio between a long axis length of the first segment to a long axis length of the second segment is about a ratio between a length of the first effective segment to a length of a second effective segment. In some embodiments, an effective long axis length of the first segment is about 10-30% longer than an effective long axis length of the second segment.

In some embodiments, the system comprises a first and a second input device limb and a first and second surgical device limb, wherein the first input device limb controls the first surgical device limb, according to claim 1 and wherein the second input device limb controls the second surgical device limb, according to claim 1. In some embodiments, a ratio of a first portion effective length to a first segment length is between 3:1 and 1:1 and a ratio of a second portion effective length to a second segment length is between 3:1 and 1:1.

In some embodiments, the coupling of the input device first segment, second segment and support segment is low enough friction such that moving a portion of the input device causes movement of portions coupled to the portion which are not individually restrained.

In some embodiments, the surgical device does not include motion sensors.

In some embodiments, the controller does not receive feedback from the surgical device.

As will be appreciated by one skilled in the art, some embodiments of the present invention may be embodied as a system, method or computer program product.

Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as selecting an attachment configuration based on a selected surgical approach, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5A is a flowchart of a method of constructing a modular system in accordance with a surgical approach, according to some embodiments of the invention;

FIGS. 7A-7D are diagrams of various configurations of systems comprising different combinations of modular units, according to some embodiments of the invention;

DESCRIPTION OF SPECIFIC EMBODIMENTS OF THE INVENTION

Figure 1A:
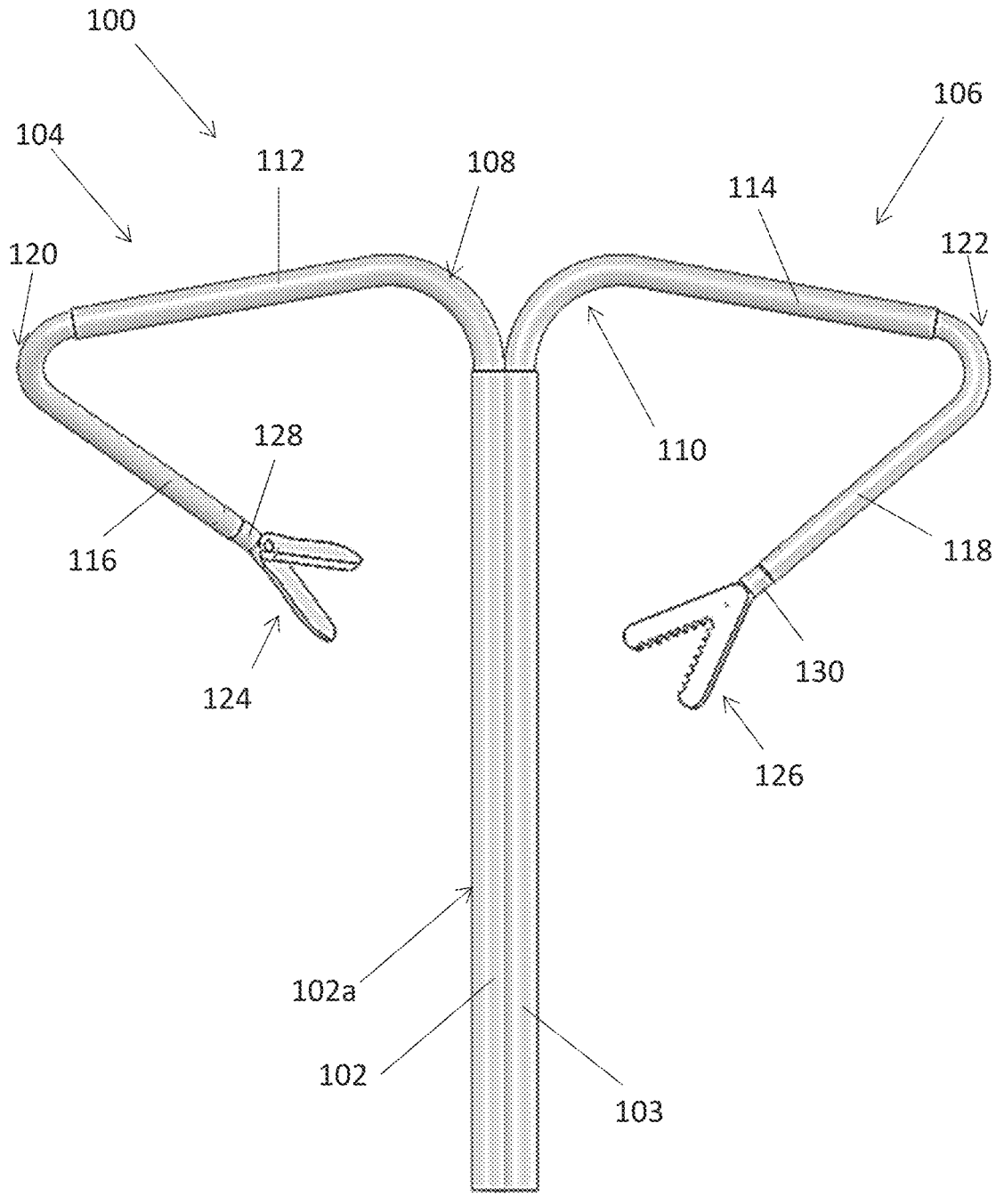
FIG. 1A is a simplified schematic side view of a surgical device including a plurality of arms, according to some embodiments of the invention.

A broad aspect of some embodiments of the invention relates to a system comprising one or more modular unit, each modular unit (also herein termed "surgical modular unit") comprising a surgical arm and a motor unit configured for actuating movement of the surgical arm.

In some embodiments, at least two modular units are configured to be attached to each other. In some embodiments, each modular unit is configured to be operated separately. In some embodiments, the same surgical system is used to perform single port laparoscopic surgery (e.g. where all modular units being used in the surgery are attached and surgical arms inserted through a single port) and multiple port laparoscopic surgery. For example, multiple port laparoscopic surgery being performed when a first subset of the plurality of modular units is detached from a second subset of modular units, and surgical arms of the first subset are inserted through a different port to the second subset. In some embodiments, a plurality of detached subsets of modular units are inserted into a body through a plurality of ports. In an exemplary embodiment, a surgical system includes two modular units configured for surgical operation when attached and inserted into a body through a single port and when detached and inserted through two ports.

In some embodiments, the system includes a controller which sends a control signal to the plurality of motor units to control movement of the surgical arms. In some embodiments, the controller includes at least one input device arm, which, when moved sends an input device signal to the controller. In some embodiments, the controller generates the control signal based on the input device. In an exemplary embodiment, the controller includes two input device arms, where the control signal includes a first control signal instructing movement of a first surgical arm and a second control signal instructing movement of a second surgical arm, where the first control signal is generated based on measured movement of the first input device arm and the second control signal is generated based on measured movement of the second input device arm.

In some embodiments, the controller is configured to be used by one or more people. In some embodiments, the controller is configured to be used by one person when the input arms and/or modular units are attached and to be used by more than one person (e.g. two people) when the input arms and/or modular units are detached.

In some embodiments, a plurality of modular units are configured to, when attached, attach to a patient support (e.g. a bed) by a single support.

In some embodiments, modular units are coupled or attached mechanically. In some embodiments, modular units share coupling and/or alignment. In some embodiments, housing of motor units provides alignment of the modular units. In some embodiments, motor units are magnetically aligned e.g. using one or more magnet positioned in proximity to one or more motor unit housing. For example, in some embodiments, motors units are aligned to each other by aligning portions of a motor unit housing, for example, aligning one or more face of motor unit housings.

In some embodiments, modular units do not share power supply and/or do not share a connection with a controller. For example, each motor unit having a separate connection to one or more a power supply and/or one or more controller.

An aspect of some embodiments of the invention relates to a surgical system including a modular surgical arm configured to be attached to a modular motor unit which is configured to actuate the surgical arm.

For example, in some embodiments, a system includes a plurality of arms and a plurality of motor units where: One or more of the arms are compatible with more than one of the plurality of motor units and/or a plurality of the arms are compatible with one or more of the motor units. In some embodiments, modularity of surgical arms and/or motor units potentially enables, for example replacement of a surgical arm is replaced, for example, moving a surgical arm from one motor unit to another motor unit. In some embodiments, a system includes a plurality of arms and a plurality of motor units where each arm is compatible with more than one motor unit (e.g. each arm is compatible with each motor unit).

An aspect of some embodiments of the invention relates to attachment of a modular surgical arm to a motor unit. In some embodiments, a portion of the surgical arm is inserted into the motor unit. In some embodiments, the portion of the arm which is inserted into the motor unit includes surgical arm gears (e.g. includes a surgical arm gear unit) which are configured to actuate the surgical arm. In some embodiments, arm gears are configured to contact motor unit gears, once the surgical arm is inserted into the motor unit. In some embodiments, the portion of the surgical arm is elongate and is inserted into an elongated recess in a longitudinal face of a motor unit.

In some embodiments, actuating element/s of the motor unit contact the surgical arm, when the arm is inserted into the recess. For example, motor unit gears operably contact surgical arm gears.

For example, in some embodiments, one or more actuating element of the motor unit (e.g. motor gear) is exposed within the recess, for example, at least when the arm is inserted into the recess. In some embodiments, one or more actuatable element (e.g. surgical arm gear) is exposed on the surgical arm, at least once the arm is inserted into the motor unit recess. In some embodiments, once the arm is inserted into the recess, actuation elements of the motor unit contact the surgical arm, for example motor unit gears contact surgical arm gears. In some embodiments, insertion of the arm activates the motor unit, for example, a sensor detects that the surgical arm has been inserted and enables actuation of the arm by the motor unit.

In some embodiments, connection between surgical arm and the motor unit is along a length of the surgical arm and/or motor unit. For example where attachment is, between surgical gear unit and the motor unit. Potentially, connection being along a length of the arm and/or motor unit enables secure connection between the motor unit and the surgical arm, for example, potentially ensuring stability of a position of the surgical arm. Potentially, connection being along a length of the arm and/or motor unit enables contact between a plurality of motor unit actuating elements and the surgical arms (e.g. contact between a plurality of motor gears and surgical arm gears, where surgical arm and/or motor gears are axially separated and/or coaxial).

For example, in some embodiments, an angle of long axis of a portion of surgical arm (e.g. a surgical gear unit which, in some embodiments forms a distal end of the surgical arm) within a motor unit is 0-30° or 0-20° or 0-10° or lower or higher or intermediate angles or ranges, of a long axis of the motor unit.

For example, in some embodiments, a long axis of a surgical arm, when the arm is attached to the motor unit, is housed within the motor unit, extending within the motor unit for 80-99%, or 80-95% or 60-99% of a length of the motor unit.

For example, where 20-50%, or 25-40%, or about 35% or lower or higher or intermediate percentages or ranges, of a length of a surgical arm is attached to the motor unit.

In some embodiments, a kit provided to a user includes separate motor unit/s and surgical arm/s which are then assembled before use of the system. In some embodiments, surgical arm/s in the kit are provided sterile.

In some embodiments, one or more surgical arm is configured to operate using a plurality of tools (e.g. different tool types), where the tools, in some embodiments, are configured to be removably attached to a surgical arm.

An aspect of some embodiments of the invention relates to a motor unit configured to actuate a surgical arm where a surgical arm extends out of the motor unit at a first face of the motor unit, and where the motor unit is configured to be attached to another motor unit at a second motor unit face. In some embodiments, the first face of the motor unit generally defines a plane which is at an angle of 60-120°, 70-110° or 80-100° or about 90° or lower or higher or intermediate ranges or angles to a central axis (e.g. a central long axis) of at least a portion of the surgical arm extending from the first face. For example, a portion of the arm extending from the first face by or 20 mm, or 50 mm or 100 mm, or lower or higher or intermediate distances. In some embodiments, the second face is at an angle to the first face, for example at an angle of 60-120°, 70-110° or 80-100° or about 90° to the first face. In some embodiments, the motor unit has an elongated shape and the second face is a longitudinal face of the motor unit.

In some embodiments, the surgical arm is jointed at the face of the motor unit.

An aspect of some embodiments relates to parallel alignment between motor units in which a longitudinal face of a housing of one motor unit comprises a connection geometry suitable for engaging a face (e.g. a longitudinal face) of a housing of the second motor unit and/or suitable for engaging a connector. In some embodiments, the geometry comprises one or more elements for achieving an interference fit between the housings of the motor unit, such as respective protrusions and indentations.

In some embodiments, a face of a motor unit housing is a portion of the housing where 90-99%, or 90-99.5%, or 95-99% of a surface area of the housing varies by at most 0.1-2 mm, or 0.1-1 mm, or lower or higher or intermediate ranges or values from a plane of the face, where the plane is a tangential plane which contacts the largest surface area of the housing face. In some embodiments, a planar tangent of a motor unit housing longitudinal face is 0-5°, or 0-1°, from parallel to a central long axis of the housing.

In some embodiments, for example, in addition to the connection geometries on the second faces of the motor unit housing, the motor units are configured to interlock with each other, for example using mechanical means such as a plunger lock, pins and/or other fasteners. In some embodiments, the motor units interlock with each other using electromagnetic means. In some embodiments, interlocking between the motor units is released by a quick release mechanism, for example comprising a latch movable for releasing the lock.

In some embodiments, one or more connectors are used to connect two or more motors, e.g. at connection geometries on the motor unit housings. For example, in some embodiments, a connector connects two anchors one anchor located on each of two motor unit housings. In some embodiments, an anchor includes one or more indentation and/or protrusion. In an exemplary embodiment, an anchor is an indentation sized and shaped to receive a portion of a connector.

In some embodiments, a connector is configured to pull a plurality of motor units which it is attaching, together. For example, resistive forces from the connector in reaction to weight of the motor units on the connector acting to pull the motor units together. In some embodiments, a connector is a disposable component. In some embodiments, the connector is configured to be attached and detached from anchor/s. In some embodiments, the connector, once inserted is configured to be broken to detach the motor units from each other. For example, in some embodiments, a connector, once inserted, locks into position and, to be removed, is broken, a potential benefit being connectors which may not be reused. In some embodiments, a connector, once in position attaching a plurality of motor units, does not protrude from outer surfaces of the motor units. Alternatively, in some embodiments, a portion of a connector protrudes, for example, enabling removal of the connector and/or indicating presence and/or position of the connector.

In some embodiments, when a motor unit is attached to a second motor unit, the attached faces are in close contact, for example, where a separation between the attached faces is 0.01-2 mm or 0.01-1 mm, or at most 1 mm or at most 0.5 mm or lower or higher or intermediate distances or ranges. In some embodiments, when a motor unit is attached to a second motor unit, the attached faces directly contact each other. In some embodiments, the direct contact is for at least 90% of the surface area of the faces or at least 80% or at least 95% or at least 98% or 80-95%, or lower or higher or intermediate ranges or percentages.

In some embodiments, a motor unit housing faces, (in some embodiments, excluding portions of the faces with connection geometries) are sufficiently planar (e.g. deviating from planar by at most 2 mm or 1 mm or 0.5 mm or 0.1 mm or lower or higher or intermediate distances for at least 80% or 90% or 95% or 99% of a surface area of the plate, or lower or higher or intermediate percentages) that when the faces are connected they come into close contact (e.g. as quantified above). In some embodiments, connection geometries of two motor units are sized and/or shapes such that the faces, when connected at the connection geometries are in close contact (e.g. as quantified above). For example, in some embodiments, a protrusion on a first motor unit housing is fits into an indentation on a second motor unit housing sufficiently well, that the motor units when connected are in close contact.

In some embodiments, a single modular unit is used independently for performing surgery. Additionally or alternatively, multiple modular units such as 2, 3, 4, 6 units or intermediate or larger number of units are used for performing surgery.

In some embodiments, a motor unit is configured for detecting whether it has been connected to one or more additional motor units, for example via a sensor such as a microswitch.

In some embodiments, motor units are aligned by magnetic means, for example by one or more magnet acting at a motor unit face (e.g. longitudinal face).

An aspect of some embodiments relates to holding surgical arms close to each other such that a lateral distance between the arms (e.g. a lateral distance between longitudinal axes of the arms) is less than 10 mm, less than 5 mm, less than 1 mm or intermediate, longer or shorter distances. In some embodiments, each motor unit is collinear with the surgical arm actuated by the motor unit, so that when the arms are connected to the motor units they are held in a parallel position with respect to each other. In some embodiments, a motor unit is an elongate element, at least a portion of the surgical arm extending out of the motor unit is elongate. In some embodiments, a long axis of the elongate motor unit is parallel to a long axis of the elongate portion of the surgical arm extending out of the motor unit.

In some embodiments, the surgical arm extends distally from the motor unit at a lateral distance smaller than 5 mm, smaller than 3 mm, smaller than 1 mm from a longitudinal face of the motor unit which engages a respective longitudinal face of the second motor unit holding the second arm. In some embodiments, more than two arms are held close to each other such that the lateral distance between the arms is less than mm, less than 5 mm, less than 1 mm or intermediate, longer or shorter distances. For example, in some embodiments, 3 or 4 or 5 or 3-10 surgical arms are held close to each other.

A potential advantage of the surgical arm positioned closely to the engaging face of the motor may include holding the arms of the adjacent motor units closely to each other, potentially allowing for insertion of the arms together through a relatively narrow opening to the patient body. For example, through a small incision of e.g. less than 5 cm in length and/or breadth, or less than 3 cm, or less than 2 cm, or less than 1 cm, or 0.1-5 cm, or 0.1-3 cm, or lower or higher or intermediate dimensions or ranges. For example, through a natural body orifice, e.g. the vagina, e.g. the anus, e.g. the trachea, e.g. the esophagus. For example, through an incision contained within the umbilicus.

In some embodiments, 3 motor units are constructed together to hold 3 surgical arms in proximity to each other. In an example, a first arm is defined to imitate the left arm; a second arm is defined to imitate the right arm; and a third arm carries a surgically assisting device such as a camera.

A broad aspect of some embodiments of the invention relates to interconnection of a plurality of motor unit modules in a variety of spatial configurations. In some embodiments, a motor unit is configured to interlock with one or more additional motor unit at a plurality of positions. For example, in some embodiments, a motor unit has a housing which includes a plurality of anchors which are, for example, located on different parts of the motor unit housing.

In some embodiments, a motor unit is configured to connect to other motor unit/s (e.g. includes a plurality of anchors) at different radial positions from a central long axis of the motor unit. For example, in some embodiments, a motor unit (e.g. a motor unit housing) has at least one anchor on more than one longitudinal face.

Additionally or alternatively, in some embodiments, a motor unit is configured to connect to other motor unit/s (e.g. includes a plurality of anchors) at different axial positions on the motor unit. For example, in some embodiments, a motor unit has a plurality of anchors distributed at different axial positions along a single longitudinal face of the motor unit.

In some embodiments, one or more anchor provides more than one connection geometry between motor units. In some embodiments, one or more anchor provides a range of connection positions e.g. a continuous range, for example, in some embodiments, one or more motor unit has an anchor configured for slide connection.

In some embodiments, a plurality of motor units are connected by one or more connector. In some embodiments, a single connector is configured to connect two motor units. For example, in an exemplary embodiment, a first and a second motor unit, having a first and a second slide connection anchor respectively, are connected by a connector which is sized and/or shaped to fit into the anchors thereby connecting the first and second motor units. In some embodiments, a plurality of connectors connect two motor units.

In some embodiments, a plurality of motor units are connected by placing the motor units into a connector, e.g. the connector is a sleeve sized and shaped to hold and/or interconnect a plurality of motor units.

In some embodiments, the surgical system includes a model of a configuration of attachment of the motor units. In some embodiments, the model is stored in a memory by a processor. In some embodiments, a model is selected by a user, for example, before and/or after connection (e.g. mechanical) of the modules.

In some embodiments, there are two modular units and the model includes a first and a second option, the first option where the modular units are connected, and the second option where the modular units are disconnected.

In some embodiments, a motor unit is configured, at a plurality of positions, for attachment to another motor unit. For example, in some embodiments, a plurality of attachments around a circumference of a motor unit are possible.

In some embodiments, a motor unit is configured for attachment to other motor units at multiple positions around a cross sectional circumference of the motor unit. In an exemplary embodiment, a motor unit includes four, equally spaced positions.

In some embodiments, motor units are attached to each other by one or more connector. In some embodiments, the connector is a separate part. In some embodiments, each motor unit includes one or more anchor, the anchor including an indentation, where a connector is shaped and/or sized to fit simultaneously into two anchors, e.g. thereby connecting two motor units. In an exemplary embodiment, attachment between the connector and the anchors includes slide attachment. In some embodiments, slide attachment enables axial adjustment of position and/or selecting of axial position of motor units with respect to each other.

A broad aspect of some embodiments of the invention relates to sizing and positioning of motor gears with respect to a surgical arm axis within a motor unit housing. Where, in some embodiments, motor gears drive surgical arm gears to effect movement of the surgical arm. In some embodiments, a plurality of surgical arm gear axes (e.g. all surgical arm gears for an arm) are collinear, where a gear axis is an axis about which the gear rotates.

In some embodiments, a longitudinal axis of a surgical arm and associated arm gears is positioned between one or more outer face (e.g. longitudinal face) of the motor unit housing and an axis or axes of motor gears driving the arm gears.

In some embodiments, one or more motor gear is sized such that a surgical arm is at a small lateral distance from a face (e.g. a longitudinal face) of a motor unit housing for example, 0.1-5 mm or 0.1-2 mm, or 0.5-2 mm, or lower or higher or intermediate distances or ranges. In some embodiments, a plurality of gears are sized such that a surgical arm is at a small lateral distance from a longitude face of the motor housing. For example, in embodiments, where an axis of one or more motor gear is between a surgical arm axis and a face of the motor unit, reduction in size of the motor gear reduces a distance between the surgical arm axis and the motor unit face.

In some embodiments, more than one motor gear drives a single surgical arm gear, for example, potentially enabling reduction in size of motor gears whilst maintaining a required level of torque.

In some embodiments one or more motor gear is small, for example a gear (or gears, or all motor gears of a motor unit, in some embodiments) having 1-20 mm diameter, or 1-5 mm diameter or lower or higher or intermediate diameters or ranges. In some embodiments, a motor unit has one or more motor gear (e.g. all motor gears of a motor unit) which is the same size or smaller than one or more surgical arm gear, for example, where the motor gear diameter is 20-100% or 20-95% or 40-70% of a surgical arm gear, or lower or higher or intermediate percentages or ranges.

A potential benefit of small motor gears is the ability to connect a motor unit to another other motor unit at a plurality of faces of the motor unit (e.g. all the faces of the motor unit) whilst maintaining the surgical arms close together. This potentially enables a large range of configurations of motor units where surgical arms are held closely together.

In some embodiments, motor gears are all collinear, potentially reducing a minimum required size of a motor unit and/or reducing a distance between a surgical arm axis and longitudinal face/s of a motor unit.

An aspect of some embodiments relates to automated actuation of linear movement of a system comprising one or more surgical arms. In some embodiments, a mechanism referred to herein as a "linear unit" is configured for actuating advancement and/or retraction of one or more modular units, for example advance and/or retract a surgical arm in and/or out of the patient body. In some embodiment, the linear unit is integrated in the motor unit. Additionally or alternatively, the linear unit is configured to be coupled to the motor unit.

In some embodiments, the linear unit comprises a rail and a sliding element positionable on the rail. In some embodiments, the sliding element connects to the motor unit so as to allow for sliding of the motor unit with respect to the rail.

In some embodiments, actuation of linear movement is driven by a motor.

Optionally, the motor is disposed in the motor unit such that when the motor unit is attached, via the sliding element, to the rail, the motor drives movement of the motor unit on the rail.

In some embodiments, the linear unit is configured for connecting to an external device or system. Optionally, the linear unit comprises a sensor, such as a microswitch, configured for detecting whether the linear unit was connected to an external device or system.

In some embodiments, a single linear unit is used for moving more than one motor unit, for example for moving two motor units attached together.

An aspect of some embodiments relates to constructing a modular system in accordance with a surgical approach. In some embodiments, a number and/or spatial arrangement of modular units and/or a number of surgical arms is selected in accordance with a selected surgical approach.

In some embodiments, selecting a surgical approach comprises selecting surgical port/s through which the surgery is performed. For example, including selecting a number and/or a shape and/or location of surgical port/s through which the surgery is performed.

A port may comprise a natural body orifice, an incised opening and/or any other opening allowing access to the patient's body. In some embodiments, a port comprises a port element which is, for example, coupled to the patient's body and through which one or more surgical arms accesses the patient's body.

In some embodiments, modular units are selected and/or arranged (e.g. spatially arranged) such that one or more surgical arms operate within a port. Additionally or alternatively, separate modular units are positioned at different ports. Additionally or alternatively, one or more surgical arms operate within a first port and then are moved to a second port.

In some embodiments, a spatial arrangement of modular units based on a shape and/or size of the port through which surgical arms associated with the modular units are inserted.

For example, in an exemplary embodiment, a linear spatial arrangement of modular units is selected, where units are sequentially connected in a line, for insertion into a patient through a linear port (e.g. linear incision)

In some embodiments, selecting a surgical approach includes selecting a surgical path (e.g. that surgical arm/s delineate) through a patient to a surgical target. In some embodiments, more than one surgical path is selected for example, multiple paths from one port (e.g. different arms inserted into a single port follow different paths within a patient body), for example, one or more path from each port where there are multiple ports.

In some embodiments, a spatial arrangement of modular units is selected based on selected surgical path/s. For example, in an exemplary embodiment, a linear spatial configuration of modular units is selected, for insertion into a patient when a narrow access profile is desirable, for example, where access is between ribs, for example, where a surgical path within the subject avoiding surgical obstacles is narrow. In some embodiments, a processer provides a recommended spatial configuration of modular units (one or more recommendation, e.g. displayed to a user), based on user inputted information including, for example, feature/s of a selected surgical path and/or approach, number of ports, size and/or position of ports, anatomical information, e.g. provided by imaging and/or anatomical maps.

In some embodiments, the system includes a user interface which is configured to display an indication of an attachment configuration of the plurality of modular units and/or motor units. In some embodiments, the user interface receives a model of an attachment configuration and then displays an indication of the attachment configuration based on the received model. Where, for example, the indication is an illustration of attached modular units and/or a numerical indication and/or one or more lit light. In some embodiments, the model received is based on signals produced by the modular units and received by a processor. For example, in some embodiments, a user positions and/or attaches a plurality of modular units, and one or more of the units sends a signal indicating their attachment configuration to the processor. In some embodiments, based on this signal, the processor generates and/or selects (e.g. from a list) a model of an attachment configuration. In some embodiments, a user selects an attachment configuration at a user interface, (for example, selecting the configuration from a list, for example, attaching virtual modular units in a virtual space), and the processor generates a model of an attachment configuration from the user input. In some embodiments, the user selected model of an attachment configuration is stored in a memory and/or displayed on a user interface.

In some embodiments, a model of an attachment configuration includes, for example, one or more of a number of modular units, an indication of which faces of which motor units are attached to each other, an indication of motor unit type, an indication of a surgical arm type.

In some embodiments, modular units are spatially arranged (e.g. for operation within a single port) by interlocking a plurality of modular units. In some embodiments, the surgical arms are pre-positioned and/or are moved to a selected position with respect to the ports for accessing the patient's body. In some embodiments, arms are configured for converging towards each other. Additionally or alternatively, arms are configured for diverging away from each other. In some embodiments, an arm portion (for example an arm portion extending between a motor unit and a first joint of the surgical arm) is configured to be shaped (e.g. bent) to a selected configuration. Some embodiments comprise a bendable over tube for setting a position of one or more arms with respect to the patient body and/or with respect to each other.

A broad aspect of some embodiments of the invention relates to control of movement of a modular unit surgical arms using a modular control units. In some embodiments, a configuration of a connected plurality of modular control units matches a configuration of connected surgical modular units. For example, in some embodiments, two surgical modular units are connected (e.g. at longitudinal faces of the surgical units) and movement of the surgical modular units is controlled by two connected modular control units. In some embodiments, a modular control unit includes an input device arm where a support of the input device arm is configured to attach the input device arm in proximity to another input device arm. In some embodiments, input device arms are configured to be attached to each other, where attachment is e.g. at their supports.

In some embodiments, modular units which are configured to be detached from each other, for example, potentially enabling cleaning of the modular units, for example, including surfaces which are close together and/or in contact with each other when the modular units (e.g. at motor unit housing) are attached (e.g. ease of cleaning of motor unit housing longitudinal faces).

An aspect of some embodiments of the invention relates to a surgical system including a plurality of surgical arms each arm attached to a motor unit configured to actuate the arm where one or more of the surgical arms includes a mechanically fixed curvature.

In some embodiments, the curvature brings arms towards each other, for example, a distal portion of the arms being at a smaller separation than a portion of the arms extending from the motor units. Potentially, in some embodiments, this smaller separation enables insertion of the arms through a single small port.

In some embodiments, the curvature increases a separation between the surgical arms, a distal portion of the arms being at a larger separation than a portion of the arms extending from the motor units, Potentially, in some embodiments, this larger separation enables insertion of the arms through more than one port and/or from more than one direction, whilst being actuated by connected motor units.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1A is a simplified schematic side view of a device 100 (e.g. surgical device) including a plurality of arms, according to some embodiments of the invention. In some embodiments, the device includes a first arm 104 and a second arm 106.

In some embodiments, one or both surgical arms are sized and/or shaped for insertion into a human body.

In some embodiments each arm 104, 106 includes a support segment 102, 103, coupled to a first segment 112, 114 by a first connecting section 108, 110, where first segment 112, 114 is coupled to a second segment 116, 118 by a second connecting section 120, 122, and a third segment 124, 126 coupled to second segment 116, 118 by a third connecting section 128, 130.

In some embodiments, one or more of support segments 102, 103 are rigid. In some embodiments one or more of support segments 102, 103 are flexible or include a flexible portion.

Figure 1B:
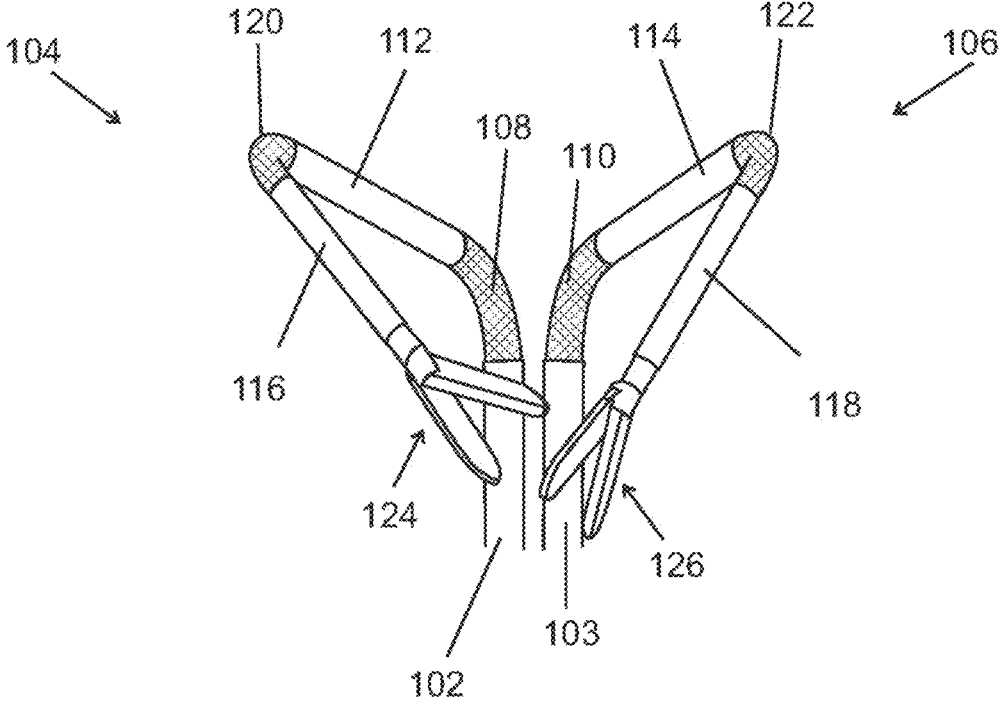
FIG. 1B is a simplified schematic of a device including a plurality of arms, according to some embodiments of the invention.

In some embodiments, support segments 102, 103 are coupled, e.g. by a cover 102a. In some embodiments, support segments are coupled at only a portion of the torso length or are not coupled: FIG. 1B is a simplified schematic of a device 100 including a plurality of arms 104, 106, according to some embodiments of the invention.

In some embodiments, one or more arm includes a humanoid like structure. For clarity, in some portions of this document, device segments and connecting sections are referred to by anatomical names: Support segments 102, 103 are also termed first torso 102 and second torso 103, first connecting sections 108, 110 are also termed first shoulder joint 108, second shoulder joint 110, first segments, 112, 114 are also termed first humerus 112 and second humerus 114, second connecting sections 120, 122 are also termed first elbow joint 120, and second elbow joint 122, second segments 116, 118 are also termed first radius 116 and second radius 118 and third segments 124 and 126 are also termed first hand tool 124 and second hand tool 126.

In some embodiments, one or more connecting section includes a hinge. In some embodiments, one or more connecting section is flexible and/or includes a flexible portion. In an exemplary embodiment, a device arm includes an elbow joint and a shoulder joint where bending of the joint is distributed along the joint in a direction of a joint long axis.

In some embodiments, torsos 102, 103 are close together, for example, a long axis of first torso 102 and a long axis of second torso 103 are within 5 mm, or 3 mm, or 1 mm of each other. Alternatively, torsos 102, 103 are spaced apart from each other.

Additionally or alternatively, torsos 102, 103 are configured to converge or to diverge relative to each other. Optionally, a torso is curved.

In some embodiments, one or more device segment has a substantially cylindrical external shape (e.g. radius, humerus). In some embodiments, joints have circular long axis cross-section. Alternatively, in some embodiments, one or more device segment and/or joint has non-circular cross section external shape, for example, oval, square, rectangular, irregular shapes.

In some embodiments, a surgical arm includes one or more short and/or adjustable segment. In some embodiments, flexible portions are directly connected.

In some embodiments, a flexible portion comprises a plurality of stacked links.

Figure 1C:
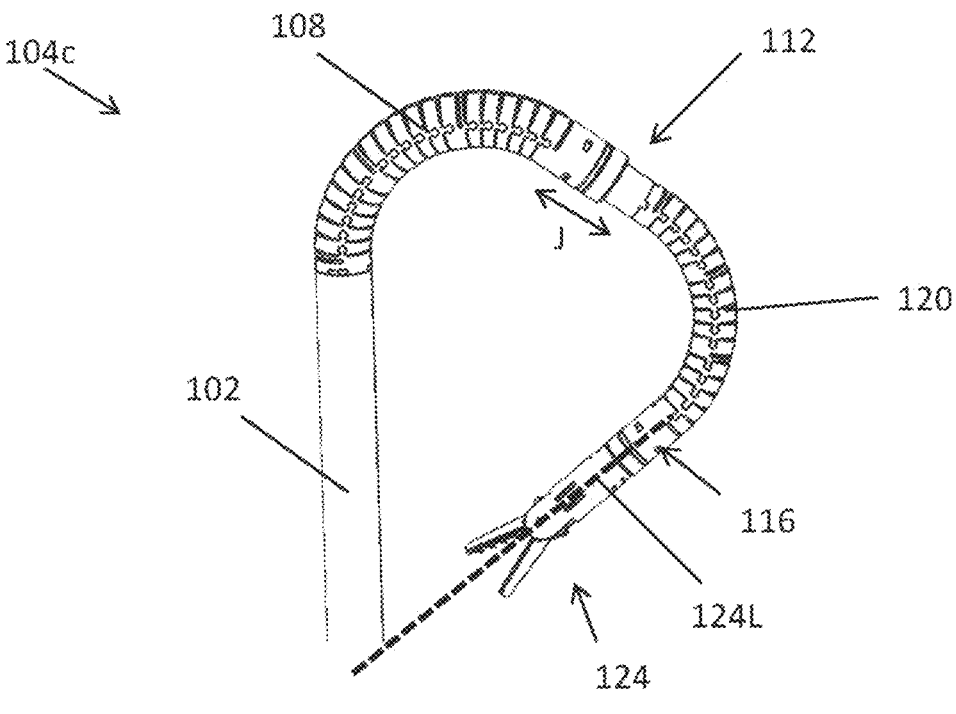
FIGS. 1C-1D are simplified schematic side views of surgical arms, according to some embodiments of the invention.
Figure 1D:
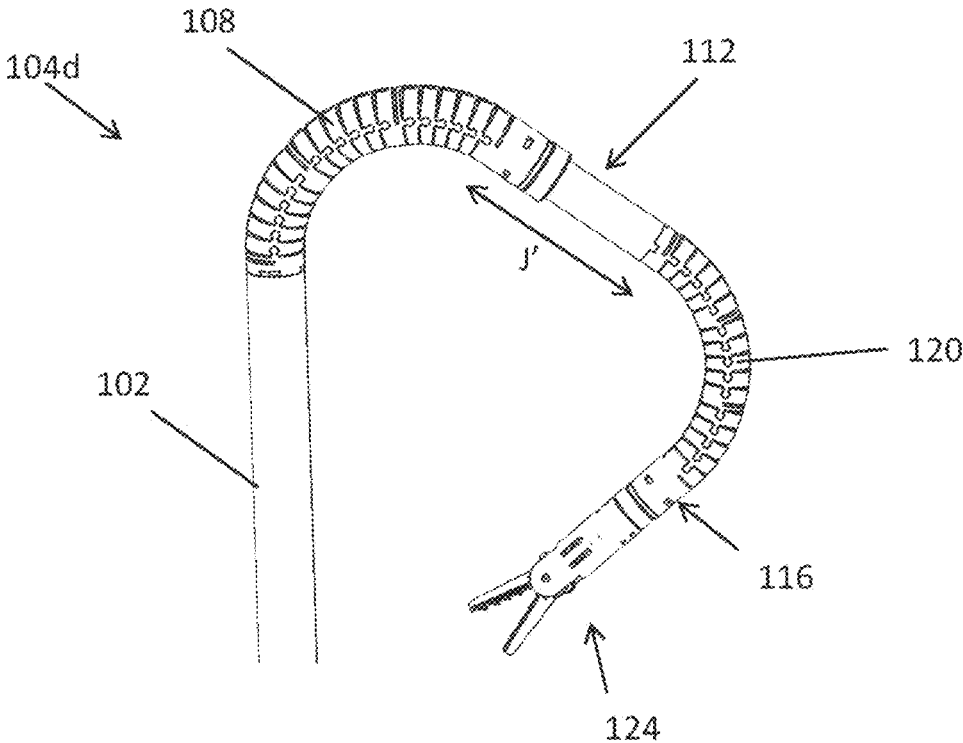

FIGS. 1C-1D are simplified schematic side views of surgical arms, according to some embodiments of the invention. FIG. 1C illustrates an exemplary embodiment where a humerus segment 112 is short, for example, the segment including a long axis length, J of 1-50 mm, or 1-35 mm, or 10-20 mm, or approximately 10 mm or lower or higher or intermediate ranges or lengths.

In some embodiments, a user selects arm/s including desired segment lengths, where for example, selection is based on patient anatomy and/or a procedure to be performed. For example, when treating a child a user, in some embodiments, selects one or more arm with one or more short segment (e.g. as illustrated by FIG. 1C). For example, when treating an obese patient, a user, in some embodiments, selects an arm with one or more a long segment for example, a standard arm with a long humerus segment (e.g. as illustrated by FIG. 1D) (e.g. humerus segment length, J' is 10-100 mm, or 20-35 mm, or 10-20 mm, or lower or higher or intermediate ranges or lengths).

In some embodiments, a device includes a kit with different structured arms (e.g. different segment lengths, e.g. different arm sizes).

Alternatively or additionally, in some embodiments, one or more segment length is adjustable, e.g. during a treatment and/or during set-up of the device. For example, in some embodiments, the arm illustrated in FIG. 1C is adjustable (e.g. by telescoping of humerus segment 112) is adjustable to the configuration illustrated in FIG. 1D.

In some embodiments, extension and/or retraction of one or more segment is effected by a portion connected to the segment (e.g. a segment extension) being moved with respect to other portions of a surgical arm. For example, in some embodiments, a segment extension is moved (e.g. by a motor located in a motor unit) to increase a length of a segment. In some embodiments, a motor uses a screw mechanism to move the segment extension.

In some embodiments, a device arm has at least the freedom of movement of human arms. Generally, segments of human limbs (e.g. arms, legs) move by flexion and extension from a proximal segment joint, and rotation around the proximal segment joint. For example, a human radius flexes and extends at the elbow and rotates around the elbow.

The term proximal joint herein refers to the joint which is least removed from the torso to which a segment is coupled, e.g. a hand proximal joint is the wrist, a radius proximal joint is the elbow joint, a humerus proximal joint is the shoulder joint.

The term proximal segment herein refers to the segment which is least removed from the torso to which a segment is coupled (e.g. by a proximal segment joint). For example, a hand proximal segment is the radius, a radius proximal segment is the humerus, a humerus proximal segment is the torso.

In some embodiments, one or more joint is uni-directionally bendable and extendable. In some embodiments, segment rotation around a segment proximal joint is achieved by rotation of a proximal segment around a proximal segment long axis.

For example, rotation of the hand around the wrist joint is by rotation of the radius around a radius long axis.

Generally, human freedom of movement for arms includes limits to the angles of rotation and flexion. Optionally, in some embodiments, the device is restricted to human freedom of movements e.g. during one or more control mode. Alternatively, the device is configured to allow movement having additional degrees of freedom relative to human arm movement.

Figure 2A:
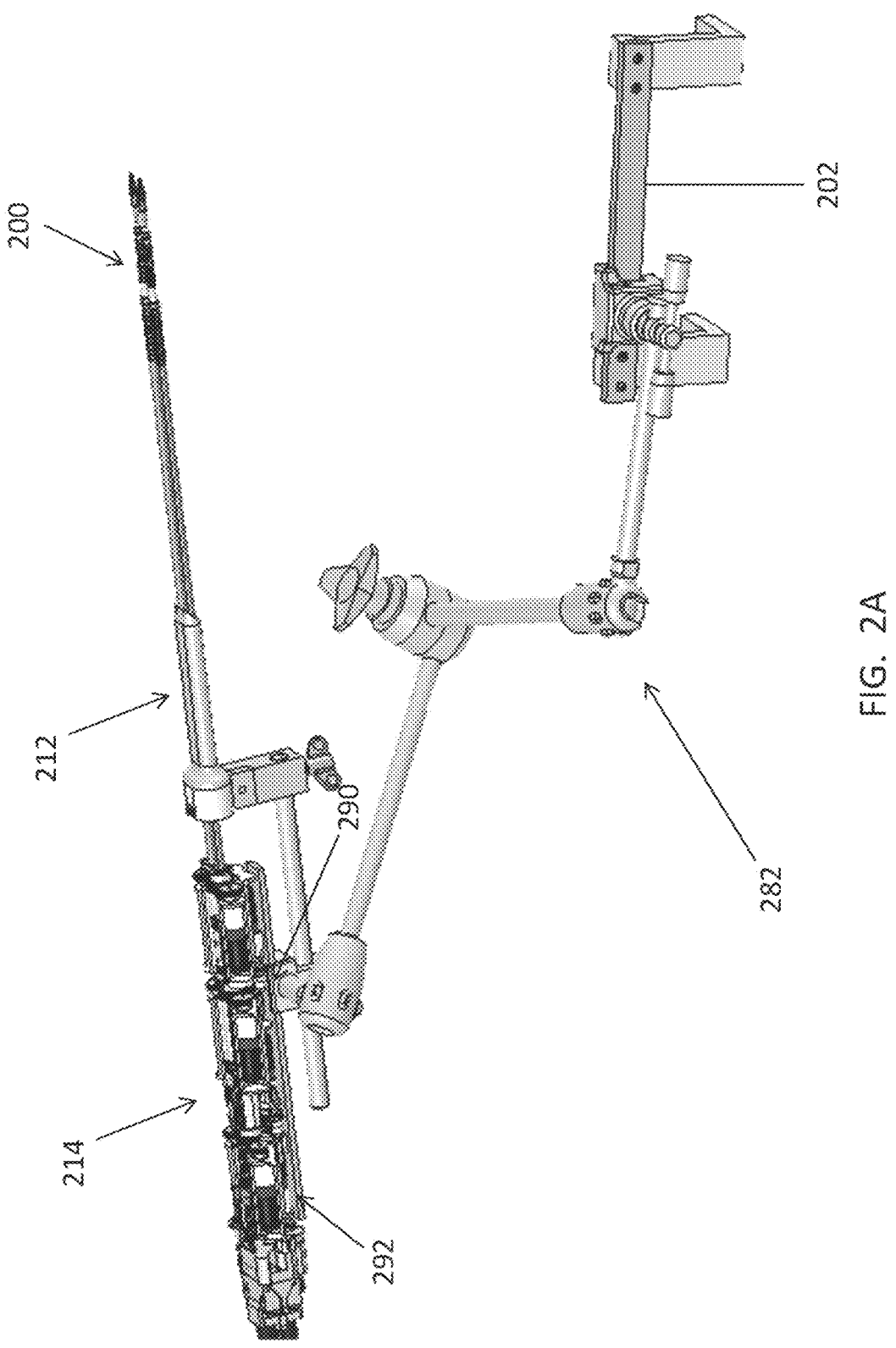
FIG. 2A is a simplified schematic of a device, held by a support, according to some embodiments of the invention.

FIG. 2A is a simplified schematic of a device 200, held by a support 282, according to some embodiments of the invention.

In some embodiments, support 282 attaches to a portion of a patient operating surface, e.g. rail 202. In some embodiments, position of attachment of support 282 on rail 202 is adjustable, for example enabling linear adjustment of position of attachment of the support to the patient operating surface.

In some embodiments, support 282 is attached to port 212 of a motor construct 214, device 200 being supported by attachment to motor construct 214. In this example, motor construct 214 comprises two motor units configured for actuating two arms of device 200, according to some embodiments. It is noted that in some embodiments, the device comprises a different number of arms such as 1, 3, 4, 6, 8 arms or intermediate, higher or lower number. Optionally, each arm is actuated by a respective motor unit.

In some embodiments, port 212 is placed at an opening to the patient's body, for example at an incision and/or at a natural body orifice such as the vagina and/or anus and/or mouth. In some embodiments, port 212 is attached to the patient's body using sutures and/or other attachment means. Additionally or alternatively, port 212 is fixated to the operating surface 202.

In some embodiments, support 282 includes a plurality of articulations where angles between segments and/or segment lengths are adjustable, for example, enabling adjustment of position and/or angle of a device 200 including surgical arms and/or a port 212 and/or motor construct or construct 214 (e.g. which actuate device 200 arm/s).

In some embodiments, one or more motor is used to move device 200, with respect to one or more portion of the system (e.g. with respect to port 212 and/or motor construct 214), for example, into and/or out of a patient. In some embodiments, motor construct 214 includes one or more motor for movement of one or more device arm with respect to the motor construct, where, for example, one or more support segment position is changed with respect to the motor construct. In some embodiments, movement of device 200 is controlled by a user, optionally using input object control and/or a user interface.

In some embodiments, the motor unit includes one or more position sensor. In some embodiments, a position sensor is placed adjacent the motor for sensing a current rotation angle of the motor. In some embodiments, the position sensor is magnetically operated, using a magnet placed on the motor gear and sensing the magnetic flux to determine a current position of the motor gear.

In some embodiments, the motor unit is controlled by a processor including a memory which stores commands. In some embodiments, data from position sensor/s and/or from control memory is used to infer a position of device portion/s. In some embodiments, the motor unit is controlled by a processor configured in the user's input device.

In some embodiments, motor unit includes structure (e.g. including electrical contact/s), for example, for delivery of monopolar and/or bipolar energy to the device (e.g. to a device end effecter).

In some embodiments, support 282 is configured to move motor construct 214 linearly, for example to advance device 200 into and/or out of the patient's body. In some embodiments, linear movement is obtained by a linear unit 290.

Figure 2B:
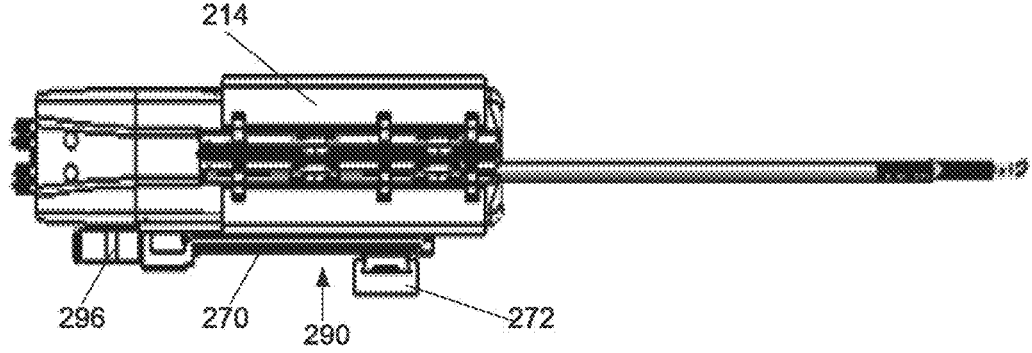
FIGS. 2B-2C illustrate actuation of a device by a linear unit, according to some embodiments of the invention.
Figure 2C:
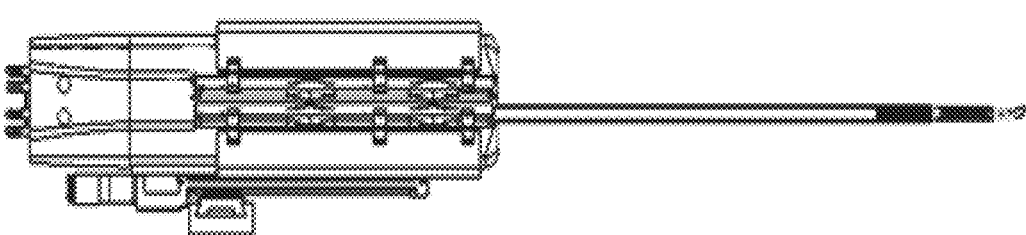

FIGS. 2B-2C illustrate actuation of a device by linear unit 290, according to some embodiments.

In some embodiments, linear unit 290 defines a rail 270 on which an element 272 coupled to motor construct 214 is slidably received. Optionally, linear movement (e.g. sliding) of motor construct 214 relative to linear unit 290 is actuated by a motor 296. In some embodiments, motor 296 is a component of motor construct 214. In an example, in a motor construct comprising 12 motors for actuating articulation of two surgical arms (e.g. 6 motors driving movement of each arm), motor 296 is a $13^{th}$ motor.

Optionally, motor 296 is disposed externally to a housing of the motor unit.

FIG. 2B illustrates motor construct 214 at an initial position with respect to linear unit 290. In FIG. 2C, motor construct 214 has been moved in a distal direction (e.g. slid) to an advanced position relative to linear unit 290.

A potential advantage of motorized entry and/or retraction from the body using the linear unit may include obtaining a higher degree of movement accuracy, for example as compared to manually-actuated entry into the body.

In some embodiments, linear movement of the motor construct which in turn actuates linear movement of the arm(s) is performed concurrently with one or more other articulations provided by support 282, as shown in FIG. 2A. Such actuation may be advantageous, for example, during insertion into the body, providing for example for simultaneous bending and advancing into the body.

Figure 3A:
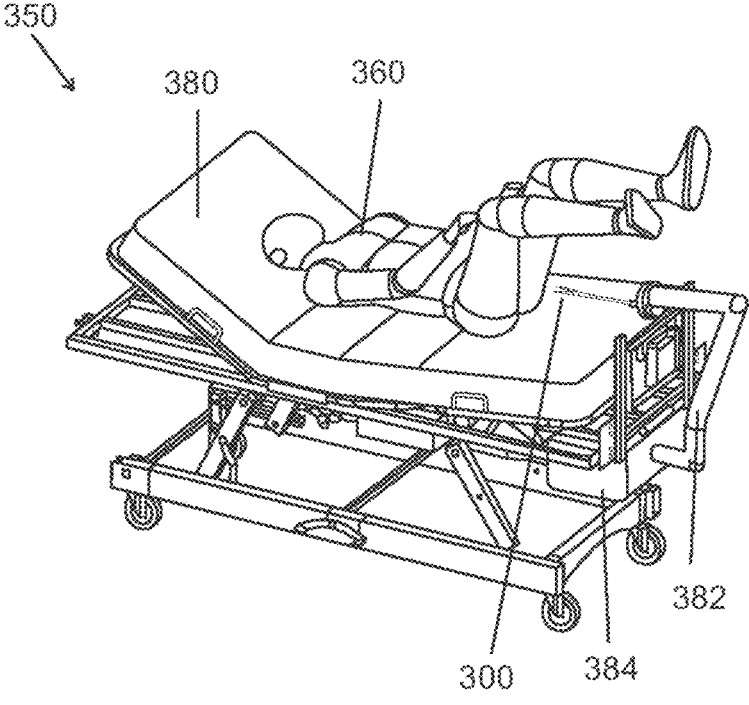
FIGS. 3A-3B are simplified schematic views of a system where a device is held by a support, according to some embodiments of the invention.

FIG. 3A is a simplified schematic view of a system 350 where a device 300 is held by a support 382, according to some embodiments of the invention.

In some embodiments, a device 300 is coupled to a bed 380. In some embodiments, a patient 360 lies on bed 380 for surgical procedures using device 300.

In some embodiments, one or more component of the device, for example one or more part of device control (e.g. motors) is located underneath bed, e.g. in a housing 384. In some embodiments, support 382 connects device 300 to housing 384.

Optionally, other components, for example transformers, connectivity to other components e.g. the display, are located in housing 384.

In an exemplary embodiment, a main motor unit (or a motor construct comprising a plurality of motor units) for control of movement of the device is located in housing 384, where for example, in some embodiments, torque transfer element/s transfer torque from motor/s within housing 384 to device 300 and/or elongated elements for effecting flexion of device joints are coupled to motors within housing 384.

In some embodiments, control of movement of the device above the bed, using a motor unit underneath the bed is via an orientation controller, for example using a parallelogram linkage, e.g. as described in International Patent Application Publication No. WO2011/036626 which is herein incorporated by reference into the specification in its entirety.

A potential benefit of one or more component being located underneath a bed (e.g. inside housing 384), is reduced footprint of the system in an operating room. A further potential benefit of components being located underneath a bed as opposed to above and/or around the bed is potentially improved access to a patient (e.g. in an emergency situation).

A potential benefit of the device being coupled to a bed is the ability to move and/or change an angle of the bed, for example, during surgery, while the device remains in the same position relative to the bed and/or patient. Alternatively, or additionally, in some embodiments, a device position with respect to the patient and/or the bed is adjustable, for example, before treatment with the device and/or during surgery.

Optionally, in some embodiments, support 382 moves device into position for surgery. In some embodiments, support 382 moves device into a desired position for insertion into patient 360. In some embodiments, support 382 moves device vertically, and/or horizontally, and/or laterally, and/or inserts device 300 into a patient 360 and/or withdraws device 1100 from the patient.

In the embodiment illustrated by FIG. 3A, support arm 382 and housing 384 are located at the foot end of 384. A potential benefit of this location is ease of surgery through a patient's undercarriage, for example, through the vagina.

In FIG. 3A, patient 360 is illustrated in a suitable position for insertion of the device into the vagina, the patient's legs are elevated and apart (e.g. held by stirrups which are not shown).

Figure 3B:
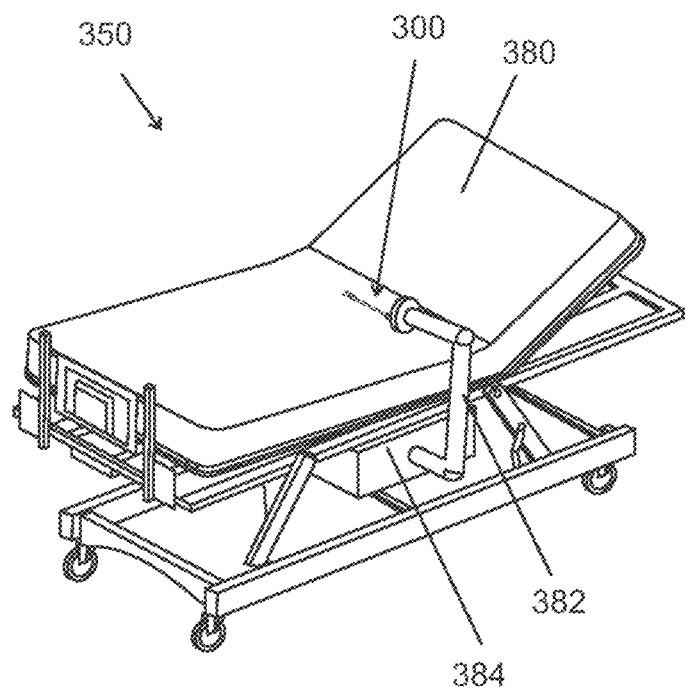

FIG. 3B is a simplified schematic view of a system 350 where a device 300 is held by a support 382, according to some embodiments of the invention. In the embodiment illustrated by FIG. 3B, support arm 382 and housing 384 are located at a long axis center of the bed 380. A potential benefit of this location is ease of abdominal and/or thoracic surgery using the device.

In some embodiments, a housing position underneath the bed and/or a position around the bed from where the arm meets the housing are adjustable. For example, the arm and/or housing are moved for different surgeries.

Figures 4A, 4B:
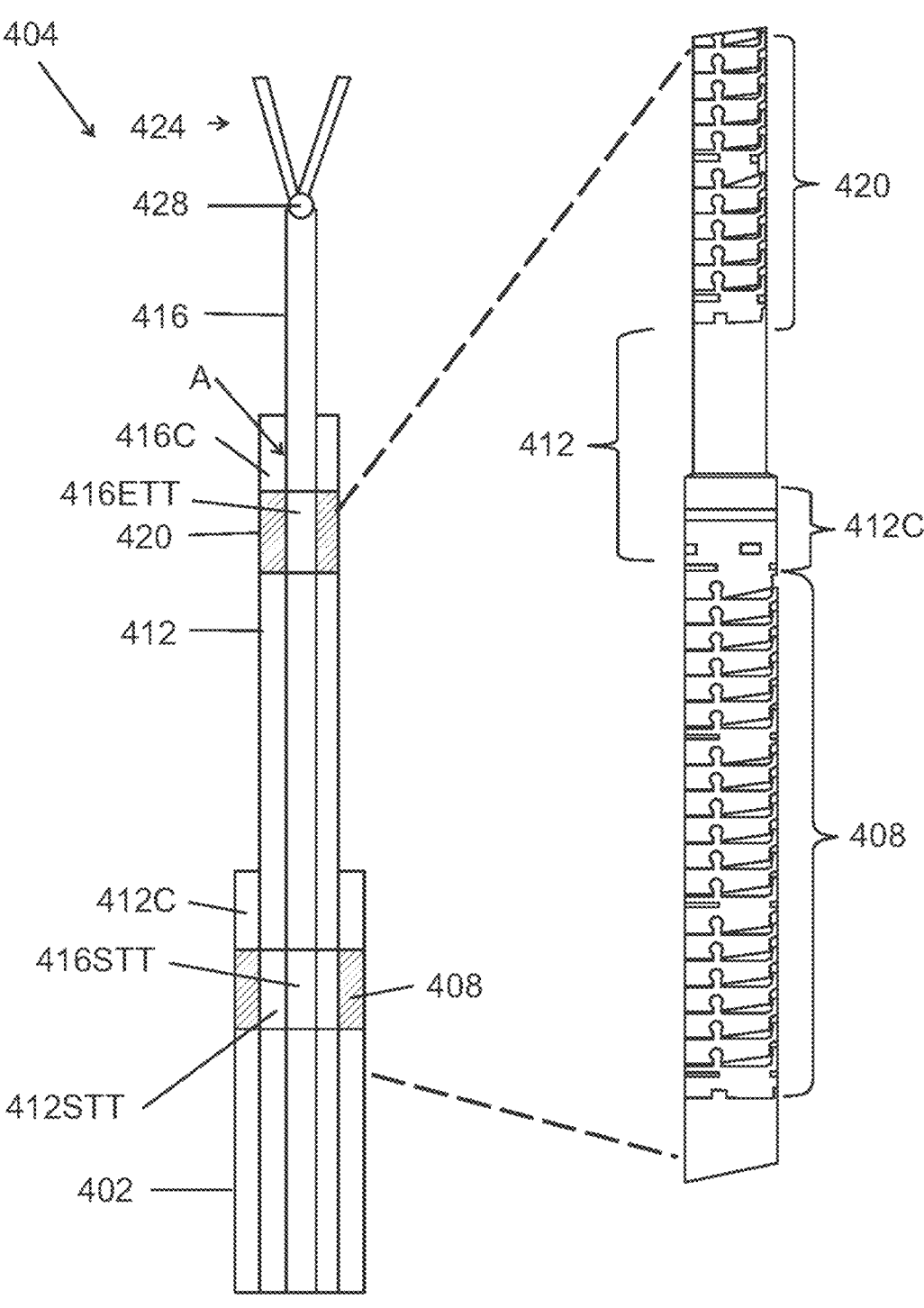
FIG. 4A is a simplified schematic cross sectional view of an arm with nested segment extensions, according to some embodiments of the invention.
FIG. 4B is a simplified schematic of a side view of a portion of an arm, according to some embodiments of the invention.

FIG. 4A is a simplified schematic cross sectional view of an arm 404 with nested segment extensions, according to some embodiments of the invention. FIG. 4B is a simplified schematic of a side view of a portion of an arm, according to some embodiments of the invention. Dashed lines illustrate the portion of the arm illustrated in FIG. 4A illustrated by FIG. 4B.

In some embodiments, arm 404 includes a hand tool 424 coupled to a radius 416 at a wrist joint 428.

In some embodiments, radius 416 is coupled to a radius extension including two torque transfer portions; an elbow torque transfer portion 416ETT disposed inside an elbow joint 420 and a shoulder torque transfer portion 416STT disposed inside a shoulder joint 408. In some embodiments, radius 416 is coupled to a humerus 412 by a connector 416C. In some embodiments, portion 416C connects radius 416 to humerus 412 whilst allowing free rotation of humerus 412. In some embodiments, at region A of FIG. 4A, protrusion/s on radius portion 416 fit into indentation/s on portion 416C. In an exemplary embodiment, a ring shaped protrusion on radius portion 416 (e.g. a ring of material connected (e.g. welded) to radius portion 416) fits into an indentation on portion 416C. Similarly, in some embodiments, portions 412C and 412 are connected by matching protrusion/s and indentation/s (e.g. a ring protrusion on portion 412 fitting into a matching indention in portion 412C).

In some embodiments, a "connecting section" includes a connector and a joint, for example shoulder joint 408 and connector 412C, for example elbow joint 420 and connector 416C.

In some embodiments, hand tool 424 is actuated (e.g. opened and/or closed) by rotation of a hand tool extension (not illustrated). In some embodiments, the hand tool extension includes one or more torque transfer portion. In some embodiments, the hand tool portion is nested in a center of the surgical arm. Alternatively or additionally, in some embodiments, a hand tool is actuated by changing tension on one or more elongated element coupled to portion/s of the hand tool.

Figure 4C:
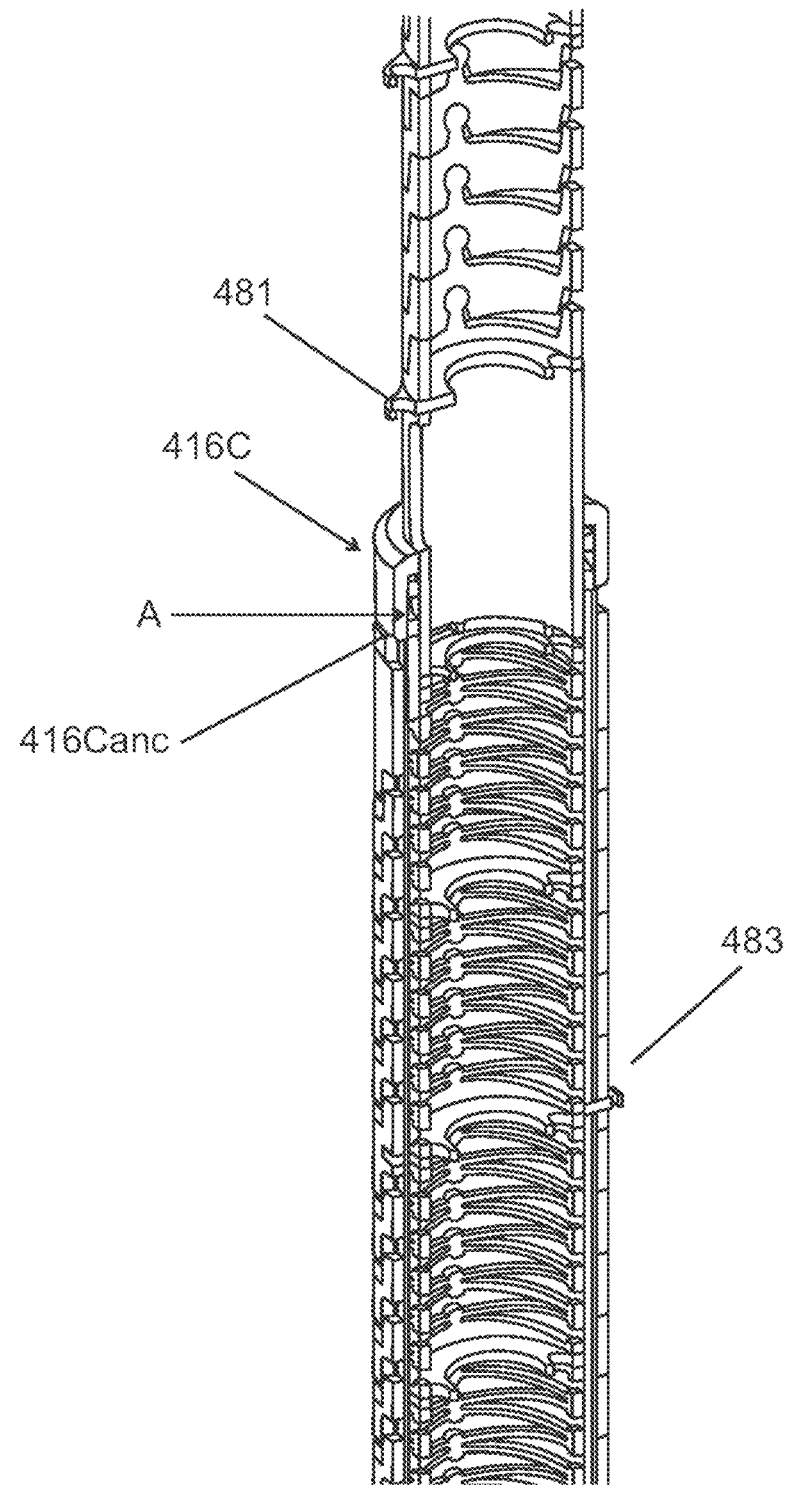
FIG. 4C is a simplified schematic cross sectional view of an arm with nested segment extensions, according to some embodiments of the invention.

FIG. 4C is a simplified schematic cross sectional view of a portion of an arm, according to some embodiments of the invention. In some embodiments, for example, a portion includes a ring protrusion which fits into an indentation on portion 416C.

In some embodiments, portion 416C provides anchoring to one or more elongated element: for example, where elongated element/s (e.g. a cable, a wire, a tape) are connected/coupled to portion 416Canc.

In some embodiments, one or more connector couples portions whilst allowing one portion to rotate within the connector about the portion's long axis. For example connecting portion 416C allows radius 416 to rotate within connecting portion 416C about a radius long axis.

In some embodiments, humerus 412 is coupled to a humerus extension including one torque transfer portion, a shoulder torque transfer portion 412STT disposed inside shoulder joint 408. In some embodiments, the humerus is coupled to a torso 402 by a connector 412C.

In some embodiments, a surgical arm includes a first and a section flexible portion (e.g. elbow joint and shoulder joint) which are coupled together with a short connecting segment (e.g. a humerus section coupling a shoulder and elbow joint is short). In some embodiments, coupling between the flexible portions is a point connection (e.g. a shoulder and elbow joint are directly connected).

In some embodiments, a rigid anchoring portion (e.g. portion 416C) connects two flexible portions, where the anchoring portion provides anchoring of elongated elements which control flexion and extension of the joint which is, for example, proximal to the elongated portion. In some embodiments, anchoring is provided by a portion of one of the joints, e.g. a distal portion of the proximal joint.

In some embodiments, one or more shafts (or portions thereof) of the surgical arm are rigid. In some embodiments, a flexible shaft is nested within a rigid outer shaft.

In some embodiments, the outer shaft is flexible to a lower extent than the inner shaft.

FIG. 5A is a flowchart of a method of constructing a modular system in accordance with a surgical approach, according to some embodiments of the invention.

In some embodiments, a surgeon (and/or other clinical personnel) decide on a surgical approach (500a). In some embodiments, one or more incisions are made to provide access to the target tissue. Additionally or alternatively, access to the target tissue is obtained via a natural body orifice, such through vaginal and/or anal and/or oral orifices. In some embodiments, a port (such as 212, FIG. 2A) is inserted and/or coupled to the natural orifice and/or to the incision. Potentially, the port prevents and/or reduces movement with respect to the patient of (e.g. supporting portions) of tools inserted through it. Optionally, in some embodiments, the port is coupled to a portion of the system, for example, a patient support surface.

In some embodiments, the target tissue is approached via a combination of one or more incisions with entry via one or more natural orifices.

In some embodiments, the surgical device is constructed in accordance with the selected surgical approach (502a). In some embodiments, the device is constructed by coupling one more modular units to each other, for example coupling 2, 3, 5, 6 or intermediate or larger number of modular units together. In some embodiments, a modular unit comprises an arm coupled to a motor unit which is configured for actuating articulation of the arm. Additionally or alternatively, a modular unit comprises any combination of arms and/or motor units which make up an independent assembly, configured to be used alone as well as with additional modular units.

In some embodiments, the constructed device comprises multiple sets (e.g. 2, 3, 4, 6) of arms coupled to respective motor units that are attached together, for example so that the device comprises 3 arms actuated by 3 corresponding motor units, arms actuated by 5 corresponding motor units, etc. Additionally or alternatively, more than one arm (e.g. 2, 3, 5 arms) are configured to be actuated by a single motor unit.

Additionally or alternatively, more than one motor unit actuates a single arm. For example, in some embodiments, an arm has and/or is coupled to an arm base. In some embodiments, an arm base includes a motor unit. In some embodiments, more than one arm is coupled to a single arm base which arm base includes one or more motor units.

In some embodiments, the modular units are configured to connect to each other by a mechanical attachment. In some embodiments, the mechanical attachment comprises one or more elements configured on a housing of a motor unit, for example a protrusion on a first motor unit received in respective indentation on a second motor unit, a connector which concurrently fits into a plurality of indentations on different motor units, an interference fit coupling, a slide fit coupling, and/or other attachment configurations.

In an exemplary embodiment, attachment between two motor units includes slide attachment where a protrusion on a first motor unit is sized and/or shaped to fit into a slot on a second motor unit. In some embodiments, a depth of the slot decreases along a length of the slot towards a step where the depth of the slot decreases (e.g. abruptly, e.g. in a step). In some embodiments, a spring loaded latch on the first motor unit protrusion prevents the motors units from sliding apart, once the protrusion is slid into the slot.

Additionally or alternatively, the motor units are connected to each other via electromagnetic means, such as electromagnetic locks. Optionally, an electromagnet portion of the lock is coupled to a housing of a first motor unit, and a mating armature is coupled to a housing of a second motor unit. In some embodiments, the electromagnetic lock is used for identifying whether another motor unit was attached.

Alternatively, constructing comprises decoupling modular units previously attached to each other, for example by a quick release mechanism. In some embodiments, the quick release mechanism comprises unfastening a latch, for example to release a mechanical coupling between the motor units. In some embodiments, the quick release mechanism comprises pressing a button and/or switch to deactivate an electromagnetic coupling. In some embodiments, constructing comprises coupling a linear unit, for example unit 290 as shown in FIG. 2B, to one or more of the motor units.

In some embodiments, a number and/or structure of modular units from which the device is constructed is selected in accordance with the selected surgical approach.

In some embodiments, the number of arms is selected so that each of the arms is inserted through an opening to the body (e.g. through an incision and/or through a natural orifice). Additionally or alternatively, the number of arms is selected so that more than one arm is inserted through an opening, for example two arms are inserted through the vagina. Additionally or alternatively, the number of units is selected so that one or more arms are configured to be inserted through a first opening and then moved to additional one or more openings.

In some embodiments, the number of arms is selected in accordance with the number of tools required for performing the operation. In an example, 3 end tools such as a camera, graspers and suction/irrigation are operated by, for example, 3 arms.

In some embodiments, construction of the motor construct is performed during set up of the procedure. Optionally, construction is performed in the operation room before and/or after the patient enters the room. In some embodiments, construction or deconstruction of the motor construct is performed during the procedure, for example when changing a surgical approach, such as changing from a single port procedure to a multi-port procedure or vice versa.

In some embodiments, for example, during the procedure (e.g. a surgical procedure) a surgical arm is replaced and/or removed from a surgical area. For example, in some embodiments, a modular surgical arm is detached and/or removed from a motor unit. Optionally, in some embodiments, before the surgical arm is removed from a motor unit, it is retracted from a surgical zone within a patient and/or removed from the patient's body, optionally, while other arm/s remain in situ and/or are employed. In some embodiments, a surgical arm is removed from a first motor unit and attached to a second motor unit, with and/or without retracting the arm from the patient. In some embodiments, a surgical arm is removed from a motor arm and is replaced with a second surgical arm which is attached to the motor unit, optionally without moving and/or retracting the motor unit from an initial position.

In some embodiments, a surgical arm tool is removed and/or replaced and/or moved to a different surgical arm. For example, in some embodiments, optionally, during a procedure, optionally when arm/s remain inside a patient, a surgical arm tool is removed from a surgical arm. In some embodiments, the tool is then moved and attached to a second surgical arm. In some embodiments, the tool is replaced with a second tool which is then attached to the arm.

In some embodiments, when an arm is removed and/or moved and/or replaced, a user enters into an input device an identifier of, for example, the arm/s and/or motor units involved and/or an indication of the action taking place, for example, removal and/or replacement and/or moving to a different motor unit. In some embodiments, an arm includes a physical identifier, e.g. an RFID tag, a barcode which, in some embodiments, is scanned by a reader in, for example, one or more of a user interface and/or motor unit. In some embodiments, a signal providing identifier/s of the arm/s involved and/or of the motor unit/s involved is sent by the motor unit and/or sensors in the arm and/or by an external sensor (e.g. RFID reader) to a processor which, in some embodiments, stores the identifiers in a memory. In some embodiments, the processor and/or memory are located at a control console.

Additionally or alternatively, in some embodiments, when a tool is removed and/or moved and/or replaced a user enters into an input device an identifier of, for example, the tool/s, arm/s and/or motor units involved and/or an indication of the action taking place, for example, removal and/or replacement and/or moving to a different surgical arm. In some embodiments, a tool includes a physical identifier, e.g. an RFID tag, a barcode which, in some embodiments, is scanned by a reader in, for example, one or more of a user interface and/or motor unit. In some embodiments, a signal providing identifier/s of the tool/s and/or arm/s involved and/or of the motor unit/s involved is sent by the motor unit and/or sensors in the arm and/or by an external sensor (e.g.

RFID reader) to a processor which, in some embodiments, stores the identifiers in a memory.

In some embodiments, the processor and/or memory are located at a control console.

In some embodiments, the one or more arms are inserted into the body through the one or more openings, optionally via one or more entrance ports configured at the one or more openings (504*a*).

In some embodiments, the arms are activated to perform the surgical procedure (506*a*). In some embodiments, mechanical arm movement is directed by a user's (e.g. surgeon) arm movement, optionally via an input device.

In some embodiments, each motor unit is connected (via a wired or wireless connection) to a different communication port in the device controller. In some embodiments, the device controller is configured to recognize the number of arms attached. In some embodiments, the device controller is configured to automatically assign arm pairs, for example defining left and right arms. Additionally or alternatively, the device controller receives an arm pair assignment from the user. Optionally, the assignment is changed in real time (e.g. right arm is redefined as left arm, and vice versa). For example, a user changes selected surgical arms by pausing control (e.g. control of movement of surgical device arm/s by mapped input object movement) of one or more selected surgical device arm and re-selecting one or more surgical device arm. In some embodiments, the user pauses and re-selects arms to switch control of a first device arm by a left user arm and control of a second device arm to control of the second device arm with the user right arm and control of the second device arm by a user left arm.

In some embodiments, a user pauses an initial surgical device arm in a desired position (e.g. to hold user anatomy in position) and selects another surgical device arm (e.g. a third arm) for continued two-arm movement.

In some embodiments, the device control recognizes a current device structure (e.g. number of arms, left and right assigning of arms, a current posture of each arm) by identifying one or more driver circuits of a motor unit actuating an arm.

In some embodiments, the device controller is configured for cross-control of a plurality arms, for example, two arms can be activated or deactivated by a single safety switch. In some embodiments, cross-control is provided via the user input device. In an example, a single activation (e.g. pushing once) of a button on the input device imitating the right arm and/or on the input device imitating the left arm is configured to deactivate both surgical arms; recurrent activation (e.g. a pushing the button twice) is configured to deactivate the respective arm only (e.g. right surgical arm or left surgical arm).

Optionally, a structure of the device is modified during operation (508*a*).

Optionally, the structure is modified in accordance with the surgical approach, for example, if a first stage of the surgery is performed via a plurality of openings (e.g. incisions and/or natural orifices) and a second stage of the surgery is performed via a single opening, one or more modular units are attached for the first stage and separated for the second stage.

Figure 5B:
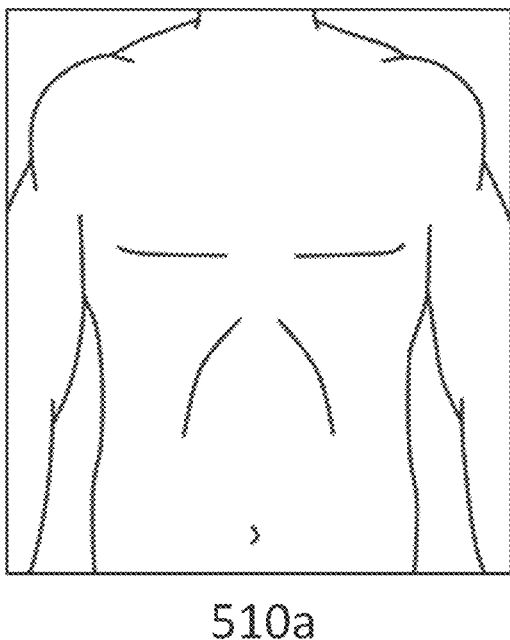
FIG. 5B illustrates exemplary surgical approaches, according to some embodiments of the invention.
Figure 5B:
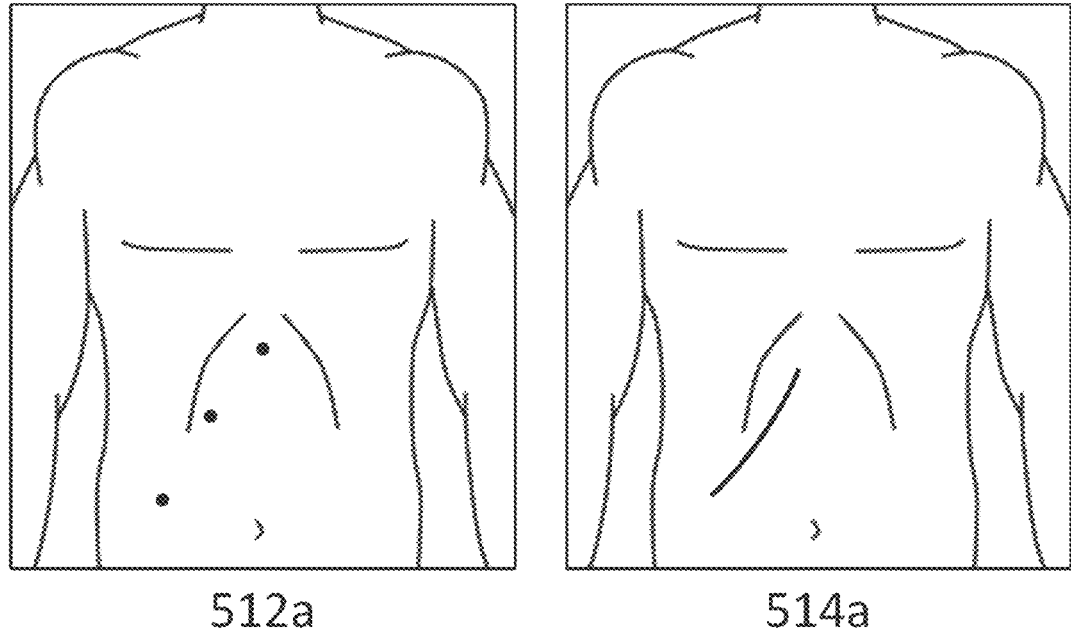

FIG. 5B illustrates exemplary surgical approaches, according to some embodiments. In some embodiments, a single incision is made, for example a single umbilical incision as shown in 510*a*. In some embodiments, multiple incisions are made, for example as shown in 512*a*. For example, in some embodiments, a first device arm is inserted through a first incision and a second device arm is inserted in a second incision. In some embodiments, the device is inserted through a single incision and additional tools, for example a tool for inflation of the abdominal cavity are inserted through one or more separate incision.

In some embodiments, the one or more device arms are inserted through an incision without having to enlarge the incision. In some embodiments, for example as shown in 514*a*, an incision larger than necessary for insertion for the device is made. For example, the largest extent of the incision on the skin surface is larger than 1 cm or more, or 2 cm or more, or 10 cm or more, or 20 cm or more. In some embodiments, the device is used where at least a portion of the inserted device and/or portion of the device under a skin level is visible to a user. Optionally, e.g. when the device is at least partially visible, the system lacks an imager inserted into the body and/or images are not displayed to the user.

Figure 5C:
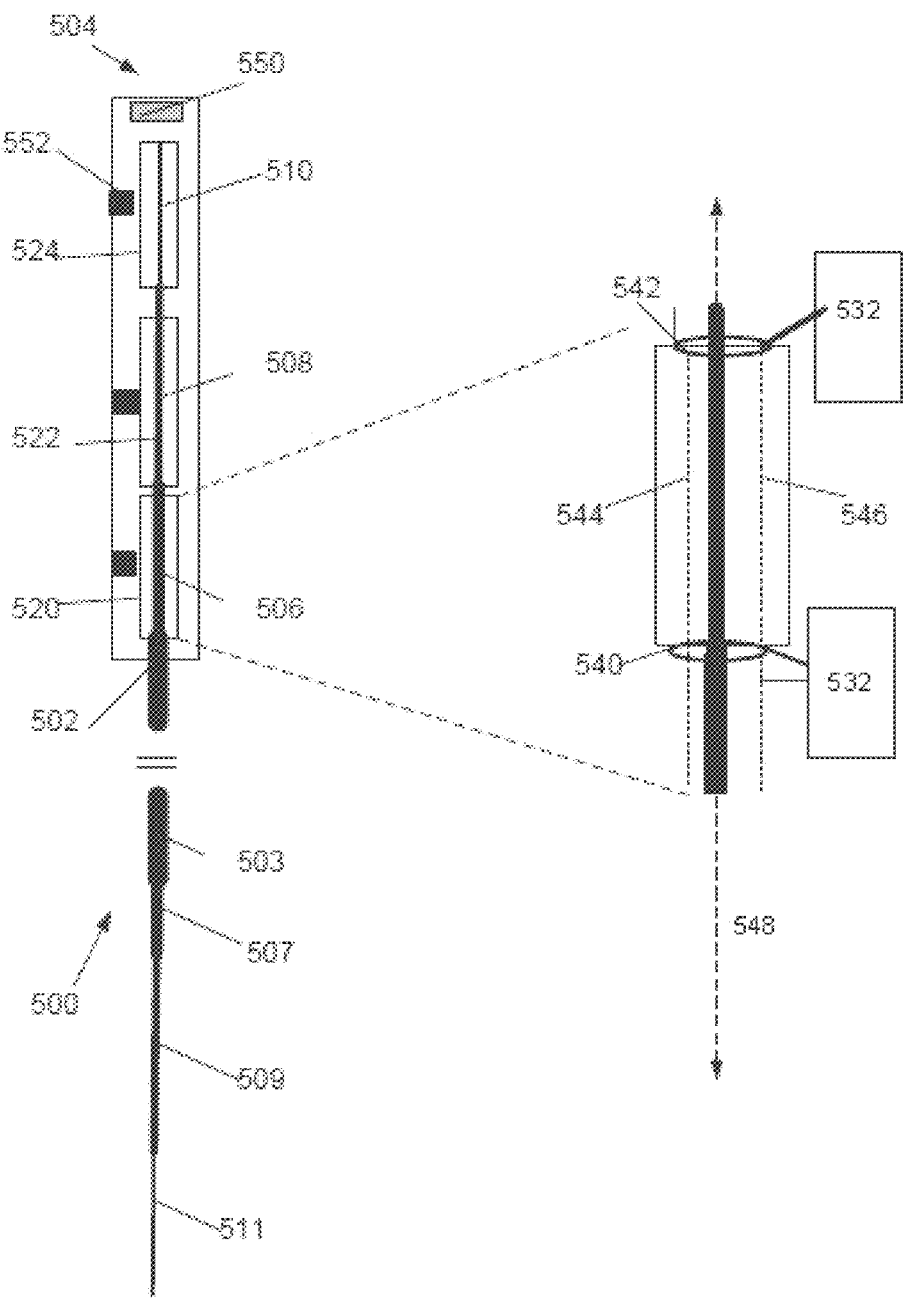
FIG. 5C is a schematic diagram of actuation of a surgical arm, according to some embodiments of the invention.

FIG. 5C schematically illustrates actuation of a surgical arm 500, according to some embodiments.

In some embodiments, a proximally extending shaft extension 502 (e.g. an extension of a torso 503) of arm 500 is attached to a motor unit 504. In some embodiments, proximal shaft extensions of arm segments that are nested within extension 502 (e.g. a proximal shaft extension 506 of humerus 507, a proximal shaft extension 508 of radius 509 that is nested within humerus extension 506, a proximal shaft extension 510 of a hand portion 511 that is nested within radius extension 508, and so forth) are actuated by a plurality of actuation mechanisms of the motor unit, such as 3 actuation mechanisms 520, 522 and 524. In some embodiments, the number of actuation mechanisms is set in accordance with the number of joints of the arm, for example, as shown herein, an arm including 3 joints (e.g. shoulder, elbow and wrist joints) is actuated by 3 actuation mechanisms, an arm including 4 joints is actuated by 4 actuation mechanisms, an arm including 2 joints is actuated by 2 actuation mechanisms, an arm including 1 joint is actuated by a single actuation mechanism.

In some embodiments, an actuation mechanism 520 (shown in the enlarged view) is configured to move at least a segment of arm 500, for example rotate the segment and/or bend the segment and/or otherwise move the segment. In some embodiments, an actuation mechanism comprises one or more actuators, for example 1, 2, 3, 4, 5 and/or 6 actuators. In some embodiments, the actuators are independently operable, yet, in some embodiments, a shaft manipulation (e.g. rotation, bending) obtained by a first actuator effects control of one or more other actuators.

In some embodiments, actuators of the same actuation mechanism are actuated together. Additionally or alternatively, actuators of different actuation mechanisms are actuated together, for example to provide for articulation of a proximal arm segment, a distal arm segment (which is at least partially nested within the proximal arm segment) needs to be moved as well. In an example, to provide for flexion of the shoulder, a bending actuator of an elbow is actuated as well.

In some embodiments, for example as shown herein, shaft extensions 502 and 506 (which is nested, in part, within shaft extension 502) are received within actuation mechanism 520. In some embodiments, actuation mechanism 520 comprises a first actuator 540, and a second actuator 542. In some embodiments, first actuator 540 is configured to rotate an arm portion, such as rotate the torso by rotating shaft extension 502 around its axis. In some embodiments, second actuator 542 is configured to bend an arm portion, such as bend a shoulder joint at a distal end of the torso (not shown herein). Optionally, bending is achieved by respective linear movement of elongate elements 544 and 546, which extend from actuator 542 and are connected distally to the joint.

In some embodiments, a prime mover of an actuator such as 540 and/or 542 comprises a motor 532. In some embodiments, a speed of motor 532 ranges between, for example, 10-100 rpm, such as 20 rpm, 50 rpm, 70 rpm, 80 rpm or intermediate, higher or lower speeds. In some embodiments, motor 532 is configured to apply a torque between 0.5 N*M to 3 N*m, such as 1 N*m, 1.5 N*m, 2 N*m or intermediate, higher or lower values. In some embodiments, motor 532 is a continuous rotation motor.

Additionally or alternatively, a prime mover of an actuator comprises a linear motor. Additionally or alternatively, a prime mover of an actuator comprises a pulley.

In some embodiments, the prime mover of an actuator is manually operated, for example comprising one or more cables that are pulled on to actuate movement of the gear.

In some embodiments, a single motor is configured to move more than one actuator (e.g. rotate both the bending and rotation gears). In some embodiments, dual-actuation is enabled by use of a locking mechanism and another motor configured for switching between the actuators, based on the selected articulation (e.g. bending or rotation).

In some embodiments, motor 532 is positioned parallel to the shaft extension, for example underlying the shaft extension, overlying the extension and/or positioned beside the extension. Alternatively, motor 532 is disposed within an internal lumen of the shaft extension. Alternatively, the shaft extension is configured as a part of the motor, for example contained within an external housing of motor 532.

In some embodiments, an actuator comprises a single gear or a gear train. In some embodiments, the gear train is configured to amplify the input torque generated by motor 532. Alternatively, the gear train is configured to reduce the input torque generated by motor 532. In some embodiments, the gear train is configured to reduce the rotation speed generated by the motor. In an example, the motor speed is 12,000 RPM, and the gear or gear train reduce the speed by a ratio of, for example, 134:1, 43:1, 9:1 and/or intermediate, higher or lower ratios. In an example, a gear or gear train actuating movement of an end-effecter of the arm such as grippers is configured to reduce the speed by a ratio of 9:1, enabling fast opening and closure of the gripper. This may be advantageous, for example, when dissecting tissue using the gripper.

Alternatively, in some embodiments, the gear train is configured to increase the output speed generated by the motor. In an example, the output speed of the motor is increased for autonomous electrical ablation of tissue.

In some embodiments, actuators of an actuation mechanism comprise gears or gear trains that are different from each other. In some embodiments, the motors of the two actuators are rotated at similar speeds, but the "final" movement manipulating gears of each actuator are rotated at different speeds. In an example, actuator 542 comprises a gear transmission while actuator 540 is driven directly by the motor. In another example, the actuators each comprise a single gear, but the gears are of different sizes and/or shapes (e.g. comprising different number of teeth).

In an example, actuator 540 comprises a gear that is configured to rotate shaft extension 502 directly, rotating at a speed, of, for example, 2000 RPM; actuator 542 comprises a gear that is configured to actuate bending by linearly moving elongated elements 544 and 546, optionally by rotation of a threaded screw coupled to the elements for example as described hereinbelow, and due to this additional transmission the gear of actuator 542 needs to rotated faster than gear 540, for example rotated at a speed of 4000 RPM.

In another example, an actuator that actuates an end-effecter such as a gripper is configured to rotate at a relatively fast speed, for example 9000 RPM for enabling fast movement.

Alternatively, in some embodiments, it is desired to actuate an end-effecter at a relatively low speed, for example for action requiring applying of relatively large force via the end-effecter, such as separating tissue, stapling tissue, and/or other actions.

In some embodiments, actuators 540 and 542 are rotated on a single rotational axis 548. In some embodiments, axis 548 is also the rotational axis of shaft extensions 502 and 506.

In some embodiments, actuation mechanisms 520, 522, 524 of the motor unit are collinear.

In some embodiments, the motor unit includes one or more position sensor 552.

In some embodiments, position sensor 552 is placed adjacent the motor for sensing a current rotation angle of the motor.

In some embodiments, the position sensor is magnetically operated, using a magnet placed on the motor gear and sensing the magnetic flux to determine a current position of the motor gear.

In some embodiments, the motor unit is controlled by a processor 550 including a memory which stores commands.

In some embodiments, data from position sensor/s and/or from control memory is used to infer a position of device portion/s.

In some embodiments, the motor unit is controlled by a processor configured in the user's input device.

Figure 29:
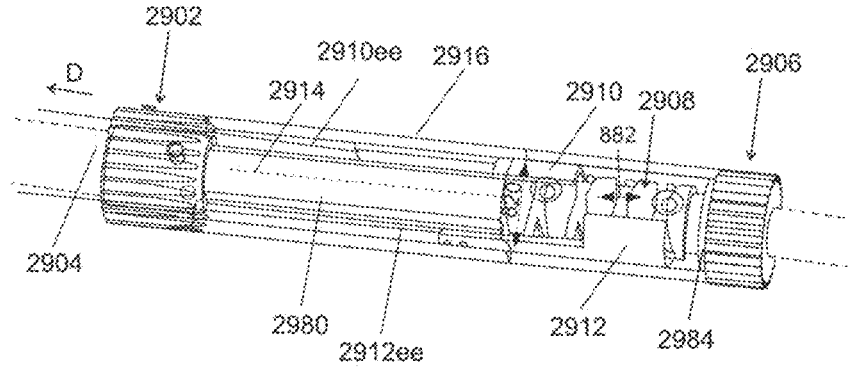
FIG. 29 is a simplified schematic side view of an actuation mechanism for control of a surgical arm joint, according to some embodiments of the invention.

FIG. 29 is a simplified schematic side view of an actuation mechanism for control of a surgical arm joint, according to some embodiments of the invention.

In some embodiments, a rotation gear 2902 is coupled to a shaft 2904, where shaft 2904 is coupled to an extension (e.g. to torso 402, FIG. 4A). In some embodiments, rotation of rotation gear 2902 causes rotation of shaft 2904 which in turn rotates the distal extension coupled to the shaft.

In some embodiments, a shaft 2980 which is nested, at least in part, within shaft 2904 extends in the proximal direction to a bending gear 2906.

In some embodiments, bending gear 2906 is coupled to a portion including screw threading, referred to herein as threaded screw 2908. In some embodiments, a threading on screw 808 comprises a double thread. In some embodiments, rotation of the double thread in one direction achieves bidirectional lateral movement of one or more rider elements, such as half-nuts referred to hereinbelow, coupled to the screw.

In some embodiments, a pitch 882 of the screw thread is selected according to the use of the arm. For example, a small thread pitch is more advantageous when the arm is configured to operate large loads, for example a load of 2000 grams, 1500 grams, 3000 grams or intermediate, larger or smaller loads at a low speed (e.g. 0.5 rounds per second, 1 round per second, 0.2 rounds per second). Alternatively, a large thread pitch is more advantageous when the arm is configured to operate small loads, for example 100 grams, 50 grams, 300 grams or intermediate, larger or smaller loads at a higher speed (e.g. 2.5 rounds per second, 4 rounds per second, 5 rounds per second).

In some embodiments, rotation of the bending gear 2906 causes rotation of threaded screw 2908. In some embodiments, a first half nut 2910 and a second half nut 2912 are coupled to screw threaded screw 2908 such that rotation of the screw threading generates linear movement of half-nuts parallel to a long axis 2914 of central shaft 2904, where first half-nut 2910 and second half-nut 2912 move in different directions.

In some embodiments, each of the half-nuts is limited to movement in a single direction, for example a right handed half-nut and a left handed half-nut. In some embodiments, movement of the half-nuts is limited by one or more protrusions, for example protrusions extending radially inward from an inner wall of housing 2916, for example as further described herein.

In some embodiments, first half nut 2910 and second half nut 2912 are connected to elongated elements 2910ee and 2912ee respectively, where linear movement of the nuts pulls one elongated element whilst releasing and/or pushing on the other, generating flexion/extension of the joint. In some embodiments, a distance 820 between the half-nuts, measured along an axis perpendicular to the long axis, defines the distance between the elongated elements. In some embodiments, distance 820 between the elongated elements remains constant. In some embodiments, first nut 2910 is configured remain in line with elongated element 2910ee, and second nut 2912 is configured to remain in line with elongated element 2912ee.

In some embodiments, an elongated element such as 2910ee and/or 2912ee comprises a wire, cable, ribbon, tape and/or any other element which can be tensioned and released to provide for bending of the joint.

It is noted that in some embodiments, only one elongated element is used. In an example, the mechanism comprises one elongated element and an elastic element such as a spring. Optionally, the spring is configured to move relatively to the elongated element, for example if the elongated element is flexed, the spring is extended and vice versa. It is also noted that in some embodiments, more than two elongated elements (e.g. 3, 4, 6, 8) may be used.

In some embodiments, actuation of the rotation gear rotates the arm segment and thereby pulls on the elongated elements, moving the half-nuts. If the bending gear is held stationary (e.g. by the motor gear), the threaded screw will not rotate, generating simultaneous rotation and bending of the arm segment. If the bending gear is free to rotate, pulling on the elongated elements will in turn move the half-nuts, rotating the threaded screw. Friction at interface 2984 between a head of the threaded screw and bending gear 2906 will in turn rotate the bending gear, generating rotation of the arm segment as one piece.

In some embodiments, one or both of the elongated elements is coupled to an elastic element such as a spring. Optionally, the spring is configured to limit tensioning of the elongated element(s), yielding in response to a force (e.g. torque and/or pulling force) above a certain threshold.

Figure 6A:
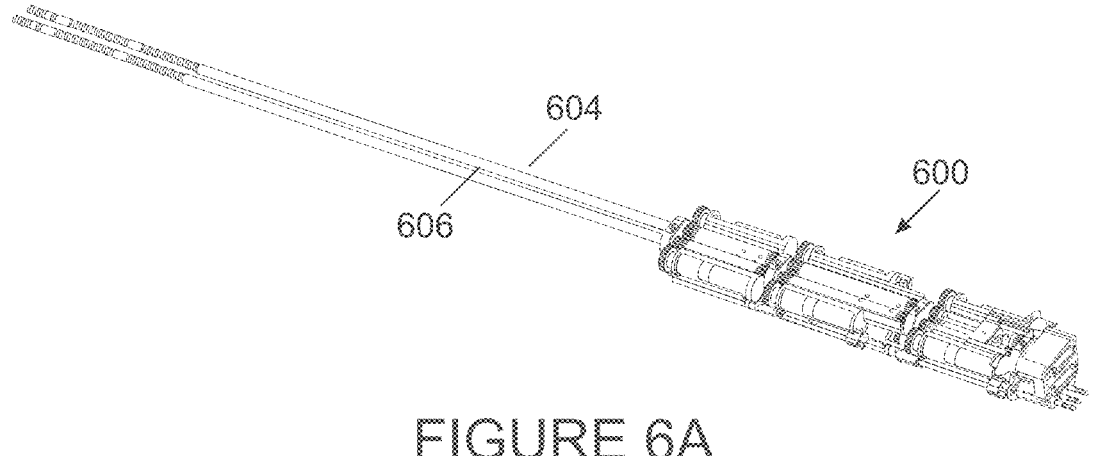
FIGS. 6A-6D are various views of a motor construct for actuating a surgical arm, according to some embodiments of the invention.

FIG. 6A is a simplified schematic side view of a motor construct 600 for actuation of a device including surgical arms, according to some embodiments of the invention. As referred to in FIGS. 6A-6D, motor construct 600 is comprised of two modular units, each comprising a motor unit coupled to an arm and configured for actuating movement of the arm, according to some embodiments.

Figure 6B:
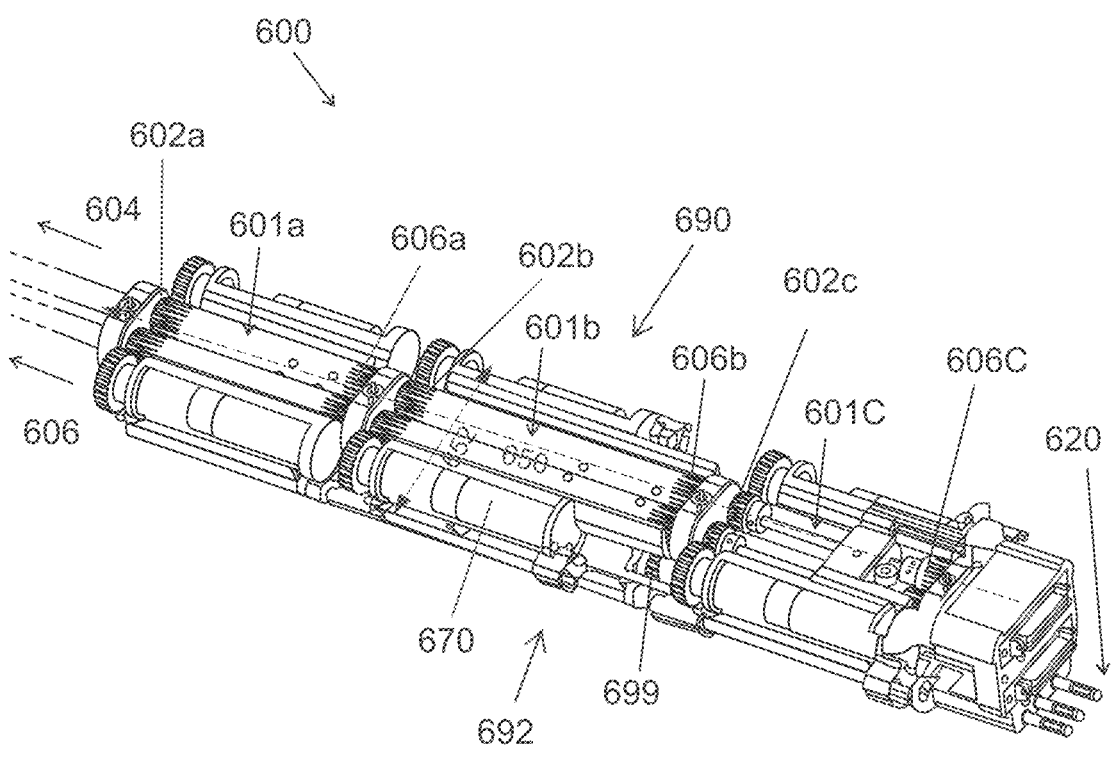

In some embodiments, a device including a first surgical arm 604 and a second surgical arm 606 are controlled by motor construct 600. FIG. 6B is a detailed view of motor construct 600, according to some embodiments.

In some embodiments, a first motor unit 690 configured for actuating arm 604 comprises, for example, 3 actuation mechanisms 601a, 601b, 601c. In some embodiments, similarly, second surgical arm 606 is actuated by a motor unit 692 comprising three actuation mechanisms. Optionally, the motor units are parallel to each other. Optionally, the motor units are arranged such that the actuation mechanisms are symmetrically arranged along a long axis 650 of motor construct 600.

In some embodiments, a first actuation mechanism 601a, including first rotation gear 602a and first bending gear 606a, drives flexion/extension and rotation of a shoulder joint. Referring now to FIGS. 4A-4B, for example, in some embodiments, first actuation mechanism 601a rotates the shoulder joint by rotating torso 402 and effects flexion and extension of shoulder joint 408 by movement of elongated elements attached to connector 412C.

In some embodiments, a second actuation mechanism 601b, including second rotation gear 602b and second bending gear 606b, drives flexion/extension and rotation of an elbow joint. In some embodiments, one or more driving gear coupled to a motor 670 is disposed underneath the motor unit 690. For example, in some embodiments, a gear which drives second bending gear 606b, which gear is coupled to a motor is disposed on an underside of the motor unit 690. For example, gear 699 drives a second actuation mechanism corresponding to second surgical arm 606.

Referring now to FIGS. 4A-4B, for example, in some embodiments, second actuation mechanism 601b rotates the elbow joint by rotating humerus 412 and effects flexion and extension of elbow joint 420 by movement of elongated elements attached to portion 416C.

In some embodiments, a third actuation mechanism 601c, including third rotation gear 602c and third bending gear 606c, actuates an end effecter (e.g. opens and closes a gripper) and drives rotation of a wrist joint. Referring to FIG. 4A, in some embodiments, rotation gear 602c rotates radius 416 and bending gear 606c actuates hand tool 424; For example, in some embodiments, rotation of third bending gear 606c opens and closes an end effecter.

In some embodiments, similarly, second surgical arm 606 is actuated by three actuation mechanisms, including, for example, 6 motors. In an exemplary embodiment, for example as shown herein, a device for insertion into the body includes two surgical arms, actuated by 12 motors.

In some embodiments, one or more additional motor (e.g. a 13th motor) moves the device arms towards and/or away from the motor unit. For example, in some embodiments, a position of attachment of the motor unit (e.g. to a support and/or to a patient support surface) is changed e.g. by a motor.

In some embodiments, the device comprises a single arm actuated by a motor unit comprising 6 motors (e.g. 2 motors per each actuation mechanism). In some embodiments, a $7^{th}$ motor is used for linearly moving the arm, for example towards and/or away from the motor unit and/or from the patient's body. In some embodiments, one or more additional motors (e.g. an $8^{th}$ motor, a $9^{th}$ motor) are used. Optionally, the additional motor(s) actuate movement of an end-effecter of the arm around a pivot point (fulcrum movement), for example around the incision.

For example, referring to FIGS. 2A-2C, in some embodiments, a position of attachment of support 282 with respect to rail 202 is changed (e.g. by a motor located on support 282). For example, in some embodiments, a position of attachment of motor unit 214 with respect to support 1482 is changed (e.g. by a motor located on support 282).

For example, moving the device into and/or out of a patient body e.g. when the motor unit is supported in a fixed configuration and/or to automate movement of the device into the patient. In some embodiments, a motor located within motor construct 600 moves the device arms into and/or out of a patient.

In some embodiments, for example, so that rotation of a joint also causes rotation of joints distal of the rotated joint, more than one actuation mechanism is driven in rotation of the joint. For example, in some embodiments, for rotation of the shoulder joint, gears 602a, 606a, 602b, 606b, 602c, 606c are rotated in the same direction. For example, in some embodiments, for rotation of the elbow joint, gears 602b, 606b, 602c, 606c are rotated in the same direction. For example, in some embodiments, for rotation of the end effecter, gears 602c, 606c are rotated in the same direction. In some embodiments, concurrent rotation of nested portions with outer portions prevents stress on and/or tangling of internal elongated elements (e.g. elongated element/s which are used to effect flexion/extension, e.g. elongated element/s providing power supply).

In some embodiments, one or more actuation mechanism is used to flex/extend a joint. For example, in some embodiments, to bend a shoulder joint, elongated elements for bending of both the shoulder joint and elbow joint are moved, for example by actuating bending gear 606a and bending gear 606b.

In some embodiments, if elongated elements for the elbow are not moved and/or released, tension in the elongated elements associated with the elbow joint resist movement of the shoulder joint.

In some embodiments, a motor unit is small. In some embodiments, a motor unit comprises a long axis length 650 of between 100-600 mm, or 200-400 mm, or 300-500 mm, or 150-400 mm, or intermediate, longer or shorter length.

In some embodiments, for example as shown herein, a motor construct comprising two parallel arrangements for actuating two arms comprises a width 652 (e.g. as measured perpendicular to the long axis) between 20-100 mm, or 30-80 mm, or mm, or intermediate, longer or shorter size.

In some embodiments, motor 670 is cylindrical. Optionally, a diameter of motor 670 is less than 17 mm, less than 35 mm, less than 10 mm or intermediate, larger or smaller diameters. A potential advantage of disposing a motor of a relatively small diameter in a parallel position relative to the arm may include maintaining the dimensions of the motor unit small.

Alternatively, the motor is not cylindrical, for example rectangular. In some embodiments, the motor comprises a hollow shaft. A potential advantage of a hollow shaft may include reducing the footprint of the system in the operating room.

In some embodiments, electrical power is supplied through wires to the motor units, for example, in some embodiments, contacts 620 are connected to an electrical power supply. The electrical power supply may include a battery (optionally rechargeable) and/or a generator and/or connection to the electrical network via a wall socket and/or a combination thereof. In some embodiments, the power range is between 100-300 W, for example 150W, 200 W, 250 W or intermediate, higher or lower ranges. In some embodiments, an uninterruptible power supply source is used to protect from power interruptions.

In some embodiments, a motor construct drives more than two surgical arms and/or drives additional device elements. For example, in some embodiments, a motor construct drives two device arms and a camera.

Figure 6C:
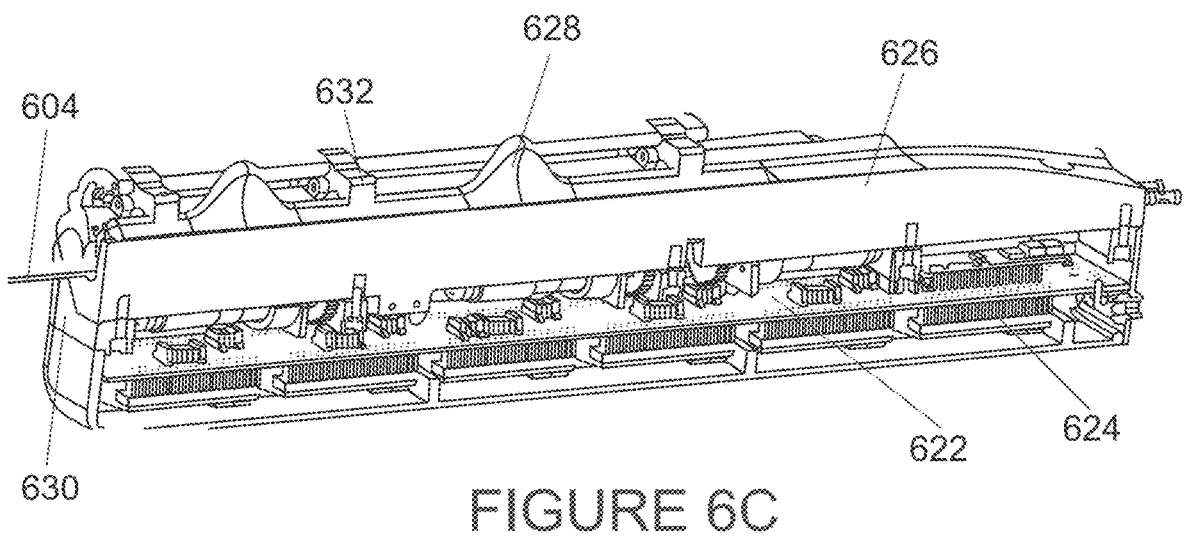

FIG. 6C is a cross-section of the motor construct along the length of the construct, showing first motor unit 690, according to some embodiments.

In some embodiments, the motor unit comprises a motherboard 622, optionally underlying the actuation mechanisms. In some embodiments, one or more driver circuits 624 are operably coupled to motherboard 622 for controlling operation of the motor unit. In some embodiments, each driver circuit is configured to control activation of one of the motors (e.g. one of the 6 motors described hereinabove). In some embodiments, cross-control of the motors is provided. In an example, a position sensor of a first motor is controlled by a controller of a second motor. Optionally, in such configuration, malfunctioning of the first motor can be detected by the controller of the second motor. In some embodiments, malfunction of the first motor is detected by the controller of the second motor.

In some embodiments, an external housing 626 of the motor unit comprises a handle 628 for attaching and/or releasing arm 604 from a distal end face 630 of the motor unit.

In some embodiments, one or more latches 632 are configured on external housing. Optionally, latch 632 is configured to release a gear fixation mechanism used, for example, during attachment of the surgical arm to the motor unit to maintain calibration of the motor unit, for example as further described herein.

Figure 6D:
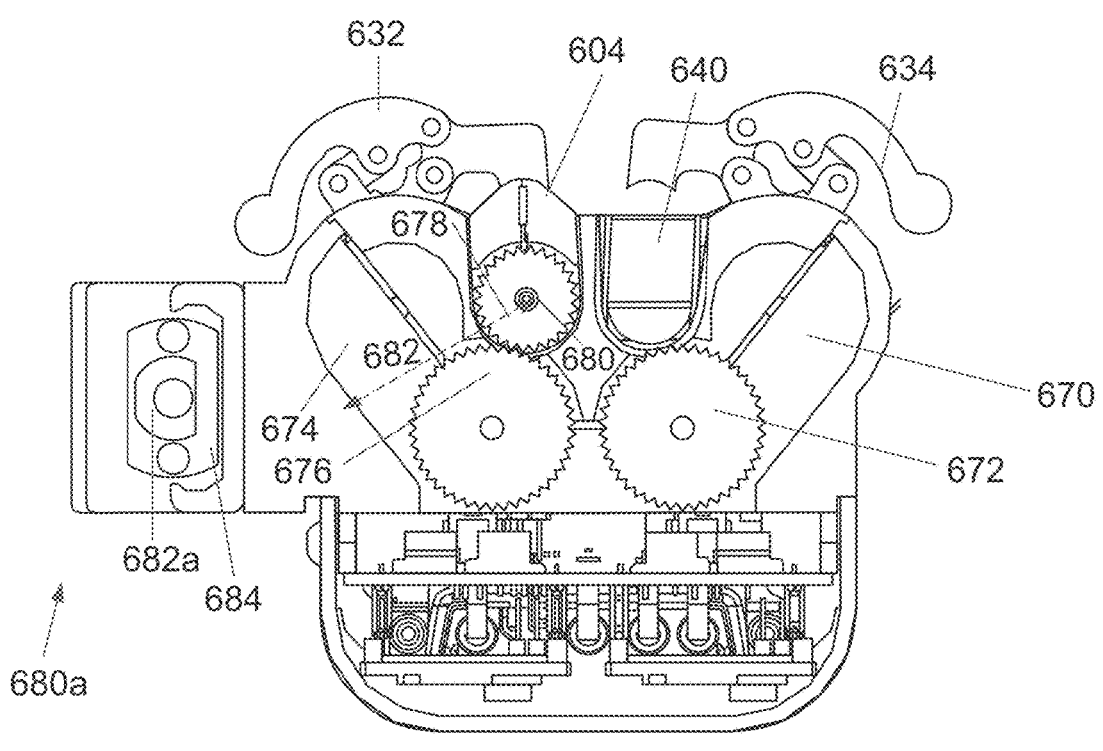

FIG. 6D is a cross section of the motor construct 600 along an axis perpendicular to the long axis, according to some embodiments.

In some embodiments, the motor construct is configured to actuate two surgical arms; in this example, one surgical arm 604 (an extension of which) is shown to be received within the first motor unit 690, while the second opposing motor unit 692 is shown in a configuration suitable for receiving a second arm, for example received within internal lumen 640.

It is noted that in some embodiments a motor unit configured for actuating a single arm is comprised of only of one of the sides of the motor construct shown herein, including, for example, 3 actuation mechanisms.

In some embodiments, for example as shown herein, actuation gears 672 and 676 of motors 670 and 674 respectively are each configured to drive a gear of an actuation mechanism, for example actuation gear 672 of motor 670 is configured to drive rotation gear or bending gear 678 (such as gear 602a or 606a or 602b or 606b or 602c or 606c).

In some embodiments, latch 632 configured at motor unit 690 which, in this illustration, includes the arm, is shown at a closed position. In some embodiments, a closed positioned of the latch releases a fixation mechanism of gear 678, allowing it to rotate freely. As further shown in this figure, a second latch 634 configured at the second motor unit 692 is shown at an open, lifted position.

In some embodiments, a motor such as 674 is disposed such that it does not extend to a distance 682 longer than 5 mm, 10 mm, 20 mm or intermediate, longer or shorter distances relative to a central long axis of an actuation mechanism, for example passing through a center 680 of rotation/bending gear. A potential advantage of a motor disposed adjacent an actuation mechanism, optionally in parallel to the actuation mechanism such that it substantially does not protrude outwardly or protrudes outwardly to a short distance only may include reducing bulkiness of the motor unit, potentially allowing insertion of the surgical arm(s) as well as the motor unit into the body during operation.

In some embodiments, the motor unit is coupled to a linear unit 680a, configured for actuating linear movement of the motor unit (and thereby of the arm(s)), for example actuate advancement and/or retraction of the device to and/or from the patient body. In some embodiments, linear unit 680a comprises a rail 682a on which a sliding element 684 coupled to the motor unit can be moved linearly. In some embodiments, movement (e.g. sliding) of the motor unit on the rail of the linear unit is actuated by a motor.

Alternatively, in some embodiments, the linear unit is an integral component of the motor unit.

In some embodiments, the linear unit comprises one or more sensors, such as microswitches, for detecting movement of the motor unit. In some embodiments, the linear unit comprises one or more actuation buttons configured to provide for a user (e.g. nurse) to move the motor unit according to the need. In some embodiments, the motor driving the linear movement (not shown herein) comprises an electro-magnetic brake. Optionally, the brake is configured to avoid unwanted movement (e.g. slipping) of the motor unit, for example during a power outage.

Figures 31A, 31B, 31C:
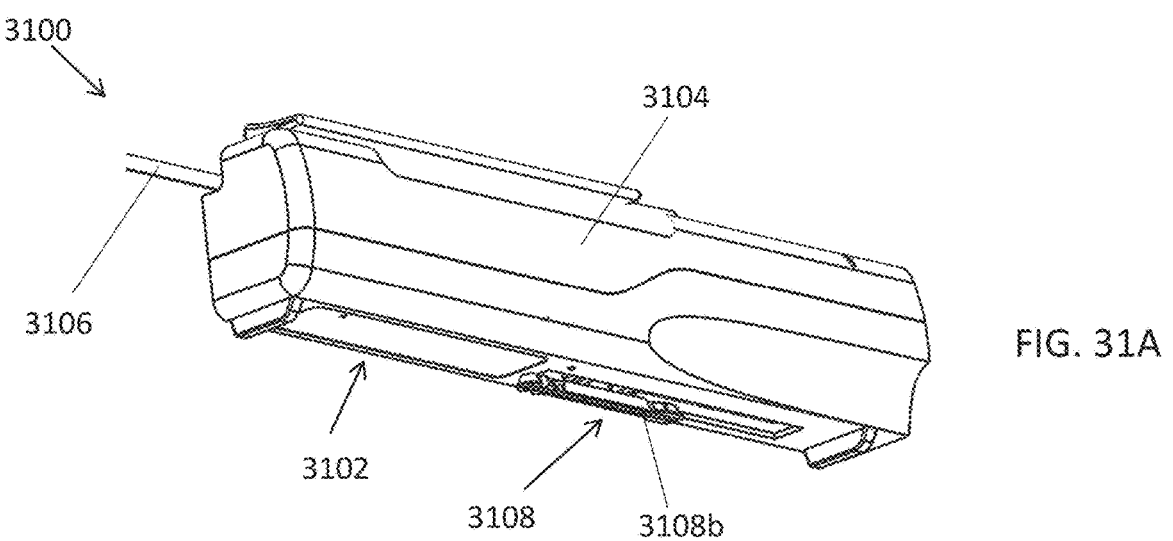
FIG. 31A is a simplified schematic of an underside of a modular unit including a motor unit housing and a surgical arm, according to some embodiments of the invention.
FIG. 31B is a simplified schematic of a linear unit, according to some embodiments of the invention.
FIG. 31C is a simplified schematic of a sliding element attached to a portion of a support, according to some embodiments of the invention.

FIG. 31A is a simplified schematic of an underside 3102 of a modular unit 3100 including a motor unit housing 3104 and a surgical arm 3106, according to some embodiments of the invention. In some embodiments, the motor unit includes a linear unit 3108. In some embodiments, one or more portion of a linear unit is disposed within a motor unit housing and one or more portion of the linear unit extend outside of motor unit housing e.g. second portion 3108b.

FIG. 31B is a simplified schematic of a linear unit 3108, according to some embodiments of the invention. Motor unit housing is not illustrated in FIG. 31B. In some embodiments, linear unit 3108 includes a sliding element 3110 coupled to a motor 3112 where motor 3112 is configured to move the sliding element 3108 on a rail 3114.

In some embodiments, sliding element 3110 is coupled to motor 3112 by a screw mechanism where the motor rotates the screw to move the sliding element on the rail. In some embodiments, sliding element 3110 includes a first portion 3108a which, in some embodiments, is located within a motor unit housing and a second portion 3108b which, in some embodiments, is located outside the motor unit housing. In some embodiments, second portion 3108b is fixed to a support (e.g. support 282 FIG. 2A, e.g. support 382 FIG. 3A) and movement of sliding element 3108 moves the modular unit with respect to the support.

FIG. 31C is a simplified schematic of a sliding element 3108 attached to a portion of a support 3116, according to some embodiments of the invention. In some embodiments, support portion 3116 includes an anchor 3118 which is sized and/or shaped to receive second portion 3108b. In some embodiments, support portion has one or more overhanging edge 3120. In some embodiments, reactive force of overhanging edge/s to the weight of the modular unit holds the modular unit onto the support portion.

In some embodiments, second portion 3108b is slid into anchor 3118. In some embodiments, support portion is sized and/or shaped that second portion 3108b is placed into anchor 3118 and then slid underneath overhanging sides. In some embodiments, support portion 3116 and second portion 3108b include a locking mechanism which locks the two portions together. For example, in some embodiments, a spring loaded protrusion (on one portion) which fits into a matching indentation (on the other portion).

In some embodiments, a system includes a plurality of motor units, each including an integral linear unit. In some embodiments, when a plurality of motor units are connected, a single linear unit (e.g. which is integral to one of the motor units) is used to actuate linear movement of the motor construct (including a plurality of connected motor units).

For example, referring to FIG. 31A, in some embodiments, when modular unit 3100 is connected to an additional modular unit, only second portion 3108b of modular unit 3100 (and not a second portion of the additional modular unit) is attached to a support portion, the actuation of 3108b moving the motor construct of the two attached motor units.

FIGS. 7A-7D are diagrams of various configurations of systems comprising different combinations of modular units, according to some embodiments of the invention.

FIG. 7A is a diagram of a configuration comprising two arms actuated by two motor units which are coupled to each other (for example as shown hereinabove in FIG. 6A). In some embodiments, the motor units are closely coupled to each other in a manner that approximates the arms and holds them adjacent each other. In some embodiments, a linear unit (for example unit 290 as described hereinabove in FIGS. 2A-2C) is coupled to one or both of the motor units. Optionally, the linear unit is configured to move the device as a whole (e.g. advance and/or retract both motor units as one piece).

In some embodiments, the linear unit is configured to be removably coupled to the motor unit. Optionally, the linear unit comprises a motor configured for actuating the linear unit. In some embodiments, the motor unit comprises an additional controller configured for controlling the motor of the linear unit (e.g. a $7^{th}$ controller, for example in a motor unit comprising 6 motors controlled by 6 respective controllers). In some embodiments, the additional controller (e.g. $7^{th}$ controller) is configured to detect if a linear unit was attached to the motor unit, for example by electrically detecting attachment of the motor of the linear unit to the arm motor unit.

A configuration for example as shown in FIG. 7A may be especially advantageous for use in operations performed through a single opening (e.g. a natural orifice or a single incision), such as SILS (Single Incision Laparoscopic Surgery) or vaginal operations, for example hysterectomy.

In FIG. 7B, two separate modular units are used, according to some embodiments. In some embodiments, the linear unit is an integral part of the motor unit. In some embodiments, for example in a system structured for operating through a single port, (e.g. in which the motor units are attached to each other to approximate the arms to each other), only one of the linear units is used for actuating the motor construct comprising the two attached motor units. A potential advantage of using only one of the linear units for actuating movement may include reducing unintentional use of the linear units, for example instructing one motor unit to move proximally and the other motor unit to move distally.

In some embodiments, the motor unit comprises a sensor (e.g. a microswitch) configured for detecting whether a linear unit was operably coupled to an outer connector. A potential advantage of a sensor configured for detecting attachment of the linear unit to an outside component may include detecting an architecture of use, for example detecting if the system is configured for a single-port approach (e.g. comprising motor units coupled to each other to define a construct moveable by a single linear unit) or a multi-port approach (e.g. comprising separate motor units, each configured to be moved by a respective linear unit). In some embodiments, a shape and/or size of the outer connecter is selected so that only a predefined number of linear units can be attached to it, for example one linear unit, two linear units and/or other number of units. In an example, when a motor construct comprising two linear units (e.g. of two motor units) is used, the outer connector may be shaped and/or sized to enable only one of the linear units to be attached.

Limiting the connection to the outer connector, for example by using an outer connector of a selected shape and/or size may be advantageous in reducing user mistakes (e.g. connecting two linear units of two motor units that are coupled together, for example for use in a single port approach).

FIG. 7C is a diagram of a configuration in which both motor units are coupled to linear units, according to some embodiments. Optionally, the linear units are configured to move (e.g. advance and/or retract) each of the motor units independently of each other. A configuration for example as shown in FIG. 7C may be especially advantageous for use in operations in which multiple openings are used, for example in surgical operations such as multi-quadrant surgeries, operations for treating tissue adhesions in the abdomen and/or in the umbilicus.

FIG. 7D is a diagram of a configuration comprising a first modular unit including an arm, a motor unit and a linear unit; and a second modular unit comprising a motor unit configured to actuate two arms, according to some embodiments.

In some embodiments, a motor unit or construct is not coupled to a linear unit.

Optionally, the motor unit or construct is coupled to a manual sliding mechanism.

Figure 8A:
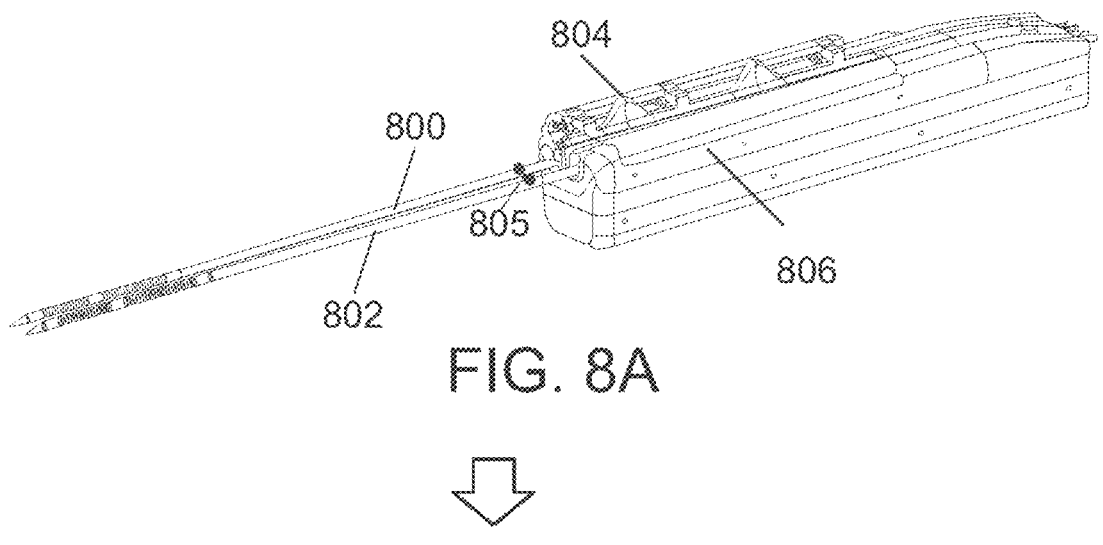
FIGS. 8A-8B illustrate an exemplary configuration including two modular units, according to some embodiments of the invention.
Figure 8B:
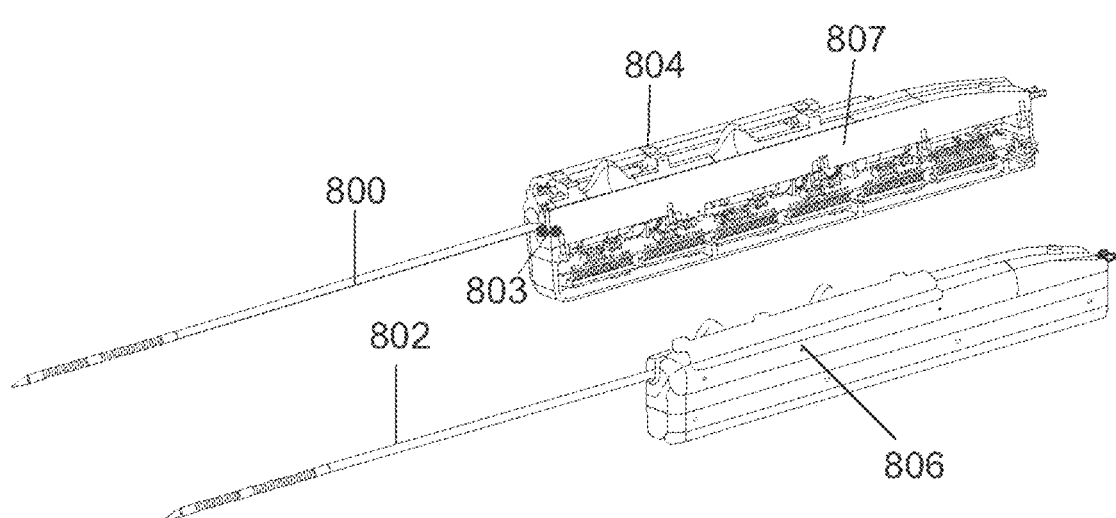

FIGS. 8A-8B illustrate an exemplary configuration including two modular units, in which the motor units 804 and 806 are attached to each other. Optionally, the units are attached by one or more of an interference fit between the housings of the motor units, mechanical attachment means (e.g. screws, pins, fasteners and/or other connectors), and/or electromagnetic means. Additionally or alternatively, the motor units are held together by an external housing (not shown) in which the motor units are received.

In some embodiments, an arm such as arm 800 is positioned at a distance 803 from a longitudinal face 807 of motor unit 804. Optionally, distance 803 is smaller than 7 mm, smaller than 5 mm, smaller than 2 mm, or intermediate, longer or shorter distances. Optionally, when the two motor units are aligned adjacent each other, arms 800 and 802 which coupled to motor units 804 and 806 respectively are held closely to each other by the motor units, for example so that a distance 805 between the arms, along an axis perpendicular to the long axis of the arms, is less than 20 mm, less than 8 mm, less than 1 mm, or intermediate, longer or shorter distances.

Figure 9A:
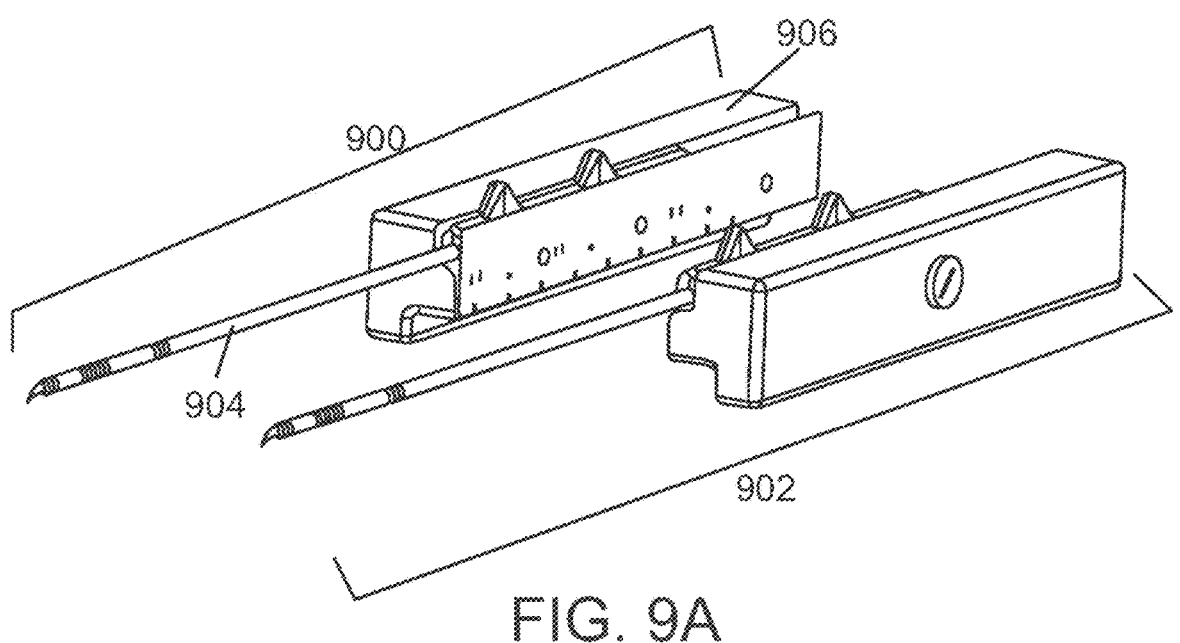
FIGS. 9A-9B illustrate an exemplary configuration of a system including two separated modular units, according to some embodiments of the invention.
Figure 9B:
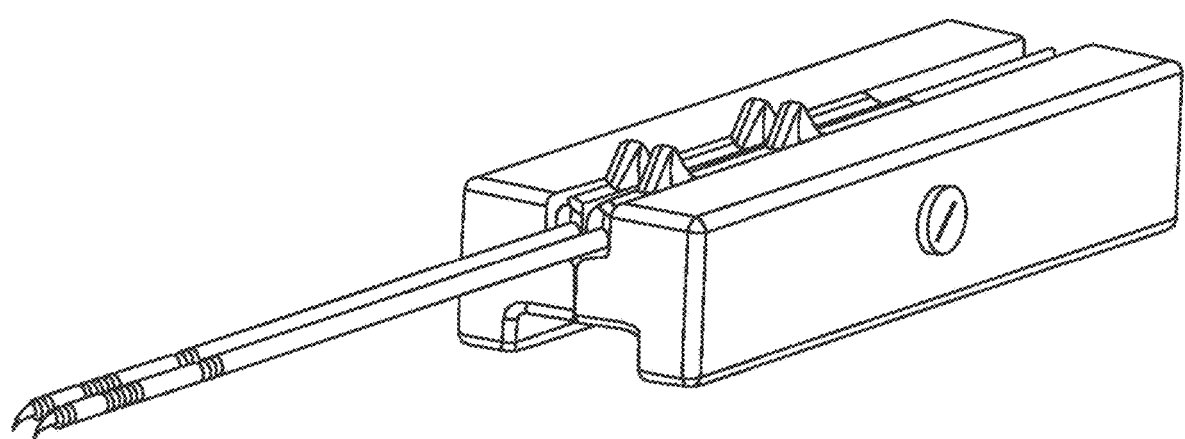

FIGS. 9A-9B illustrate an exemplary configuration of a system including two separate modular units 900 and 902, each comprising an arm 904 operated by a motor unit 906. In some embodiments, during operation, each modular unit is situated at a different location relative to the bed (for example bed 380, FIGS. 3A-3B) and/or relative to the patient. In some embodiments, the units are situated with respect to different surgical ports, for example in a manner in which each arm is configured to enter a different port. Insertion of surgical arms via different ports may be advantageous in operations in which force (e.g. traction) is applied in one direction and a counter force is applied in the opposite direction (e.g. when treating tissue adhesion).

Figure 28A:
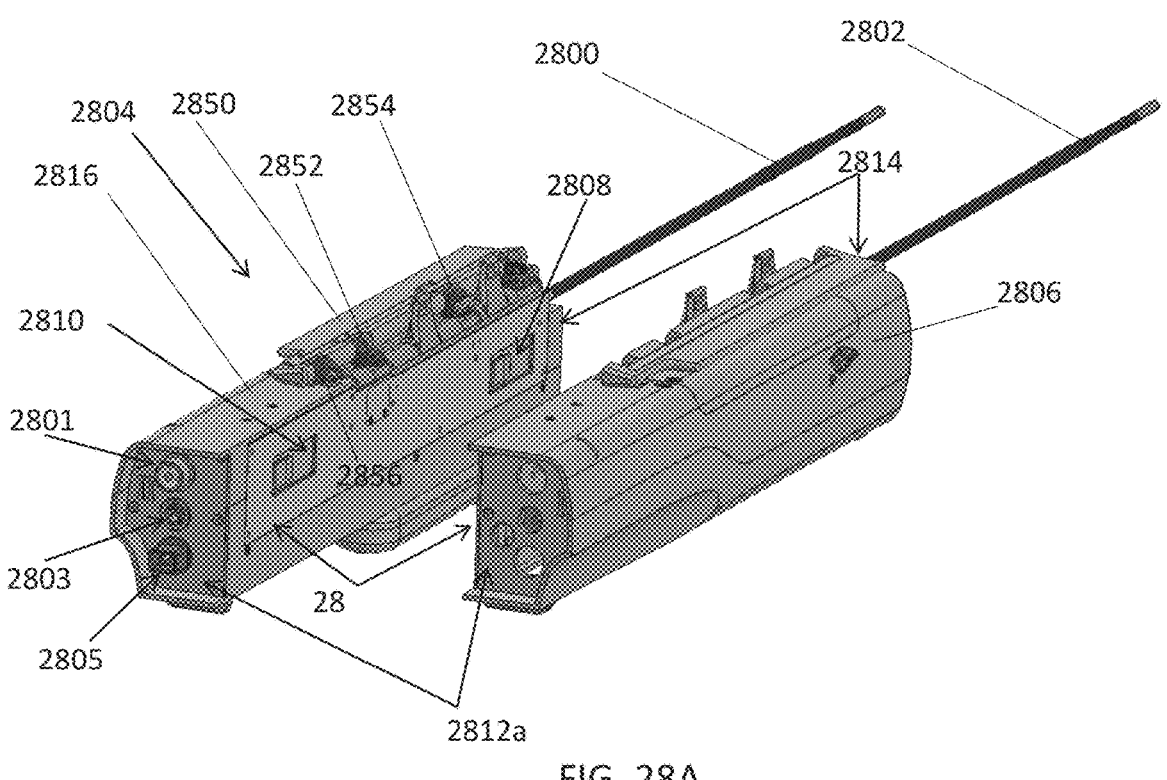
FIG. 28A is a simplified schematic of a system including two separate modular units configured to be attached to each other, according to some embodiments of the invention.

FIG. 28A is a simplified schematic of an exemplary configuration of a system including two separate modular units configured to be attached to each other, according to some embodiments of the invention. In some embodiments, a first modular unit includes a first surgical arm 2800 and a first motor unit 2804 and a second modular unit includes a second surgical arm 2802 and a second motor unit 2806. In some embodiments, the units are attached using more than one attachment, for example, more than one slide attachment 2810, 2808.

In some embodiments, a plurality of attachments are not aligned on a motor unit longitudinal face. For example, as illustrated in FIG. 28A, attachment 2810 is closer to a top face 2816 of motor unit 2804 than a second attachment 2808. Potentially, having a plurality of attachments with different positions both parallel to a long axis and perpendicular to a long axis of the motor unit longitudinal face on which they are located increases attachment strength under loading from directions including a components perpendicular to a plane of the longitudinal face and a component parallel to a plane of the longitudinal face.

In some embodiments, surgical arms and/or motor units are modular. In some embodiments, one or more surgical arm is configured to be removably attached to a motor unit. FIG. 28E is a simplified schematic of a plurality of modular surgical arms 2802, 2804, according to some embodiments of the invention. In some embodiments, a surgical arm 2804 includes a gear unit 2822 which includes surgical arm gears 2810. In some embodiments, surgical arm gears 2810, when arm 2804 is connected to a motor unit, actuate the arm (e.g. as described with reference to FIG. 5C and FIG. 29). In some embodiments, arm 2804 includes one or more handle, for example, two handles 2812, 2814 e.g. configured for grasping by a user, one in each hand. In some embodiments, handles 2812, 2814 and/or a side of the arm opposing exposed portions of arm gears 2810 has an outer surface which is an insulating material. For example, meaning that, when arm 2804 is inserted into a motor unit (e.g. as illustrated in FIGS. 7A-7B) electrically live portions of the device are not at a surface of the device.

In some embodiments, each motor unit receives electrical power from and/or control signals at one or more connection point, for example, connection points 2801, 2803, 2805, where, in some embodiments, each connection point is configured to be connected to a cable. In an exemplary embodiment, first connection point 2801 is configured to be connected to a monopolar power supply, second connection point 2805 is configured to be connected to a bipolar power supply and third connection point 2803 is configured to receive power and/or control signals. In some embodiments, power and/or control signals received at the third connection point are delivered (e.g. by connections within the motor unit) to motors within the motor unit.

In an exemplary embodiment, a long axis length, L1, of the surgical arm is 500-1000 mm, or 650-800 mm or about 728 mm or lower or higher or intermediate ranges or lengths, a length, L2, of a surgical arm gear unit 2822 is 150-350 mm, or 200-300 mm or about 260 mm or lower or higher or intermediate ranges or lengths, and a thickness, T1, of a body of surgical arms is 5-12 mm or 7-9 mm or about 8.2 mm or lower or higher or intermediate ranges or thicknesses.

Referring back now to FIG. 28B, in some embodiments surgical arm 2800 fits into a recess within motor unit 2804 such that gears of the surgical arm contact gears of motor unit 2804 (gears not visible in FIG. 28A).

In some embodiments, a surgical arm is inserted into a recess (e.g. recess 2804) in a motor unit by holding the arms above the face of the recess and lowering the arms into the recess. Alternatively, in some embodiments the arm is held in front of a face of the motor unit from which the surgical arms extend and are then pushed into the recess.

In some embodiments, the recess includes one or more protrusion and/or indentation which is configured to prevent the surgical arm from being inserted incorrectly into the recess. For example, a stopper which prevents insertion of the arm past a desired point.

In some embodiments, connection between surgical arm 2800 and motor unit 2804 is along a length of the surgical arm and/or motor unit.

For example, in some embodiments, an angle of long axis of a portion of surgical arm (e.g. surgical gear unit 2822 which, in some embodiments forms a distal end of the surgical arm) within a motor unit is 0-30° or 0-20° or 0-10° or lower or higher or intermediate angles or ranges, of a long axis of the motor unit.

For example, in some embodiments, a long axis of a surgical arm, when the arm is attached to the motor unit, is housed within the motor unit, extending within the motor unit for 80-99%, or 80-95% or 60-99% of a length of the motor unit.

For example, where attachment is between surgical gear unit 2822 and the motor unit. For example, where 20-50%, or 25-40%, or about 35% or lower or higher or intermediate percentages or ranges, of a length of a surgical arm is attached to the motor unit.

In some embodiments, surgical arm 2800 is mechanically held in position by one or more component. In some embodiments, motor unit 2804 includes one or more clamping hammer 2852, 2854 which contact and/or apply pressure to the surgical arm.

In some embodiments, clamping hammers 2852, 2854 are brought into contact and apply pressure to surgical arm 2800 when a flap 2850 is rotated about a hinge attachment to motor unit 2804 to a closed position illustrated in FIG. 28A.

In some embodiments, motor unit 2804 includes a sensor detecting whether a surgical arm has been attached. In some embodiments, motor unit 2804 includes a lock clamping hammer 2856 which, by movement of flap 2850, is brought into contact with a sensor (e.g. a microswitch). In some embodiments, this sensor provides a signal to a processor (e.g. located within a motor unit and/or located within a control console) indicating that flap 2850 is in a closed position holding the arm onto the motor unit.

In some embodiments, the system will issue an alert to a user and/or stop use of the surgical arm/s if the sensor indicates that flap 2850 is open. In some embodiments, surgical arms are only enabled for use (movement and/or electrosurgery is enabled) upon a processor receiving a signal that the flap is closed. In some embodiments, lock clamping hammer 2856 is configured to be held in position by a component inserted through a hole within it. In some embodiments, locking of lock clamping hammer 2856 holds the flap and/or surgical arm in position.

Figure 28B:
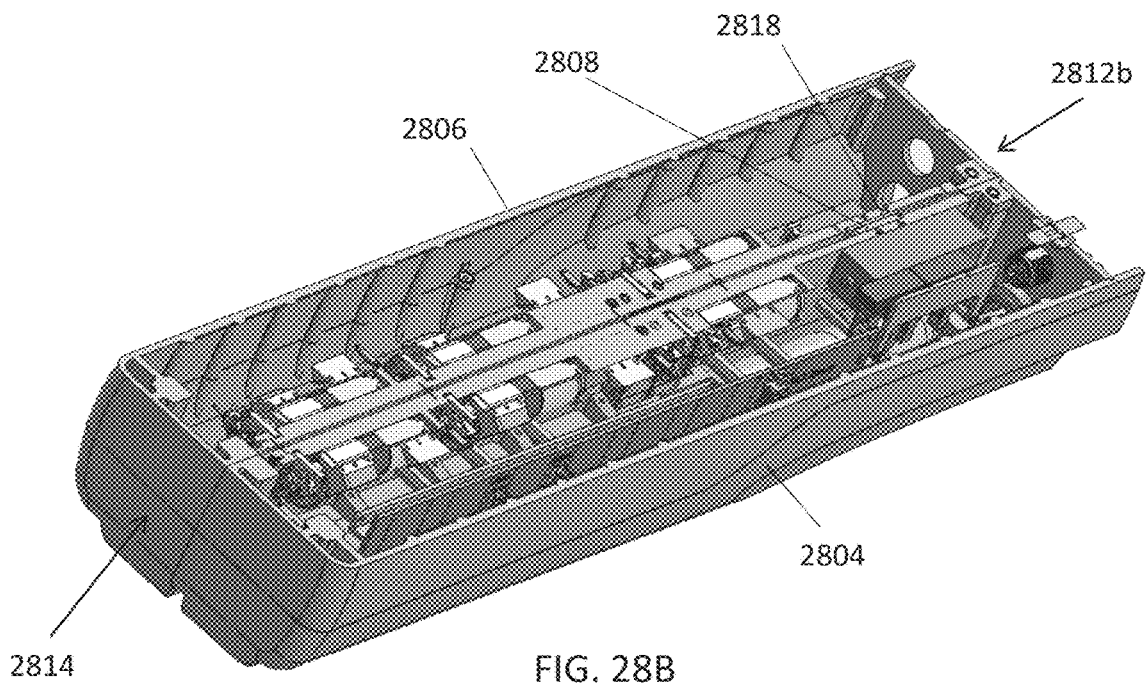
FIG. 28B is a simplified schematic cross section of a motor construct, showing attachment between motor units, according to some embodiments of the invention.
Figure 28C:
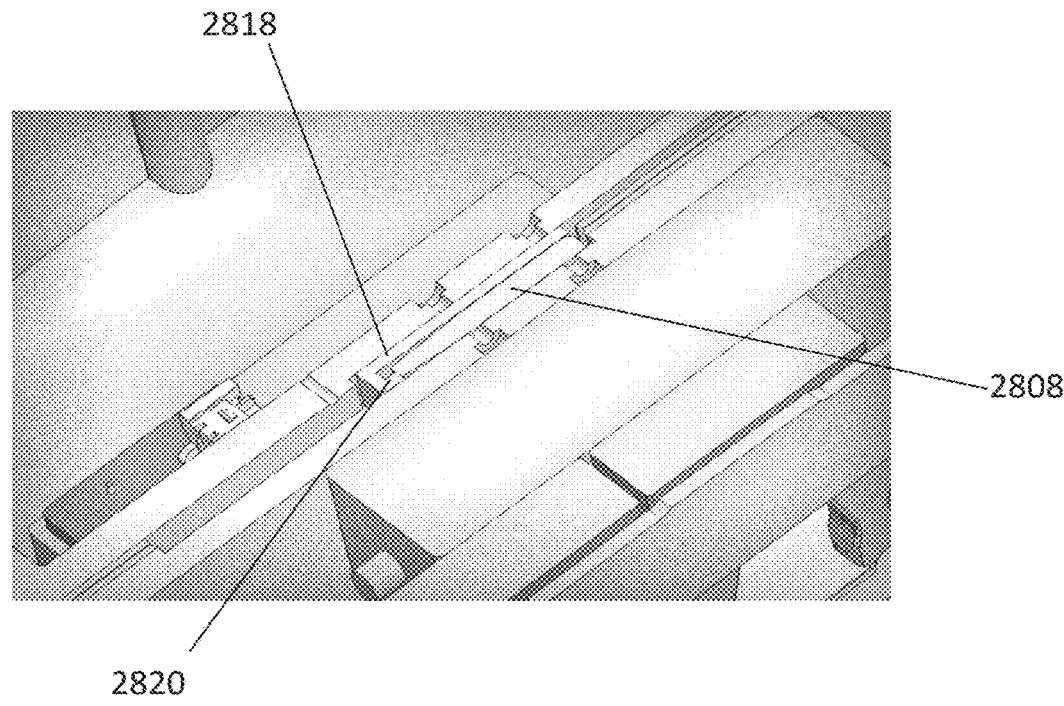
FIG. 28C is an enlarged view of the attachment of FIG. 28B, according to some embodiments of the invention.
Figure 28D:
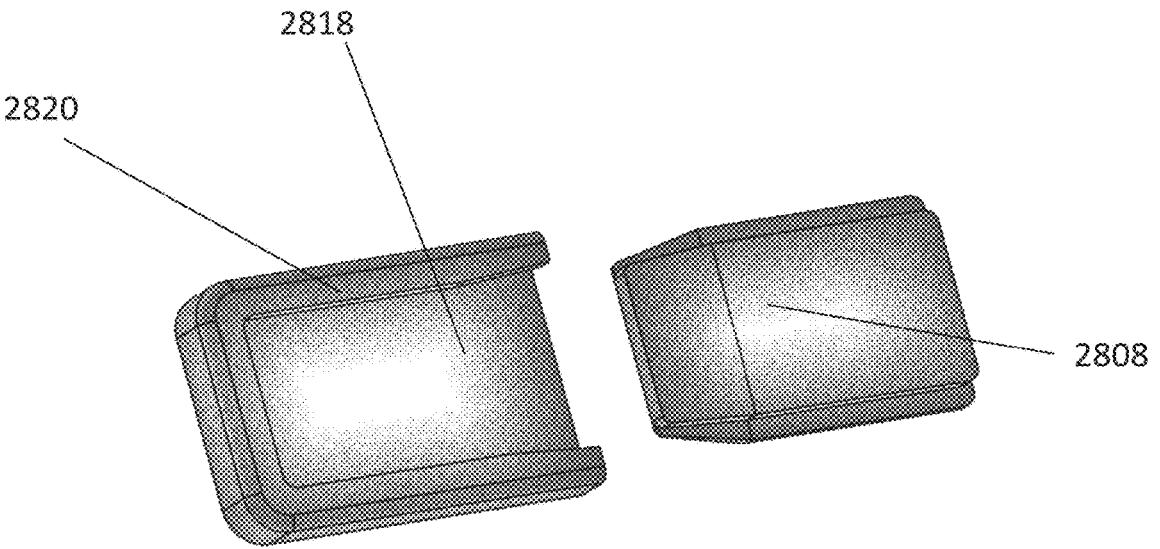
FIG. 28D is a simplified schematic of a slide attachment, according to some embodiments of the invention.
Figure 28E:
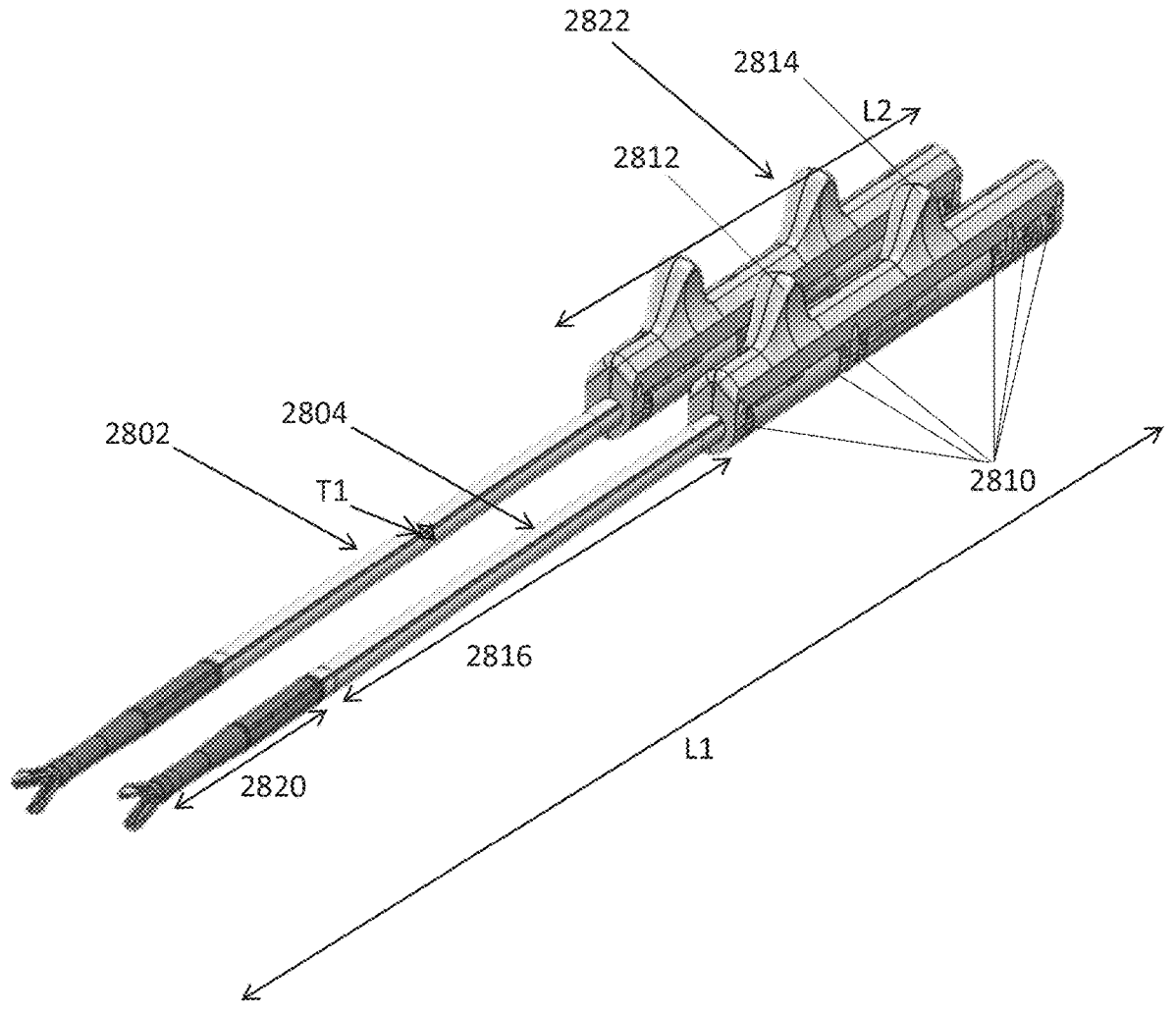
FIG. 28E is a simplified schematic of a plurality of modular surgical arms, according to some embodiments of the invention.

FIG. 28B is a simplified schematic cross section of a motor construct, showing attachment 2808, 2818 between motor units, according to some embodiments of the invention. FIG. 28C is an enlarged view of the attachment 2808, 2818 of FIG. 28B, according to some embodiments of the invention. FIG. 28D is a simplified schematic of a slide attachment, according to some embodiments of the invention.

In some embodiments, a protrusion 2808 on motor unit 2804 fits into an indentation 2818 on second motor unit 2806. In some embodiments, motor units are held together and slid past each other thereby protrusion 2808 into indentation 2818.

In some embodiments, protrusion 2808 is held under a lip 2820 surrounding indentation 2818, where the lip (or lips if there are a plurality of such attachments, e.g. as illustrated in FIG. 28A) are sufficiently strong to hold the motor units together. In some embodiments, a first end of protrusion 2808 is tapered, potentially easing alignment and/or insertion of the protrusion into the indentation.

Figure 10A:
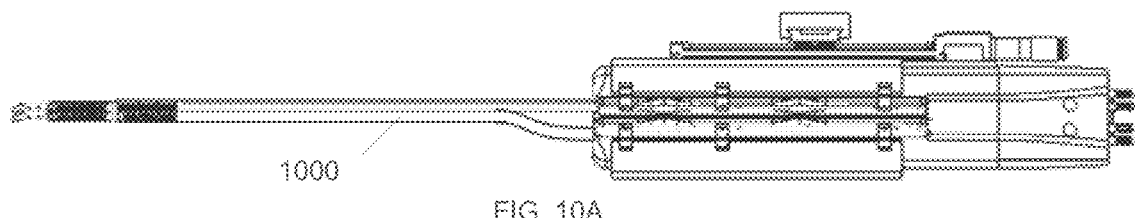
FIGS. 10A-10C are exemplary mechanical arm layouts, according to some embodiments of the invention.
Figure 10B:
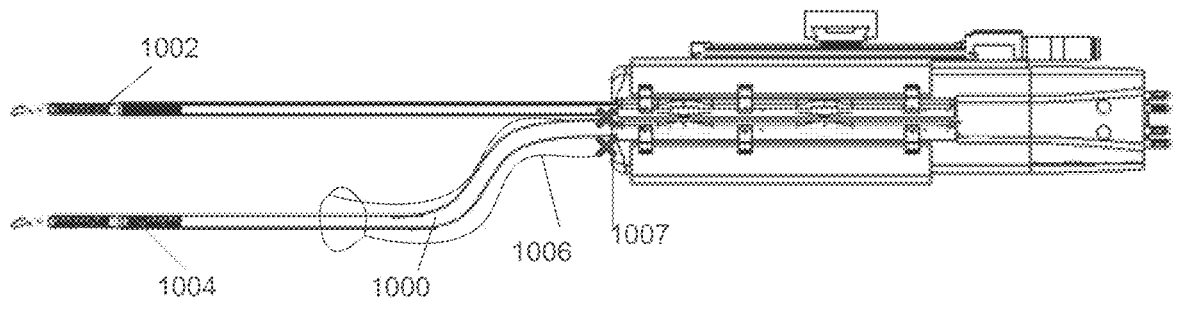
Figure 10C:
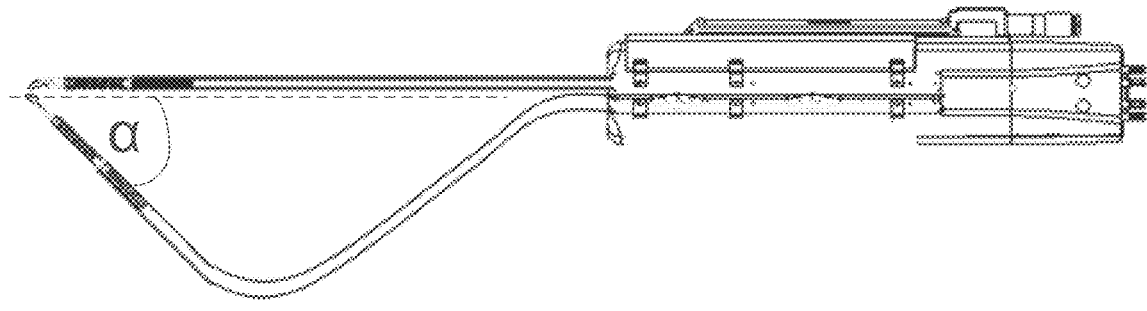

FIGS. 10A-10C are exemplary mechanical arm layouts, according to some embodiments.

In some embodiments, one or more arm portions such as an arm portion extending between the motor unit and the first arm joint (e.g. shoulder joint), defined herewith as torso 1000, comprises a non-linear configuration.

In some embodiments, torso 1000 is performed with one or more curvatures, for example set during factory calibration. Additionally or alternatively, torso 1000 is bent by the user, manually and/or via the user input device, before and/or during operation.

In some embodiments, for example as shown in FIG. 10A, torso 1000 of one of the both of the arms is curved such that the arms converge towards each other.

Additionally or alternatively, for example as shown in FIG. 10B, torso 1000 of one or both arms is curved such that the arms diverge away from each other.

Optionally, a parallel alignment between more distal portions 1002 and 1004 of the arms (e.g. an arm portion distally to the shoulder joint) is maintained.

Additionally or alternatively, for example as shown in FIG. 10C, torso 1000 of one or both the arms is curved such that the arms diverge away from each other and then converge towards each other, positioning arm portions 1002 and 1004 at a different orientation relative to each other, for example arm portion 1004 is positioned at an angle α relative to arm portion 1002. In some embodiments, angle α ranges between, for example, 0-90 degrees, such as 20 degrees, 55 degrees, 80 degrees or intermediate, larger or smaller angles.

An arm layout for example as shown in FIG. 10A may be advantageous for use in a single-port surgical approach. Arm layouts as shown in FIGS. 10B and 10C may be advantageous for use in a multi-port surgical approach.

In some embodiments, a curved portion of the torso comprises torque transferring portions and/or elements for transferring torque from the motor unit to more distal arm portions. In an example, the torque transferring portion comprises stacked annular segments.

In some embodiments, for example as shown in FIG. 10B, an over tube 1006 positioned to over lie at least a portion of torso 1000. In some embodiments, over tube 1006 is rigid. In some embodiments, over tube 1006 is pre-shaped to define a fixed curvature. Optionally, over tube 1006 is fixedly attached to the motor unit, for example via one or more attachments 1007. In some embodiments, over tube 1006 is not affected by actuation of the motor unit, while the torso extending throughout the over tube is affected, for example the torso is rotated around its axis by actuating the rotation gear.

Figure 11A:
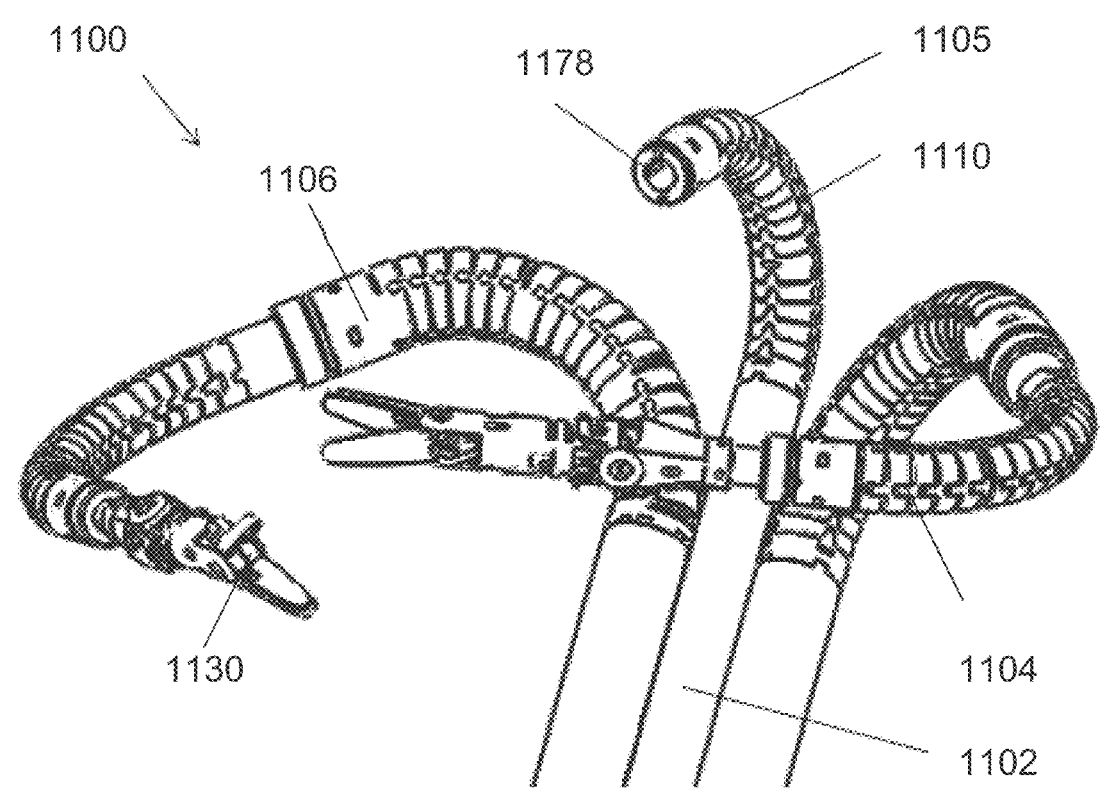
FIGS. 11A-11B are a simplified schematic side view of a device 1100 including 3 arms, according to some embodiments of the invention.
Figure 11B:
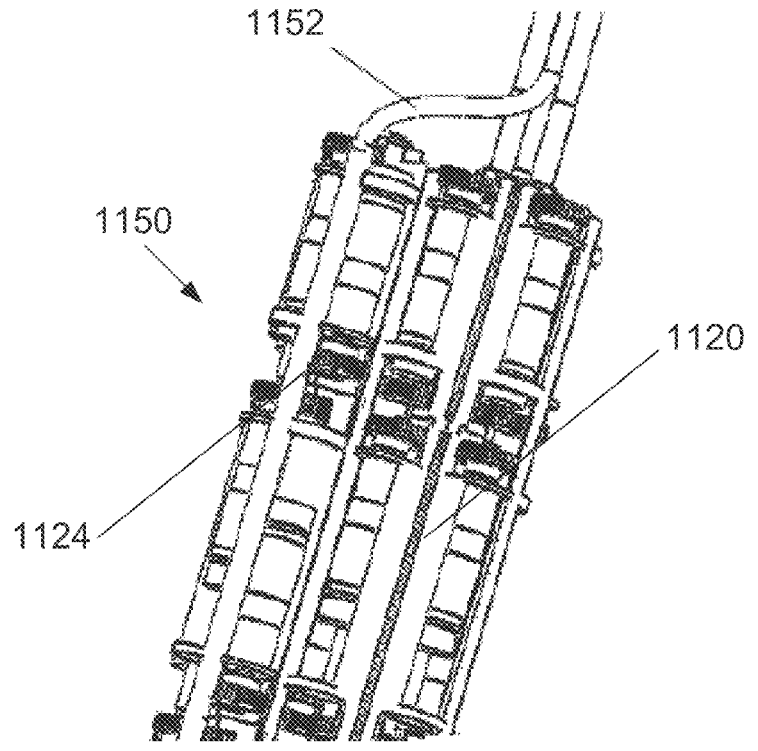

FIGS. 11A-11B are a simplified schematic side view of a device 1100 including 3 arms 1104, 1105, 1106, actuated by 3 respective motor units, 1120, 1122, 1124, according to some embodiments.

In some embodiments, an arm comprises a tool, optionally disposed at a distal end of the arm, for example, as shown herein, arms 1104 and 1106 each comprise a gripper 1130, and arm 1178 carries a camera 1178, according to some embodiments.

In some embodiments, for example as shown herein, motor construct 1150 comprises two motor units 1120, 1124 configured for actuating movement of arms 1104 and 1106 respectively, and a third motor unit 1122 configured for actuating movement of arm 1105 which carries the camera. Optionally, motor unit 1122 comprises a single actuation mechanism for actuating movement of joint 1110.

In some embodiments, as also shown in this figure, a torso 1102 of arm 1105 comprises one or more curved portions 1152. Optionally, torso 1102 is curved to allow for positioning arm 1105 (and thereby position camera 1178) at a selected location and/or orientation and/or distance with respect to arm 1104 and/or to arm 1106.

In some embodiments, movement of a mechanical arm including a camera is controlled by measured movement of a user's head. For example, by movement of a user's head in space and/or by movement of a user's head with respect to one or other body part (e.g. torso and/or neck).

In some embodiments, movement of a mechanical arm including a camera is controlled by measured movement of a user's limb (e.g. arm). For example, the arm includes at least a first and a second flexible portion, the movement of which is controlled by a user shoulder and elbow joint respectively.

Additionally or alternatively, in some embodiments, movement of a mechanical arm including a camera is controlled by movement of portion/s of an input device.

Additionally or alternatively, in some embodiments, a position of one or more tool inserted into a patient body (e.g. a camera, e.g. a mechanical arm, e.g. a tube) is controlled by one or more device arm. For example, in some embodiments, a tool is grasped by one or more device arm and moved into a desired position. For example, in some embodiments, a tool (e.g. a camera) includes an elastically deformable portion such that, upon positioning of the tool the tool remains in position until the tool is repositioned. For example, in some embodiments, a suction tube is positioned by a surgical arm moving the tube. In some embodiments, a tool (e.g. a tube) includes one or more elastically deformable portion, such that, for example, the tool is moved into a desired position by a movement of a mechanical device arm, returning towards an original position once the tool is released.

FIGS. 12A-12E schematically illustrate different approaches for using one or more mechanical arms in a multi-port surgery, according to some embodiments.

Figures 12A, 12B, 12C, 12D, 12E:
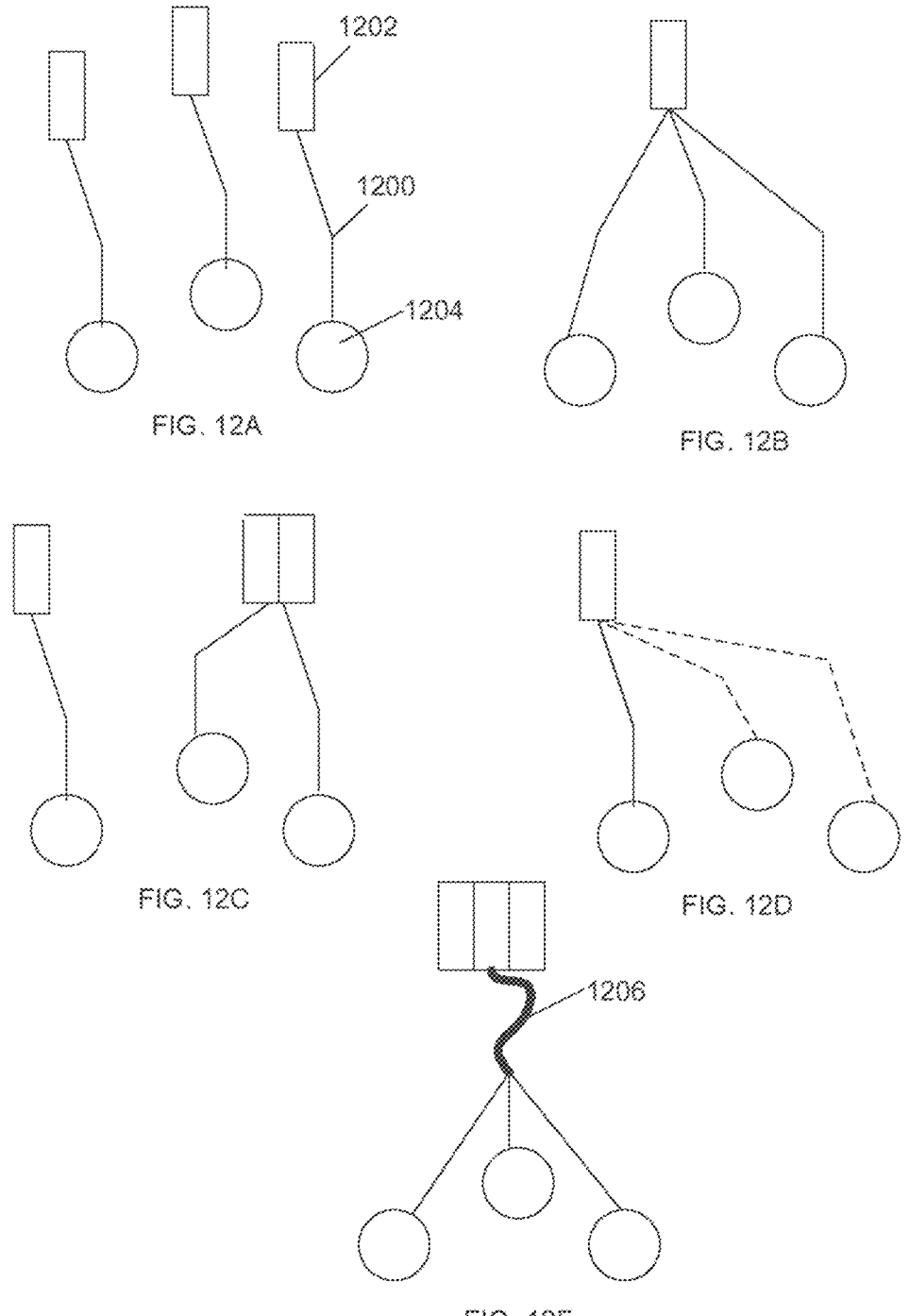
FIGS. 12A-12E schematically illustrate different approaches for using one or more mechanical arms in a multi-port surgery, according to some embodiments of the invention.

In FIG. 12A, 3 arms 1200 are actuated by 3 respective motor units 1202.

Optionally, each arm is configured to enter the patient's body through a different port 1204, according to some embodiments.

In FIG. 12B, 3 arms are actuated by a single motor unit. Optionally, each arm is configured to operate at a different port, according to some embodiments. In some embodiments, a single motor unit configured for actuating more than one arm (e.g. 2 arms, 3 arms) comprises elongated channels for guiding the plurality of proximal extensions of the arms during insertion to the motor unit. Optionally, each extensions is positioned in contact with driving gears (or, in some embodiments, driven gears) configured to actuate movement of the specific arm. Some embodiments comprise a locking mechanism which locks the arm extension in position. Optionally, the locking mechanism is configured to lock each extension separately. A potential advantage of a locking mechanism configured for locking each of the extensions separately may include the ability to replace an arm (e.g. if the arm malfunctions and/or if a different type of tool needs to be used) while maintaining the other arms active. Alternatively, the locking mechanism is configured to lock all extensions in position simultaneously.

In FIG. 12C, 2 arms are actuated by a motor construct comprising two motor units, and a third arm is positioned separately from the two arms and is actuated by its own motor unit. Optionally, each arm is configured to enter through a different port.

Alternatively, the two adjacent arms are configured to operate at the same port, and the third arm is configured to operate at a different port. Alternatively, all three arms operate through the same port.

In FIG. 12D, a single arm actuated by a single motor unit is configured to be moved between multiple ports, for example, after operating through a first port the arm is moved and/or curved to reach a second and/or third port, according to some embodiments.

In FIG. 12E, 3 arms are actuated by 3 respective motor units, and, optionally, proximal portions (e.g. torso portions) of the arms are passed through an over-tube 1206. Optionally, over-tube 1206 is deformable and can be shaped according to the need, so as to position the arms at a selected location and/or orientation relative to the motor units. Optionally, over-tube 1206 is configured to remain in a fixed position following deformation.

Figure 13:
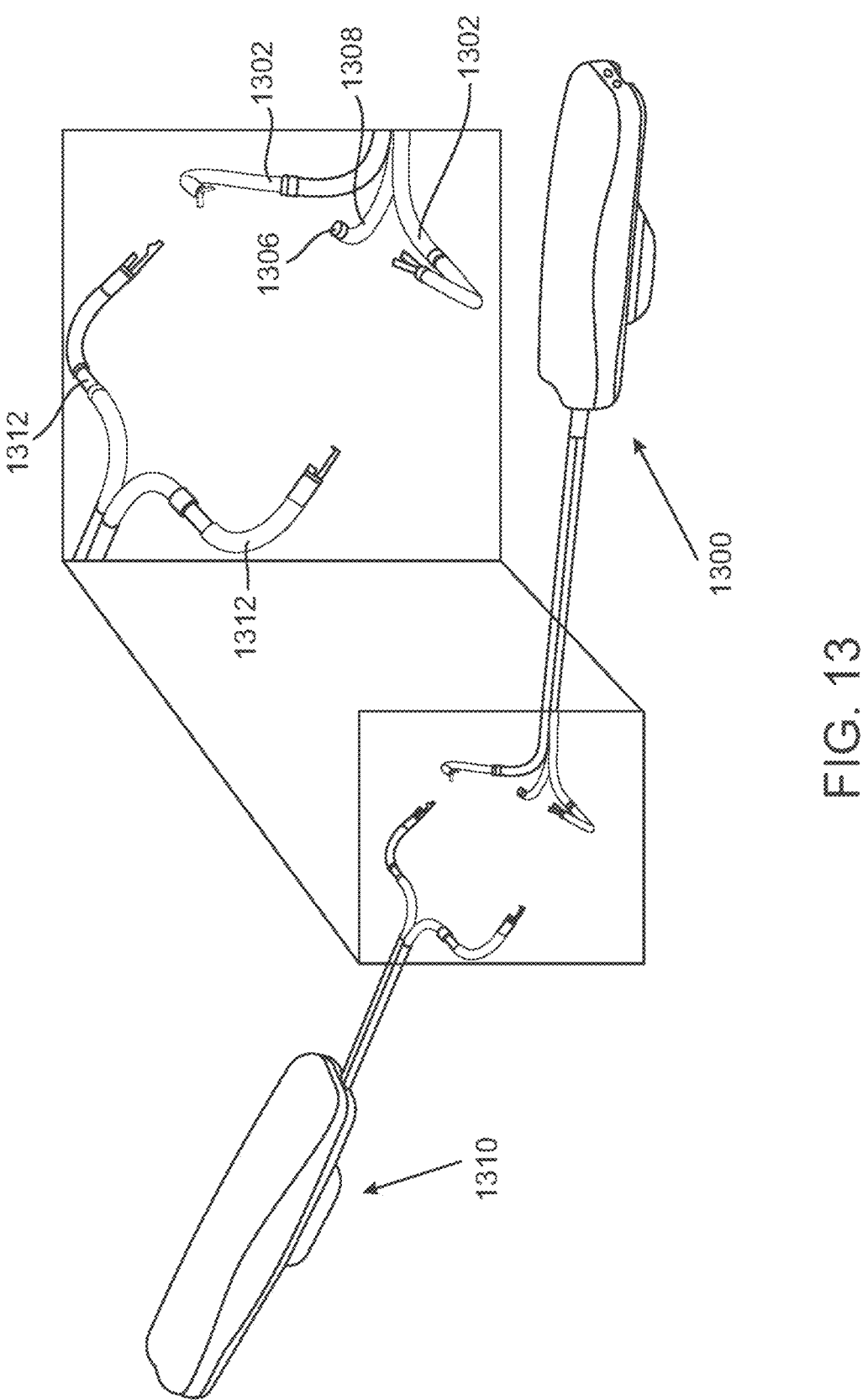
FIG. 13 illustrates use of two systems in a multi-port surgery, according to some embodiments of the invention.

FIG. 13 illustrate use of two systems in a multi-port surgery, according to some embodiments of the invention.

In the exemplary setup shown in FIG. 13, a first system 1300 comprises 3 surgical arms, for example including two arms 1302 comprising an end effecter 1304, and a third 1308 arm carrying an additional tool, such as a camera 1306 (see the enlarged view). A second system 1310 comprises two surgical arms 1312. In some embodiments, first system 1300 is positioned to operate through a first port to the body, for example through the vagina. In some embodiments, the second system 1310 is configured to operate through a second body port, for example through an umbilical port.

Figure 14A:
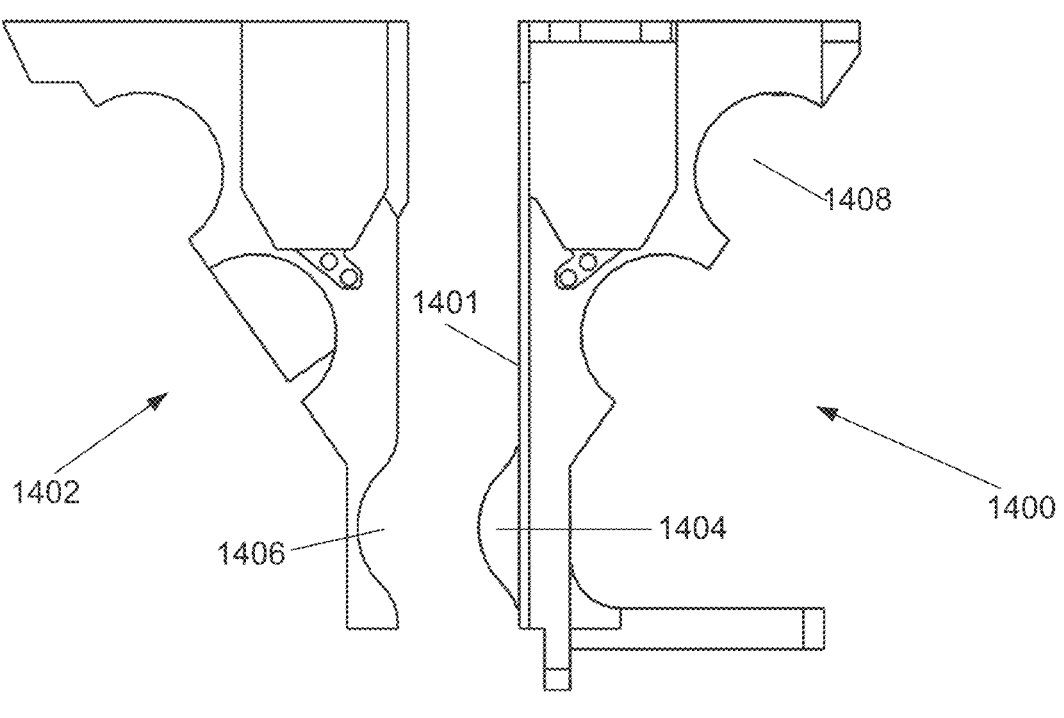
FIGS. 14A-14D illustrate a coupling between two motor units, according to some embodiments of the invention.
Figure 14B:
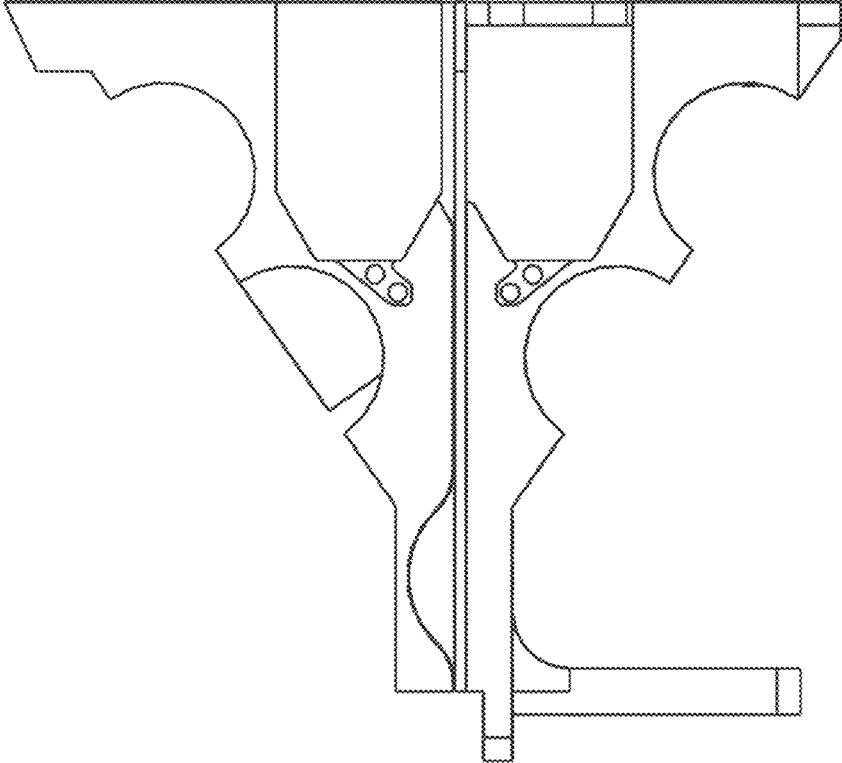

FIGS. 14A-14B illustrate a coupling between motor units, according to some embodiments of the invention.

Figure 14C:
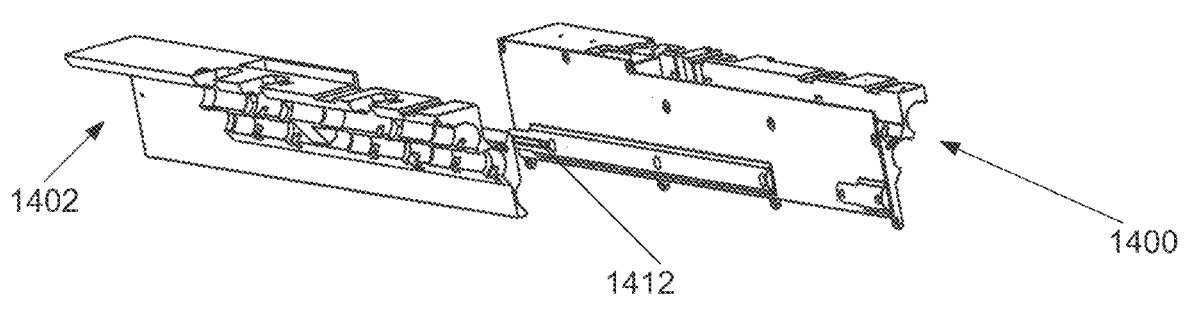
Figure 14D:
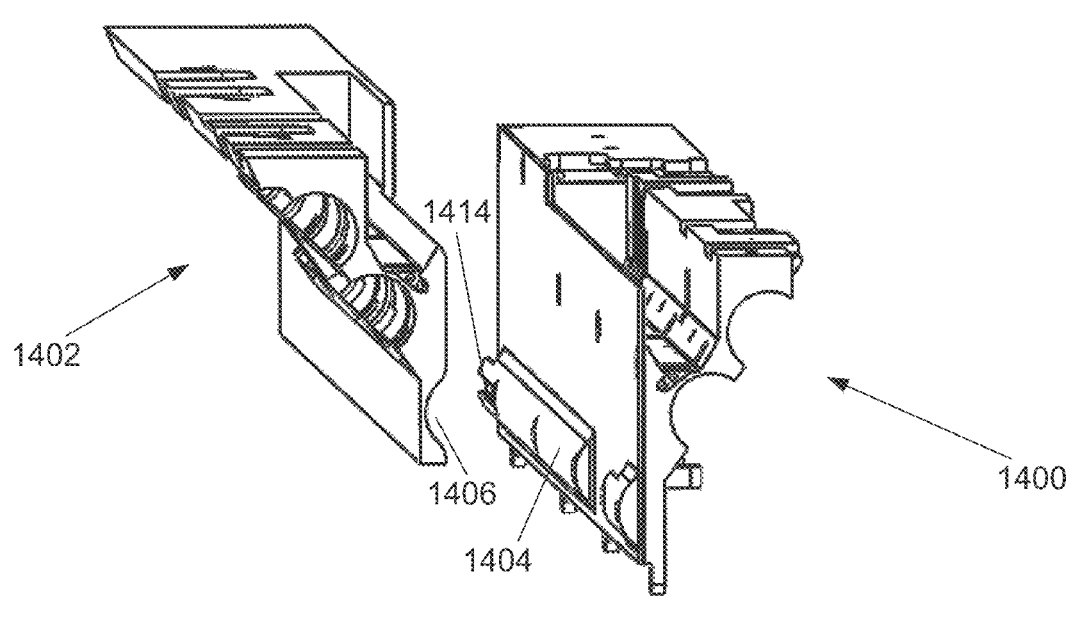

FIGS. 14A-14B show, at a cross section, housings of two motor units 1400 and 1402 configured to be coupled to each other, according to some embodiments. FIGS. 14C-14D show an isometric view of the motor unit housings.

In some embodiments, the motor units are coupled to each other by an interference fit. Optionally, the interference fit coupling comprises one or more protrusions received within one or more respective recesses. In the exemplary configuration shown herein, a longitudinal face 1401 of motor unit 1400 comprises a protrusion 1404 which is configured to be received in a respective indentation 1406 of motor unit 1402. In some embodiments, for example as shown in FIG. 14D, protrusion 1404 and respective indentation 1406 extend along at least a portion of the length of the motor unit.

In some embodiments, a total volume of structural elements coupling between the motor units is relatively small, for example less than 10%, less than 15%, less than 25% or intermediate, larger or smaller percentage of a total volume of the assembled motor construct.

In some embodiments, a geometry of face 1401 is configured to resist shear forces, for example to prevent movement of the motor units with respect to each other once attached, for example movement along an axis perpendicular to the long axis of the motor construct (e.g. movement of a motor unit upwards or downwards with respect to the adjacent motor unit).

In some embodiments, motor unit 1400 is configured to be slidably received in motor unit 1402. Optionally, attachment of the motor units comprises moving (e.g. sliding) one motor unit with respect to another, for example sliding motor unit 1400 in a distal direction with respect to motor unit 1402. Additionally or alternatively, attachment of the units comprises placing one motor unit over another.

In some embodiments, a coupling between the motor units is asymmetric. When the surgical arms are coupled to the motor units, a potential advantage of an asymmetric coupling may include approximating the arms to each other, by bringing the motor units closer together. Potentially, by holding the arms close together, a smaller (e.g. narrower) port can be used for accessing the patient's body. Alternatively, a coupling between the motor units is symmetrical.

In some embodiments, the motor units are configured to lock to each other once connected, for example via a plunger lock 1412 (see FIG. 14C). Optionally, the plunger lock is configured at a distal end of a groove 1414 (see FIG. 14D) in which a respective protrusion on the housing of motor unit 1402 is slidably received.

In some embodiments, the locking is released, for example by releasing a latch configured on the motor unit housing. (It is noted that the housings presented in these figures are shown without the motors and the actuation mechanisms. In some embodiments, a motor is positioned, for example, at cavity 1408).

FIGS. 15A-15E are views of various arrangements of a coupling between gears of the motor unit and an extension of the surgical arm, and a coupling between a motor construct (e.g. comprising more than one motor unit) and a plurality of extensions of surgical arms, according to some embodiments.

Figures 15A, 15B:
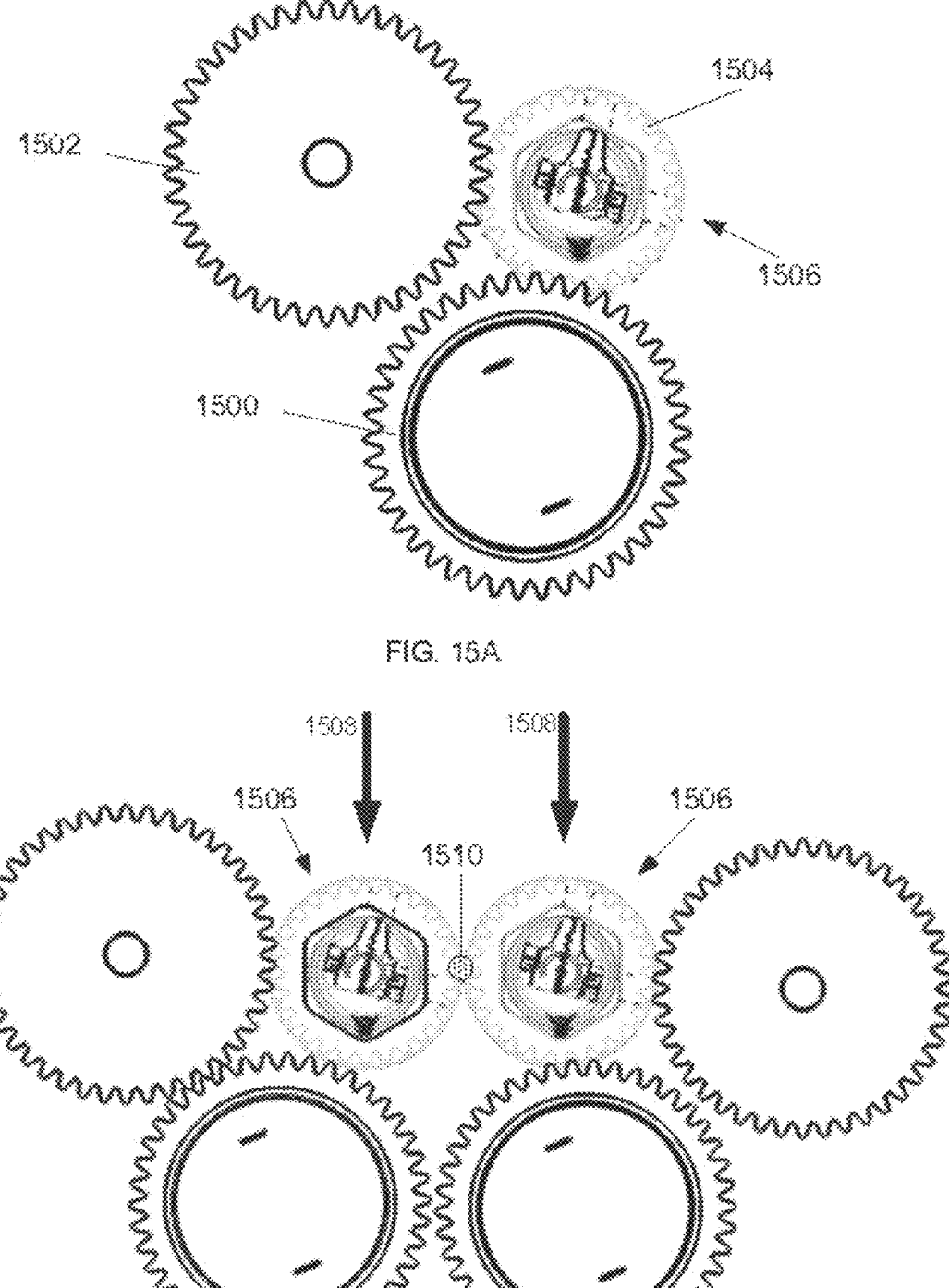
FIGS. 15A-15E are cross section views of various arrangements of a coupling between gears of the motor unit and a surgical arm, and a coupling between a motor construct (e.g. comprising more than one motor unit) and a plurality of surgical arms, according to some embodiments of the invention.

FIG. 15A shows two motor gears 1500 and 1502 of a motor unit (housing not shown), coupled to a gear 1504 of an extension 1506 of a surgical arm (e.g. bending gear and/or rotation gear for example as described hereinabove), according to some embodiments.

In FIG. 15B, two motor units are aligned side by side, defining a motor construct according to some embodiments. Optionally, the motor gears of the two units are symmetrically arranged with respect to each other and/or with respect to a central long axis of the assembled motor construct. In some embodiments, extensions 1506 of two respective surgical arms are positioned adjacent each other. Optionally, extensions 1506 extend along the central long axis 1510 of the construct, opposing each other (e.g. a first extension positioned on one side (e.g. left of) the long axis, the second extension positioned on other side (e.g. right of) the long axis). In some embodiments, extensions 1506 are received in the motor construct from the top, e.g. insertion of the extensions is performed in the direction of arrows 1508. Additionally or alternatively, insertion is performed by sliding the extension into the motor unit, for example in a distal to proximal direction along the long axis of the motor unit.

Figure 15C:
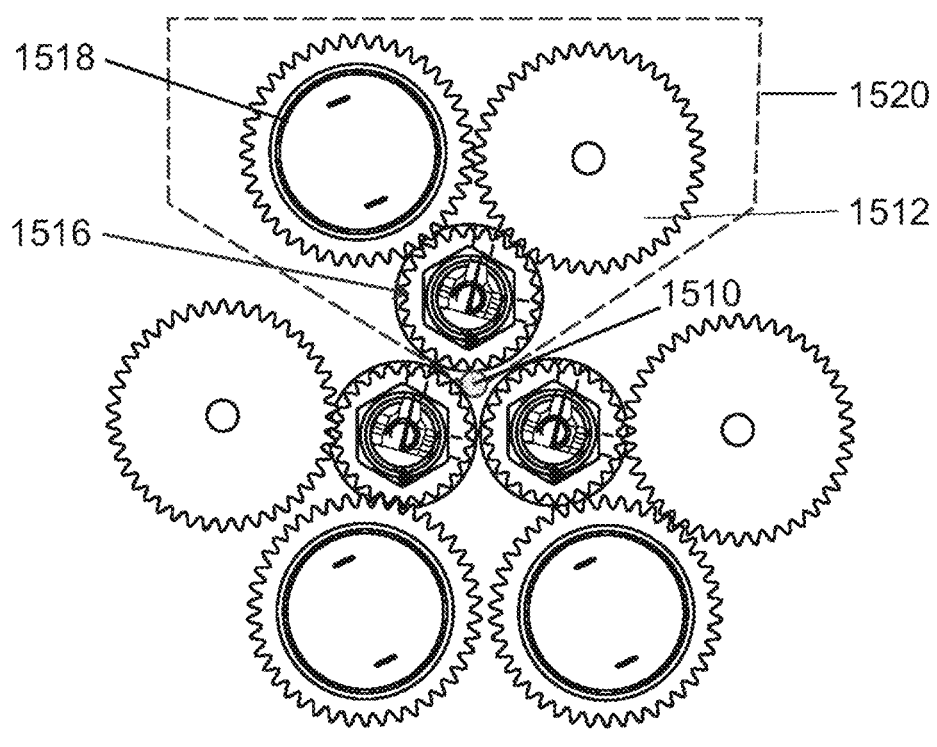

In FIG. 15C, 3 motor units are arranged together to form a substantially circular motor construct, according to some embodiments. Optionally, extensions of 3 surgical arms are positioned about the central long axis 1510 of the motor construct, for example forming a triangular configuration. Optionally, insertion of the extensions to the motor construct comprises loading the extensions to the motor construct, for example by sliding the extensions in a distal to proximal direction into predefined channels or a central lumen of the construct. A configuration for example as shown in FIG. 15C may be especially advantageous for use in a single port operation in which 3 surgical arms are used. Optionally, the three surgical arms are held closely to each other by the motor construct so that the arms can be introduced together into the port to perform the operation.

Figure 15D:
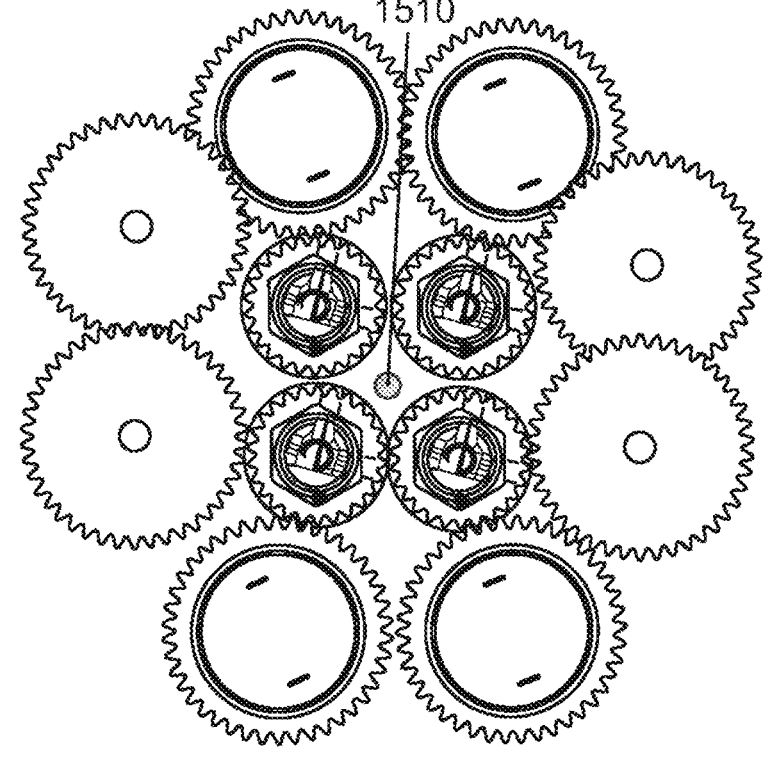

FIG. 15D shows a quadruple arrangement of motor units, according to some embodiments. In this example, 4 extensions are positioned to produce a squared arrangement about the central long axis 1510 of the motor construct. A configuration as shown in FIG. 15D may include 4 separate motor units coupled together, or, for example, two motor constructs (each comprising two pre-coupled motor units) arranged together.

In some embodiments, a motor unit housing includes four longitudinal faces e.g. in some embodiments a motor unit housing has a parallelogram cross section, at least for a portion of a longitudinal length of the motor unit. For example, referring to FIG. 8A, in some embodiments, a motor unit, e.g. motor units 804 and 806, has four longitudinal faces, where a cross section of tangential planes of the longitudinal faces is rectangular. For example, where an angle at an intersection between two longitudinal faces is about 90° (e.g. angles at each intersection between longitudinal faces is about 90°).

In some embodiments, a portion of the motor unit housing has a different shape, for example, in FIG. 8A the motor unit tapers towards a proximal end of the motor unit, a top longitudinal face of the motor unit bends towards a central long axis of the motor unit towards a proximal end of the motor unit.

In some embodiments, a motor unit housing includes two or three longitudinal faces where intersections between the faces are about perpendicular. In some embodiments, a face is shaped including protrusions and/or indentations and/or curves, e.g. in FIGS. 9A-9B undersides of the motor unit housings have a step shaped cross section.

In some embodiments, a motor unit housing has a shape where one or more intersection between longitudinal face planes is at a non-perpendicular angle. Potential benefits include the ability to position an arm closer to one or more longitudinal face of a motor unit housing and/or the ability to place a plurality of surgical arms extending from motor units close to each other. Referring to FIG. 15C, in some embodiments, a motor unit has a housing cross section 1520 as illustrated by dashed lines. An angle of intersection between a first 1522 and a second 1524 longitudinal face is more than 90°, for example, 90°-140°, or lower or higher or intermediate angles or ranges.

In some embodiments, one or more intersection between longitudinal face planes is less than 90°, or 20°-89°, or 30°-80°, or lower or higher or intermediate angles or ranges.

In some embodiments, a number of arms to be inserted into a single port is selected, then a motor unit and/or motor unit housing is selected, where an intersection between longitudinal faces is related to the number of housings to be connected, for example, where, in come embodiments, the angle is 360° divided by the number of motor units.

Figure 15E:
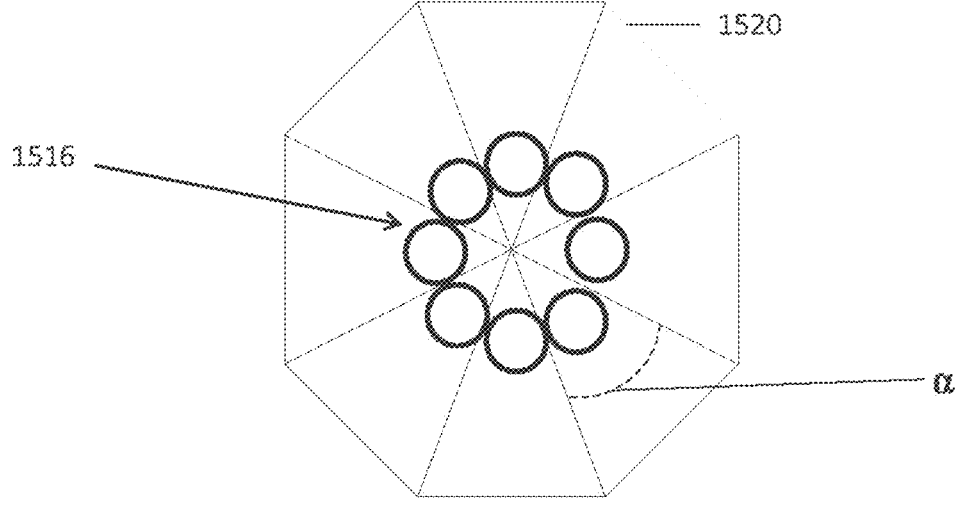

FIG. 15E illustrates a cross section of a motor construct including eight motor units and associated arm gears 1516 (motor gears not illustrated) where an angle α between longitudinal faces of the motor unit housings is about 360/8=45°.

Figure 16A:
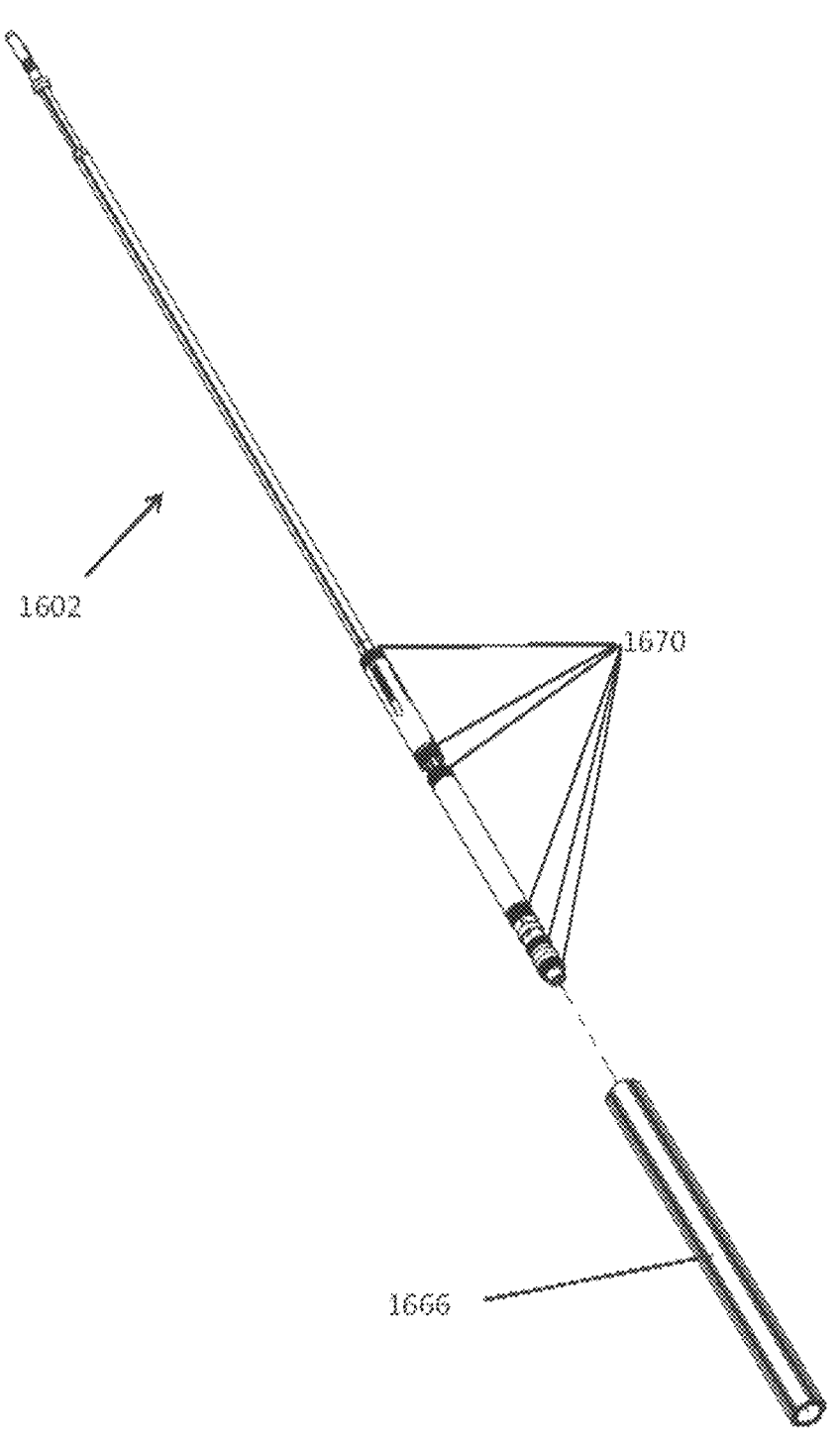
FIG. 16A is a simplified schematic of a surgical arm including surgical arm gears and a housing of a motor unit, according to some embodiments of the invention.

FIG. 16A is a simplified schematic of a surgical arm 1602 including surgical arm gears 1670 and a housing of a motor unit 1666, according to some embodiments of the invention. Gears of the motor unit are not illustrated.

Figure 16B:
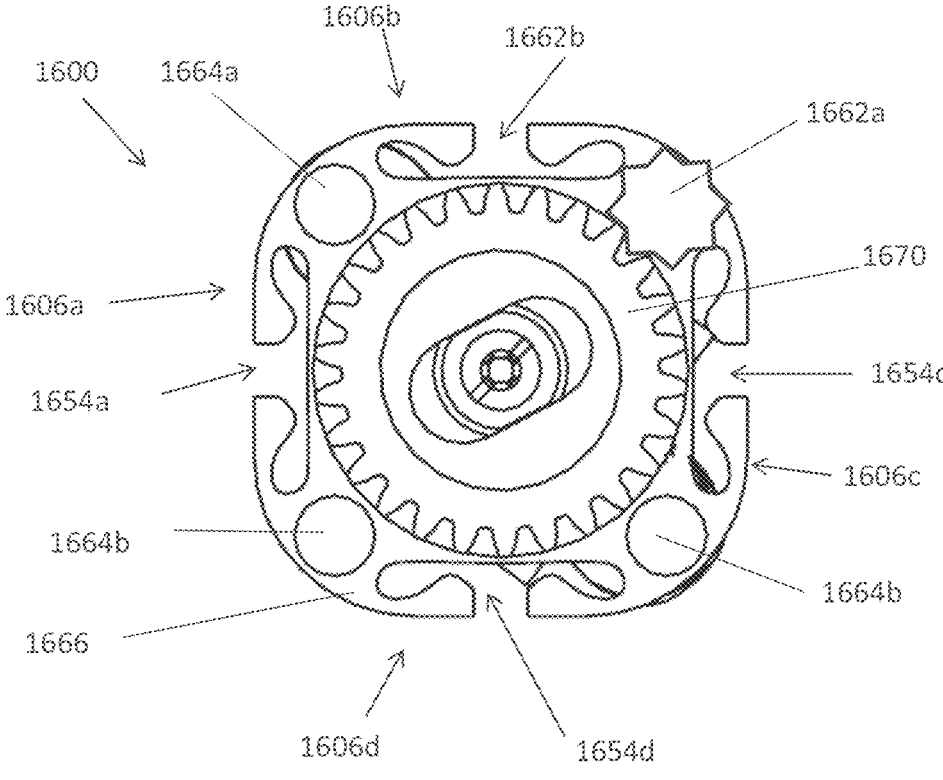
FIG. 16B is a simplified schematic top view of a motor unit where a motor unit housing includes a plurality of anchors, according to some embodiments of the invention.

FIG. 16B is a simplified schematic top view of a motor unit 1600 where a motor unit housing 1666 includes a plurality of anchors 1654a-d, according to some embodiments of the invention.

In some embodiments, a motor unit housing has more than one anchor 1654a-d. In some embodiments a motor unit housing has an anchor on more than one longitudinal face, for example, on each longitudinal face e.g. as illustrated in FIG. 16B where each of four longitudinal faces 1606a-d includes an anchor.

In some embodiments, anchors include indentation/s and/or protrusion/s configured to (e.g. sized and/or shaped to) connect with another anchor for example located on another motor unit housing. In some embodiments, anchors include indentation/s and/or protrusion/s configured to connect with a connector.

In some embodiments, a motor unit connector is configured for attachment (e.g. slide attachment) to more than one motor unit housing, for example, 2, 3, 4, 6 or larger or intermediate numbers of motor housings.

In some embodiments, a motor unit housing has rotational symmetry, for example, about a central long axis of the motor unit housing.

Figure 17:
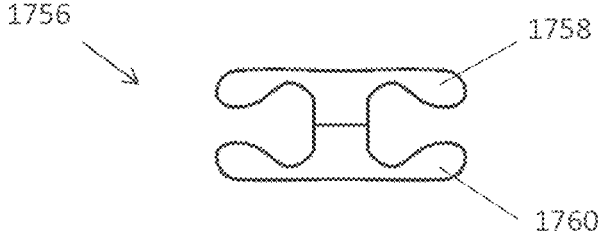
FIG. 17 is a simplified schematic top view of a motor unit connector, according to some embodiments of the invention.

In an exemplary embodiment, a single connector is configured to connect two motor unit housings. FIG. 17 is a simplified schematic top view of a motor unit connector 1756, according to some embodiments of the invention. In some embodiments, connector 1756 is configured to connect two motor housings, for example, two of housing 1666 illustrated in FIG. 16B. In some embodiments, connector 1756 connects two housings of different size and/or geometry. In some embodiments, connector 1756 connects a motor unit housing to another component, for example, a support (e.g. support 282 FIG. 2A, support 382 FIG. 3A).

In some embodiments, a connector has symmetrical cross section with at least one axis of symmetry. A potential benefit of symmetrical cross section connectors and/or anchors is the ability to use a single connector to connect any two anchors. A further potential benefit is ease of connection where a connection does not involve matching a particular side of a connector to each anchor. In some embodiments, a connector, when connecting a plurality of anchors, has an axis (or axes if the plurality is more than two anchors) of symmetry at the connection axis (or axes). For example, connector 1756 has a cross section with two axes of symmetry.

In some embodiments, a connector has a shape including curved portions 1758, 1760. A potential benefit of a curved connector is increased surface area between the connector and the anchor, potentially increasing the strength of friction between the anchor and the connector.

Figure 18:
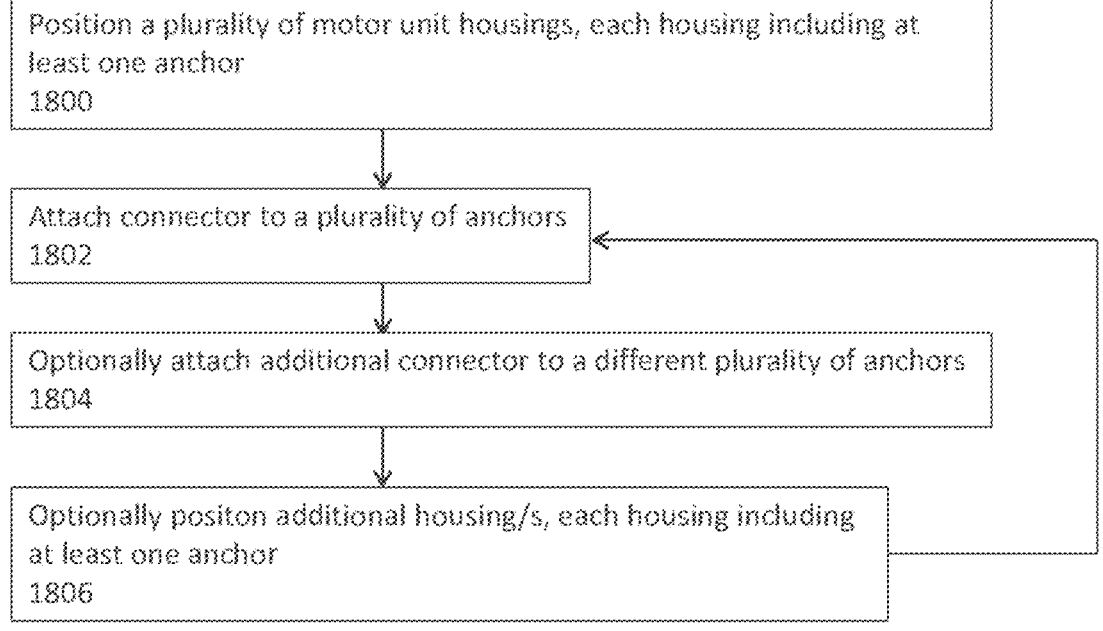
FIG. 18 is a flow chart of a method of connecting a plurality of motor unit housings, according to some embodiments of the invention.

FIG. 18 is a flow chart of a method of connecting a plurality of motor unit housings, according to some embodiments of the invention.

At 1800 a plurality of motor unit housings, each housing having at least one anchor, are positioned such that at least two anchors, each anchor on a different housing are facing each other. Although description of this method (and the method of FIG. 19 and in other parts of this document) is with respect to motor unit housings, it is to be understood that this method (and/or connection of motor units as described elsewhere in the document) also refers to interconnection of one or more motor unit with one or more other component including an anchor where the component is not necessarily a motor unit housing. For example, in some embodiments, a connector connects a motor unit housing to another component, for example, a support (e.g. support 282 FIG. 2A, support 382 FIG. 3A).

At 1802, a connector is, for example, inserted, connecting two or more housings. For example, in some embodiments, connector 1756 connects two housings by slide attachment, for example, in some embodiments, the motor housings are placed and/or held together such that two anchors, one on each housing are adjacent such that connector 1756 is slid into the hollow formed by the two anchors.

At 1804, optionally, in some embodiments, an additional connector is attached to and/or inserted into a plurality of housings. For example, referring to FIG. 20B, in some embodiments, all four motor units 2004a-d are positioned together and then connectors 2056a-d are inserted.

At 1806, optionally, in some embodiments, additional housing/s are positioned and then, optionally, at 1802 an additional connector is attached.

Figure 19:
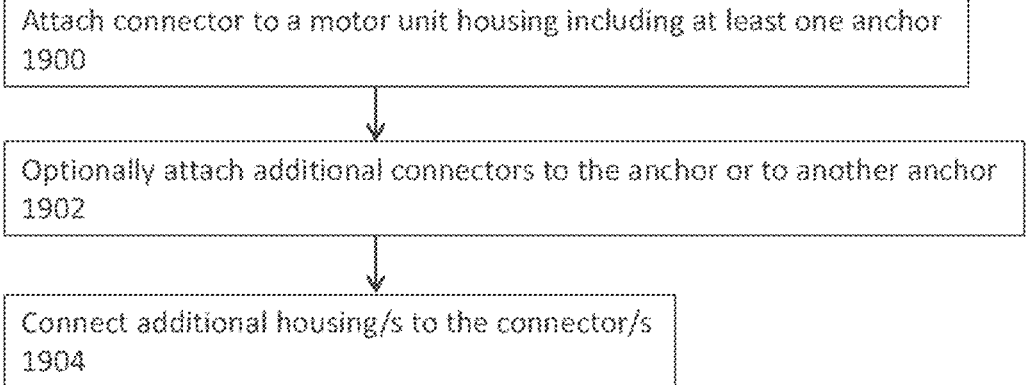
FIG. 19 is a flowchart of a method of connecting a plurality of motor unit housings, according to some embodiments of the invention.

FIG. 19 is a flowchart of a method of connecting a plurality of motor unit housings, according to some embodiments of the invention.

At 1900, in some embodiments, a connector is attached (e.g. slid into) a first anchor on a first motor unit.

At 1902, optionally, in some embodiments, additional connector/s are attached to the first anchor and/or to different anchor/s on the first motor unit.

At 1904, in some embodiments, a connector (while attached to the first motor unit) is attached (e.g. slid) into a second anchor on a second motor unit, or the anchor of the second motor unit is attached (e.g. slid) onto connector. Optionally, in some embodiments, additional motor units, for example, a third motor unit, are attached.

Figure 20A:
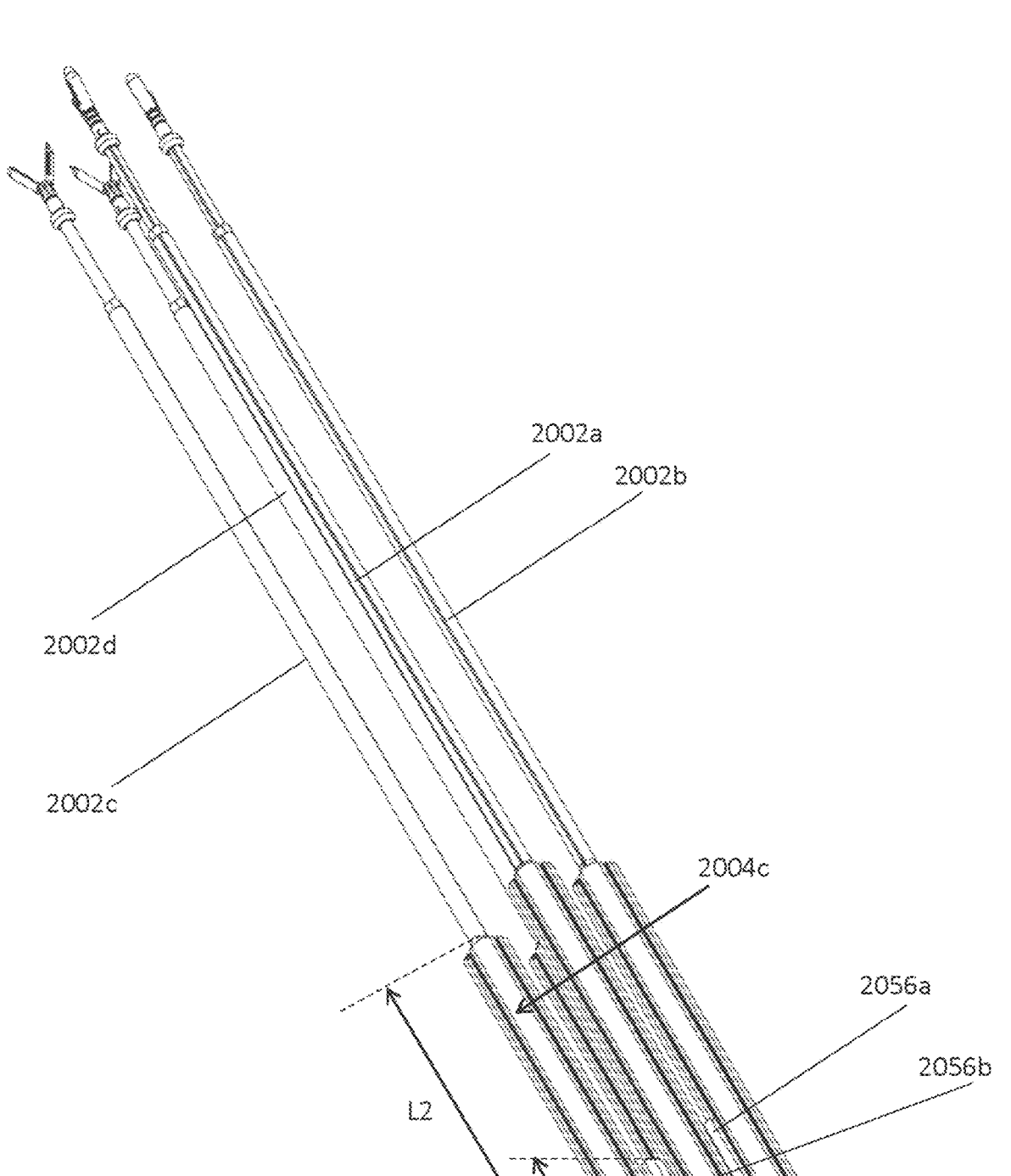
FIG. 20A is a simplified schematic exploded view of a plurality of motor units, associated surgical arms and a plurality of connectors prior to connection, according to some embodiments of the invention.

FIG. 20A is a simplified schematic of a plurality of motor units 2004a-d, associated surgical arms 2002a-d and a plurality of connectors 2056a-d prior to connection, according to some embodiments of the invention.

In FIG. 20A length of connectors 2056a-d, e.g. with respect to length of motor units 2004a-c is visible. In some embodiments, connectors and/or anchors have constant cross section (where cross section is taken perpendicularly to a long axis of the connector). For example, connectors 2056a-d in FIG. 20A have constant cross section.

Alternatively, in some embodiments, a connector and/or anchor has varying cross section. For example, in some embodiments, a connector tapers along a long axis length. For example, in some embodiments, a connector has one or protrusion and/or hollow along a long axis length (e.g. the protrusion and/or hollow providing an interference fit with an anchor e.g. the hollow providing an anchor for an anchor locking element e.g. spring loaded locking element). In some embodiments, a plurality of connectors connecting a plurality of motor housings has different shape and/or dimensions.

In some embodiments, motor housings and connectors have different long axis lengths. For example, referring to FIG. 20A, in some embodiments, a connector 2056 has a length L1 which is shorter than a length of one or more of the motor housing/s which the connector connects e.g. L1<L2 where L2 is a length of the motor housing of motor unit 2004c. For example, in some embodiments, a connector is short in length with respect to housings (e.g. with a long axis length of less than 70% or less than 50%, or less than 30% or less than 20% or less than 10% or less than 5% or 1-50%, or 1-20% or higher or lower or intermediate percentages of a length of a motor unit housing to which the connector is connected). Alternatively, in some embodiments, one or more connector is longer than one or more housing.

In some embodiments, a plurality of connectors connect a first anchor on a first housing and a second anchor on a second housing. For example, in some embodiments, a plurality of connectors are used when connectors are small in size and/or length with respect to a housing and/or housing weights.

In some embodiments, one or more connector is, for example, a snap-fit connector, a snap fastener.

In some embodiments, a connector surrounds at least a portion of one or more motor unit. For example, in some embodiments, a connector is a jacket or sleeve sized and/or shaped to accept and hold together in close proximity two or more motor units.

In some embodiments, a connector sleeve is made of rigid material. In some embodiments, a connector sleeve is made of flexible material optionally incorporating rigid element/s.

In some embodiments, use of a particular connector is used to provide information as to an arrangement of motor units. For example, in some embodiments, one or more connector includes a sensor (e.g. electromagnetic lock) which detects proximity of motor unit/s, the sensor providing information as to the spatial arrangement of motor units and/or surgical arms to the surgical system (e.g. to a processor). In some embodiments, use of a sleeve connector, for example, a rigid sleeve connector, means that a spatial arrangement of the motors is defined by the sleeve. For example, in some embodiments, a user selects a motor unit configuration and/or a suitable sleeve connector and enters this information and/or selects a matching model at a user interface.

Figure 30:
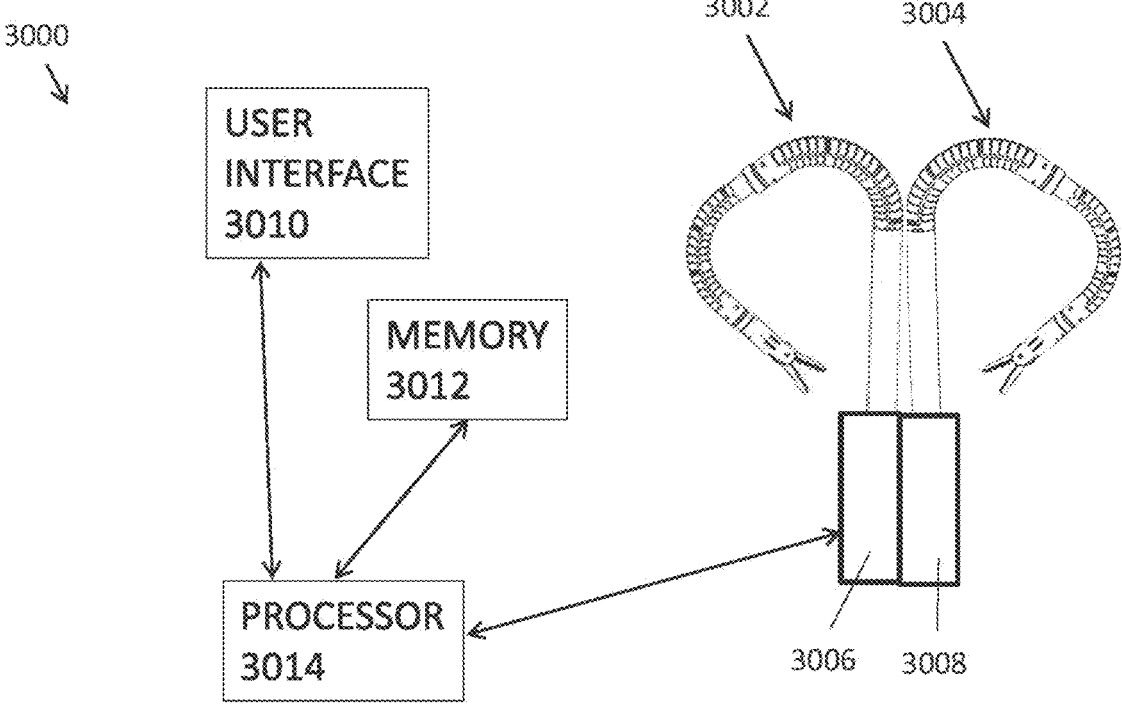
FIG. 30 is a simplified schematic of a surgical system, according to some embodiments of the invention.

FIG. 30 is a simplified schematic of a surgical system 3000, according to some embodiments of the invention. In some embodiments, system 3000 includes a plurality of modular units, each modular unit including a surgical arms 3002, 3004 configured to be attached to a motor unit 3006, 3008. In some embodiments, a memory 3012 stores one or more model of a configuration of attachment of modular units. In some embodiments, a user selects the model, for example, through a user interface 3010. Where, for example, a processor 3014 receives a user selection from user interface 3010, sending it for storage in memory 3012.

Alternatively or additionally, in some embodiments, one or more sensor, for example, located on a motor unit and/or surgical arm, sends a signal related to an attachment configuration to processor 3014 which is then sent by processor 3014 to be stored in memory 3012. It is to be understood that, in some embodiments, the system includes more than one user interface and/or more than one processor and/or more than one memory.

In some embodiments, processor 3014 uses the model and/or a controller uses the model in generation of control signals, which, for example, control movement of surgical arms 3002, 3004. For example, using the model to prevent collision of surgical arms during movement of the surgical arms.

In some embodiments, a memory stores information related to recommended configurations of modular units associated with different procedures. For example, in some embodiments, memory 3012 includes a look-up table of recommended modular unit configuration with surgical procedure, and/or with features of a surgical procedure (e.g. number of ports, position of ports, type of port).

Figure 20B:
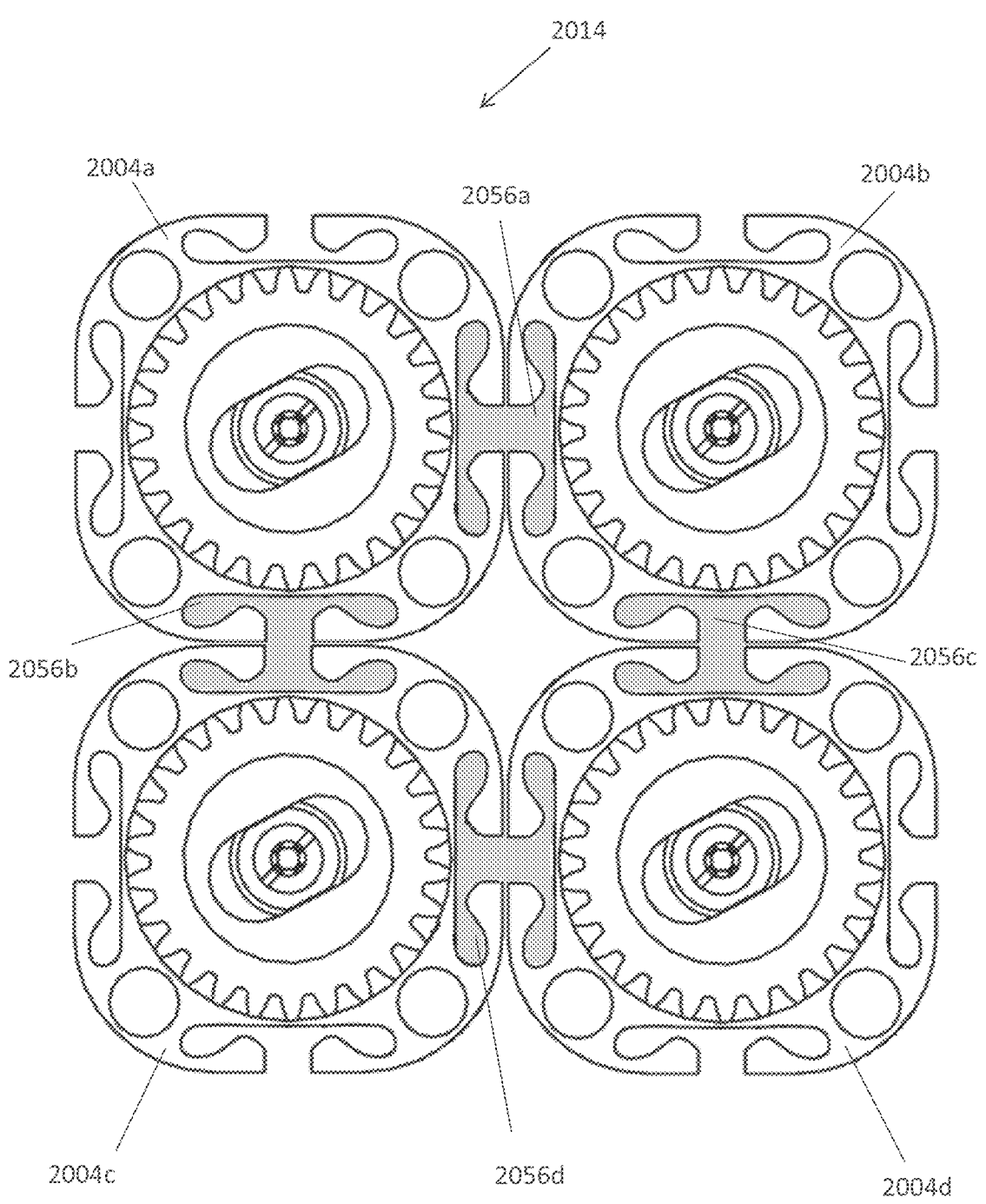
FIG. 20B is a simplified schematic top view of a motor construct including a plurality of motor units connected by connectors in a square configuration, according to some embodiments of the invention.

FIG. 20B is a simplified schematic top view of a motor construct 2014 including a plurality of motor units 2004a-d connected by connectors 2056a in a square configuration, according to some embodiments of the invention. Motor gears of the motor units are not illustrated in FIG. 20B.

In some embodiments, FIG. 20B illustrates a top view of the motor units and connectors illustrated in FIG. 20A, after attachment of the motor units 2004a-d by connectors 2056a-d.

In some embodiments, a closely packed arrangement of motor units (e.g. spare, circular) is selected, for example, for insertion into a round incision and/or a linear incision stretched into a round entrance into a patient body. For example, in some embodiments, an aspect ratio of the cross section area of the motor unit construct is 1:1-1:4 or 1:1-1:2, or lower or higher or intermediate ranges or aspect ratios.

In some embodiments, an elongated arrangement of motor units is selected, for example, for insertion into an elongated incision (for example, through port 514 illustrated in FIG. 5B) and/or for a surgical path with a body which is narrow and/or elongated (e.g. to surgical arms passing through a space between adjacent ribs). In some embodiments, an aspect ratio of the cross section of the motor unit construct is 1:1.5-1:10, or 1:2-1:4, or lower or higher or intermediate ranges or aspect ratios.

Figure 21:
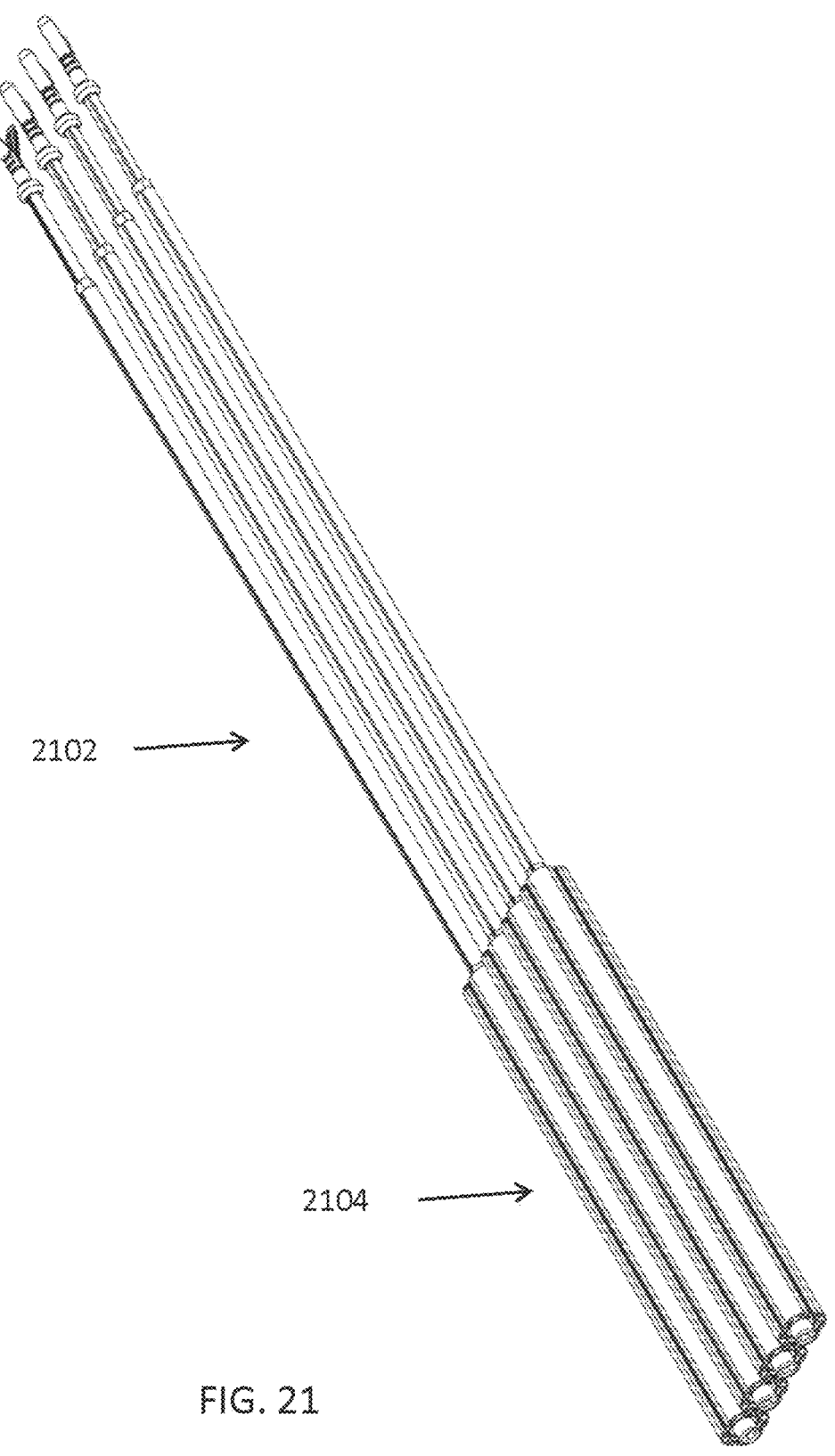
FIG. 21 is a simplified schematic of a plurality of motor units connected in an elongated configuration, according to some embodiments of the invention.

FIG. 21 is a simplified schematic of a plurality of motor units 2104 connected in an elongated configuration, according to some embodiments of the invention. In some embodiments, an elongated configuration includes a single row of attached motor units e.g. as illustrated in FIG. 21.

In some embodiments, selection of a spatial configuration of connected motor units includes selection of axial position of the motor units. In some embodiments, axial position motor units affects axial position of surgical arm/s and/or surgical arm tools. In some embodiments, axial position of surgical arm/s and/or arm tools is selected and then axial position of motor units is defined by this selection.

In some embodiments, motors units are attached to each other such that the motor units have different axial positons with respect to each other.

Figures 22A, 22B:
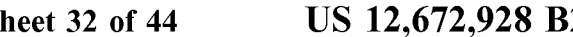
FIG. 22A is a simplified schematic of a plurality of connected motor units, and associated surgical arms, where one of the motor units has a different axial position, according to some embodiments of the invention.
FIG. 22B is an enlarged view of the portion of the motor units illustrated in FIG. 22A, according to some embodiments of the invention.

FIG. 22A is a simplified schematic of a plurality of connected motor units 2204a-d, and associated surgical arms, where one of the motor units has a different axial position, according to some embodiments of the invention.

FIG. 22B is an enlarged view of the portion of the motor units illustrated in FIG. 22A, according to some embodiments of the invention. FIG. 22B shows an enlarged view of the portion in FIG. 22A indicated by an "X".

In FIGS. 22A-22B motor unit 2204b is axially displaced with respect to motor units 2204a, 2204c, 2204d and, as a combined length of each surgical arm and motor unit is about equal, a maximum reach of a surgical arm 2202b associated with motor unit 2204b, when the arm is in a straight configuration, is larger than that of the other surgical arms associated with motor construct of attached motor units 2204a-d.

In some embodiments, more than one set of motor units (e.g. motor construct) each having a different surgical approach is used. For example, for a single procedure, more than one surgical approach is selected. In some embodiments, more than one surgical approach is implemented simultaneously. For example, where more than one of ports 512 illustrated in FIG. 5B are used. Alternatively, or additionally, in some embodiments, more than one surgical approach is implemented sequentially.

Figure 23:
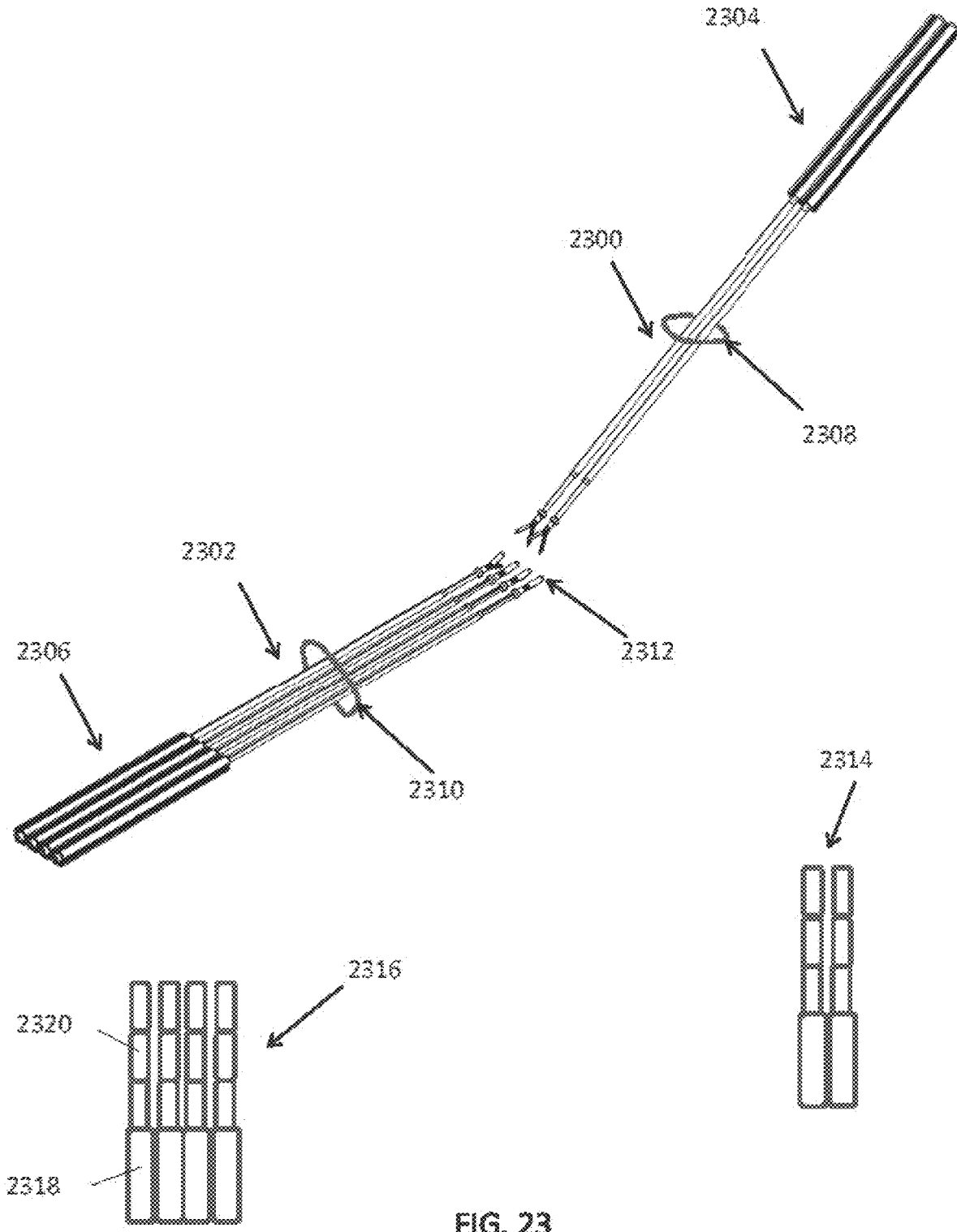
FIG. 23 is a simplified schematic of system including a first plurality of surgical arms inserted into a first port and a second plurality of surgical arms inserted into a second port, according to some embodiments of the invention.

FIG. 23 is a simplified schematic of system including a first plurality of surgical arms 2300 inserted into a first port 2308 and a second plurality of surgical arms inserted into a second port 2310, according to some embodiments of the invention. In some embodiments, the first plurality of surgical arms 2300 and the second plurality of surgical arms 2302 are associated with a first motor construct 2304 and a second motor construct 2306 respectively.

In some embodiments, both pluralities of arms access a surgical target area 2312, for example, through different ports and/or through different surgical paths.

Alternatively, in some embodiments, a first and a second plurality of coupled surgical arms are inserted through a single port. In some embodiments, a spatial configuration of each motor construct has been selected for compatibility with the respective associated surgical approach.

In some embodiments, each surgical modular unit including a surgical arm and an associated motor unit is controlled by a modular control unit. In some embodiments, a surgical system is configured such that there is a separate control unit for each modular unit. Alternatively, in some embodiments, a control unit is used to control more than one surgical modular unit. In some embodiments, control units are connected in a configuration matching that of connected modular units.

In some embodiments, first plurality of surgical arms 2300 is controlled by a first plurality of control modules 2314 and second plurality of surgical arms 2302 are controlled by a second plurality of control modules 2316.

In some embodiments, a single control module is used to control a single surgical arm. In some embodiments, more than one surgical arm is controlled by a single control module, for example, sequentially.

In some embodiments, a plurality of control modules are configured to interlock with each other, for example using mechanical means such as slide attachment, plunger lock, pins and/or other fasteners. In some embodiments, control modules interlock with each other using electromagnetic means. In some embodiments, interlocking between the control modules is released by a quick release mechanism, for example comprising a latch movable for releasing the lock. In some embodiments, one or more connector is used to connect two or more control modules, for example, a connector connecting two anchors one anchor located on each of two control module housings. In some embodiments, an anchor includes one or more indentation and/or protrusion. In an exemplary embodiment, an anchor is an indentation sized and shaped to receive a portion of a connector. In some embodiments, control modules are coupled by placing the control modules into a housing (e.g. a sleeve, a stand, a control console) which is configured to accept a plurality of control modules.

In some embodiments, the first and second plurality of surgical arms are controlled simultaneously, for example, by a single user e.g. in some embodiments, control modules 2314 and 2316 are both controlled by a single user. Alternatively, in some embodiments, the first and second plurality of surgical arms are controlled by more than one user. For example, in some embodiments, control modules 2314 are controlled by a first user and control modules 2316 are used by a second user.

In some embodiments, one or more control module (e.g. each control module) includes an input device arm 2320 coupled to a support 2318. In some embodiments, one or more control module support is configured to be coupled to another control module support.

In some embodiments, a surgical system is as described and/or includes control and/or input devices, for example, as described in US patent application which is incorporated herein by reference in its entirety.

In some embodiments, a surgical arm and an input device arm both include a sequential structure of connected portions where movement of one or more portion of the input device arm controls movement of a sequentially corresponding portion of the surgical arm. For example, in some embodiments, input device arm joints correspond to flexible portions of a surgical device e.g. each input device joint corresponds to a single flexible portion of a surgical device.

In some embodiments, a ratio between effective segment lengths of an input device segment pair (e.g. two adjacent input device segments) is substantially the same as an effective segment length ratio between a corresponding surgical device segment pair.

In some embodiments, each driven portion of the surgical device has a corresponding portion of the input device. In some embodiments, a surgical device arm and an input device arm both include segments coupled by connecting portions. In some embodiments, an input device arm includes at least the number of joints and/or segments as a corresponding articulated surgical device arm. In some embodiments, the input device and the surgical device include the same number of segments and/or the same number of connecting portions.

In some embodiments, one or more portion of an input device has the same degrees of freedom as that of a corresponding portion of a surgical device. For example, in some embodiments, input device portion/s are bendable by about the same amount as corresponding surgical device portions. For example, surgical device portion/s which are rotatable around the surgical device portion long axis correspond to input device portions which are rotatable around the input device portion long axis.

Potentially, similar structure of the input device arm and surgical device arm provides intuitive control of the surgical device.

In some embodiments, a sequential structure of the input device and/or the surgical device includes segments (e.g. rigid portions) connected by connecting portions (e.g. pivot joints and/or flexible sections). In some embodiments, an input device arm includes segments sequentially coupled by joints. In some embodiments, a surgical device arm includes sequentially coupled flexible portions, optionally coupled by surgical device segments. In some embodiments, freedom of movement of input device segments about joints is about the same as freedom of movement of corresponding surgical device flexible portions. For example, in some embodiments, a flexible surgical device portion is bendable by the same angle as an angle between two input device segments coupled by a joint corresponding to the flexible surgical device portion.

In some embodiments, an angle between long axes of input device segments coupled by a joint controls an angle of a corresponding surgical device flexible portion. Where, for example, an angle of the surgical device flexible portion is defined between long axis tangents of the flexible portion at the flexible portion ends. Where, for example, an angle of the surgical device flexible portion is defined as an angle between effective segment long axis (e.g. where effective segment axes are described herein).

In an exemplary embodiment, an input device includes a more angular shape and/or a shape with a larger relative lateral extent than that of the surgical device. For example, in an exemplary embodiment, input device connecting portions are pivot connections between rigid segments, whereas surgical device connecting portions are long bendable sections. In some embodiments, pivot points connecting sections of the input device are not disposed at an intersection between effective input device limbs for example, potentially reducing a difference between input device and surgical device structures.

In some embodiments, an angle between an input device radius and an input device humerus controls an angle between a surgical device radius and a surgical device humerus where a ratio between effective lengths of the input device radius and humerus is substantially the same as a ratio between effective lengths of the surgical device radius and humerus.

In some embodiments, a user manually moves portion/s of the input device to control movement of the surgical device. In some embodiments, a user controls position of more than one part of the device simultaneously, for example, using one hand. In some embodiments, the input device includes two limbs (also herein termed "arms"), and a user controls each limb with one hand.

In some embodiments, an angle between long axes of two adjacent input device segments controls an angle between long axes of two corresponding adjacent surgical device segments. In some embodiments, a rotation of one or more input device segment controls rotation of a corresponding surgical device segment.

Figure 24A:
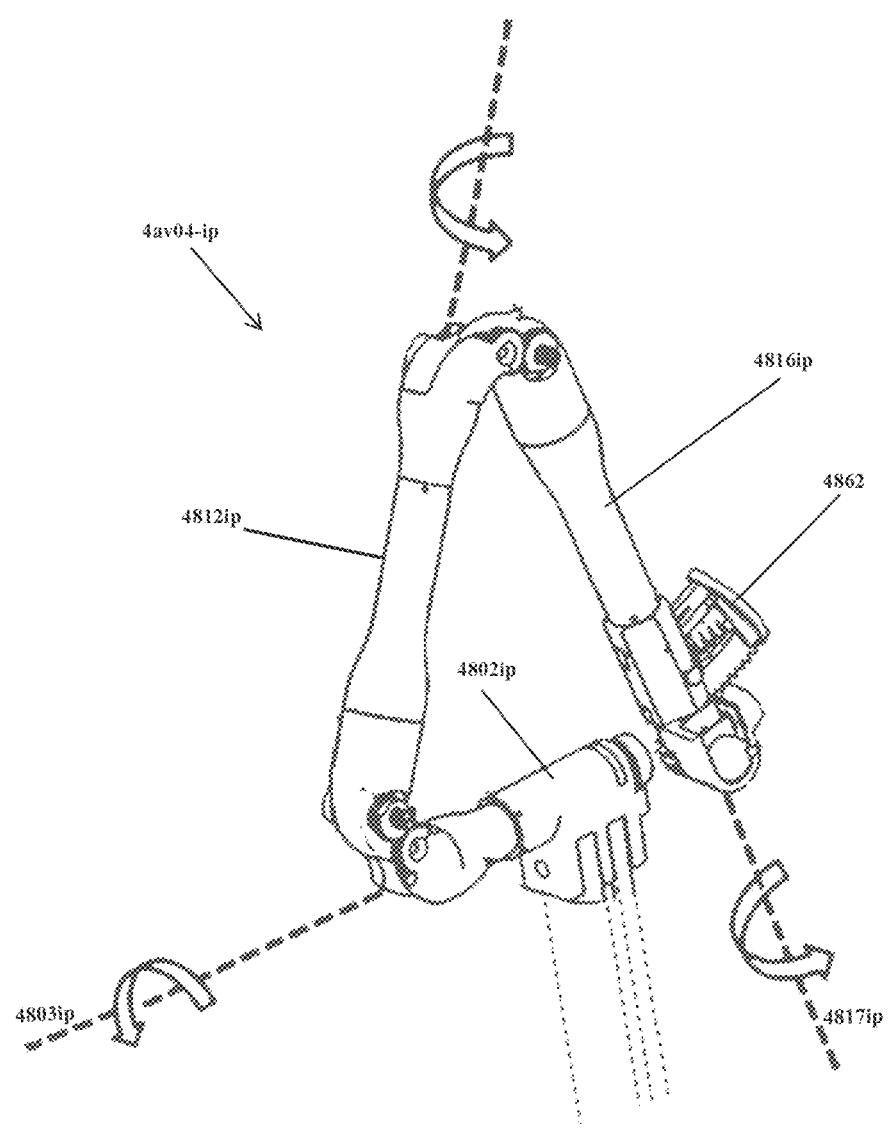
FIG. 24A is a simplified schematic side view of an input device arm, according to some embodiments of the invention.
Figures 24B, 24C:
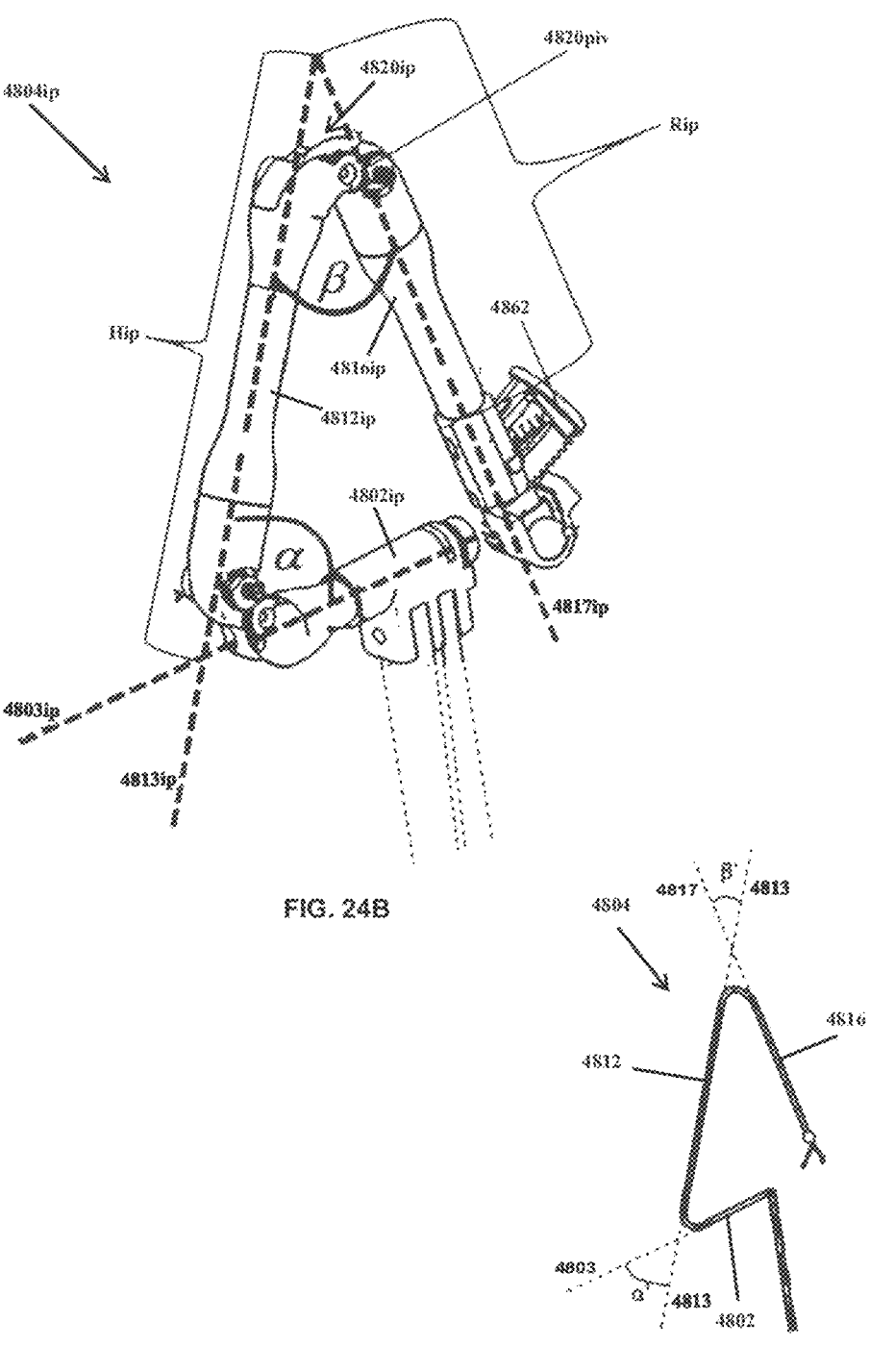
FIG. 24B is a simplified schematic side view of a surgical device arm, according to some embodiments of the invention.
FIG. 24C is a simplified schematic side view of an input device arm, according to some embodiments of the invention.

FIG. 24A is a simplified schematic side view of an input device arm 4804ip, according to some embodiments of the invention. FIG. 24B is a simplified schematic side view of a surgical device arm 4804, according to some embodiments of the invention. In some embodiments, input device arm 4804ip controls surgical device arm 4804.

In some embodiments, an input device structure has one or more ratio and/or dimension which is substantially the same as (also herein termed "matching") a ratio and/or dimension (optionally scaled) of a surgical device and, optionally, one or more other dimension and/or ratio which does not match those of a surgical device.

For example, in an exemplary embodiment, a length ratio between two effective segment lengths of an input device and a surgical device are substantially the same, for example, with 0-5%, or 0-1%, or 0-0.5%, or lower or higher or intermediate ranges or values of a difference between the ratios.

Where an effective segment length is the length of a central long axis of the segment between intersections of long axes of other segments and/or between an axis intersection and a termination of the segment.

For example, referring to FIG. 24A: An effective length of an input device arm 4800ip humerus 4812ip is length Hip, measured between intersections of humerus long axis 4813ip with the support (e.g. support long axis 4803ip) and radius long axis 4817ip. An effective length of an input device arm 4800ip radius 4816ip is length Rip, measured between intersection of radius long axis 4817ip and termination of input device radius 4816ip.

Potentially, an effective input device radius length corresponding to an effective surgical device radius length which does not include a length of an end effecter means that accuracy of control is maintained for surgical devices with different end effecters (e.g. different sized end effecters).

Figure 24D:
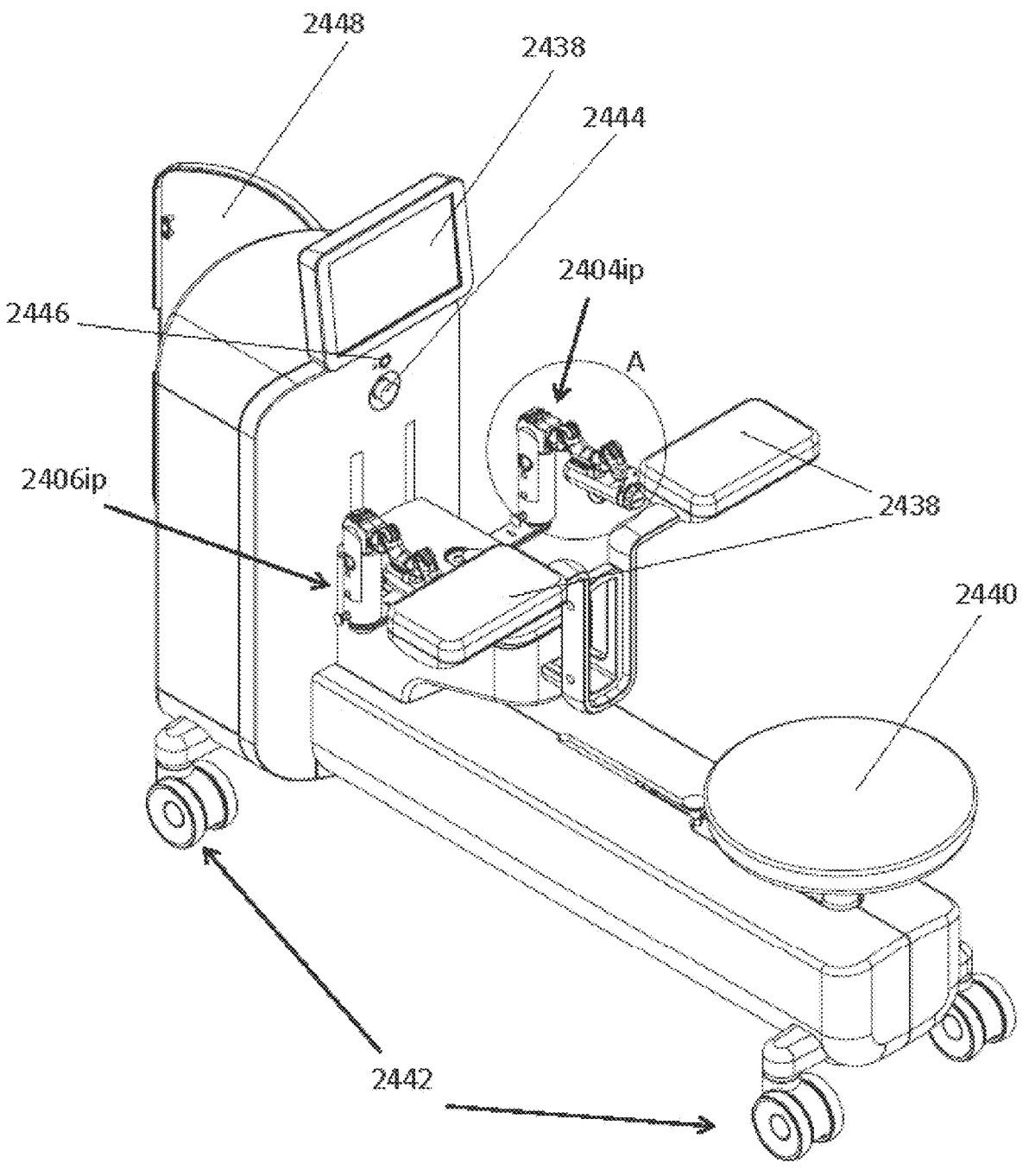
FIG. 24D is a simplified schematic side view of an input device arm, according to some embodiments of the invention.
Figure 24E:
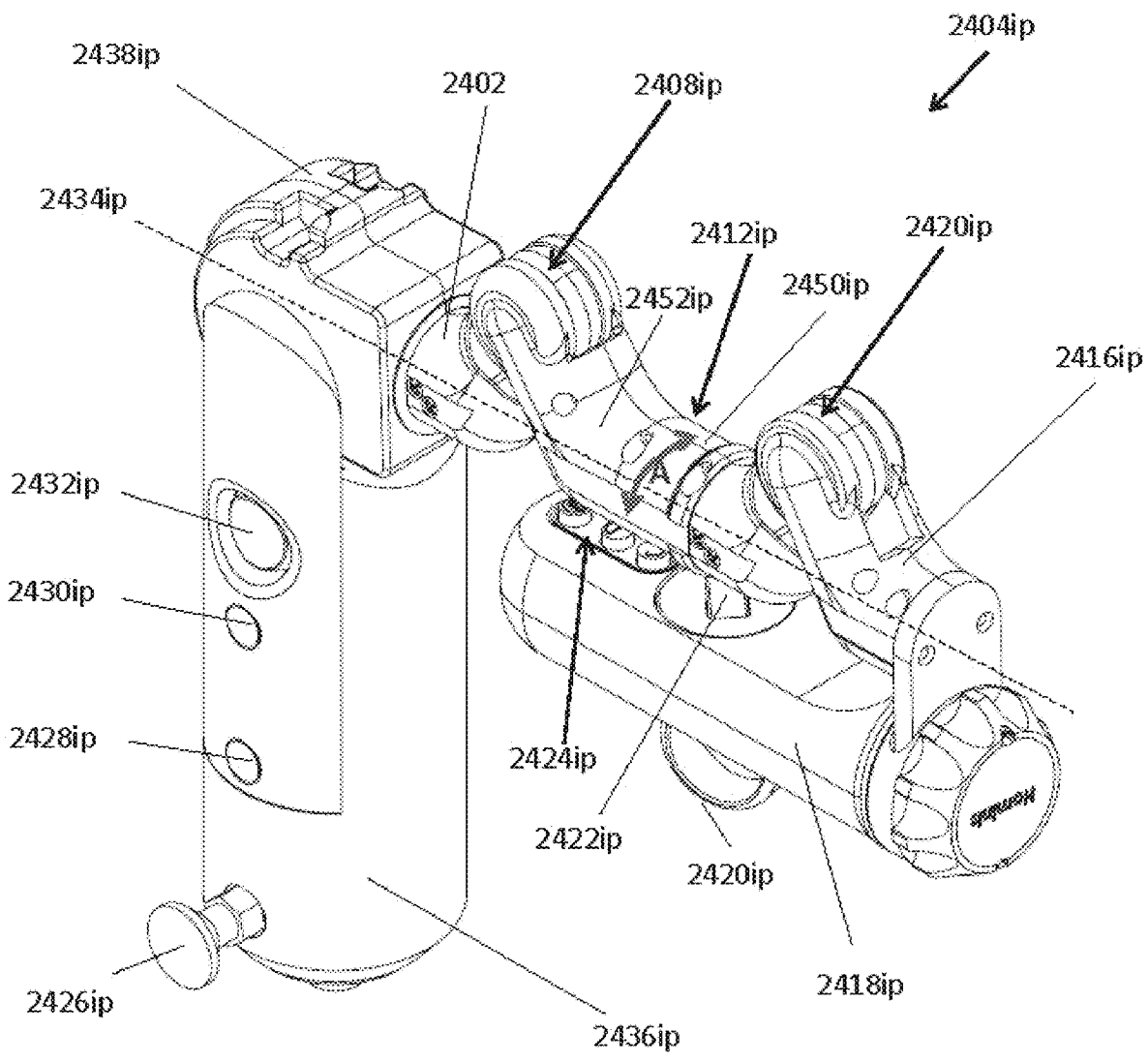
FIG. 24E is a simplified schematic side view of an input device arm, according to some embodiments of the invention.

In some embodiments, referring now to FIG. 24E, effective segments are straight lines connecting a center point of flexible portions (e.g. for surgical device arms) and/or joints (e.g. for input device arms). Where, for example, an effective radius of input device 2404ip is a straight line connecting pivot point of joint 2420ip to a distal end of radius 2416ip (distal end terminating in connection to handle 2418ip). Where, for example, an effective humerus of input device 2404ip is a straight line connecting centers of pivot joints 2408ip and 2420ip. Where, for example, referring to FIG. 1C, an effective surgical arm humerus is a line connecting a midpoint of flexible portion 108 to a midpoint of flexible portion 120 and an effective surgical arm radius is a line connecting a midpoint of flexible portion 120 to a distal end of radius 116.

In some embodiments, one or more matching segment length ratio between an input device and a surgical device enables intuitive control of the surgical device with the input device, for example, despite structural differences between the devices. For example in some embodiments, a surgical device (e.g. as described elsewhere in this document)

includes long connecting portions, whereas, in some embodiments, (e.g. as illustrated in FIG. 24A) input device arm joints include pivots.

In some embodiments, effective segment length ratios between the input device and surgical device match, but actual segment length ratios do not match. For example, in some embodiments, a surgical device includes long connecting portions (e.g. as described in the section of this document entitled "Exemplary long joints"), and an input device capable of controlling the surgical device includes short connecting portions for example, pivot connections (e.g. as illustrated in FIG. 24A). Potentially, an advantage being ease of control of the input device (e.g. input device segments rotate freely about pivots, e.g. input device segments do not move with unwanted degrees of freedom from long joints) and/or a surgical device which has an non-angular shape (e.g. less likely to damage patient tissue).

In an exemplary embodiment, a thickness of one or more input device segment (e.g. diameter of cylindrical segments and/or largest segment cross sectional dimension) is different (e.g. larger) than to those of a surgical device. Increased input device segment thickness potentially provides space for sensors and/or locking devices and/or provides an input device with dimensions which are comfortable and/or easy for a user to maneuver.

In an exemplary embodiment, input device segment thickness is 20-26 cm, or 13-18 cm, or 13-26 cm, or lower, or higher or intermediate ranges or thicknesses.

In an exemplary embodiment, surgical device segment thickness is 6-8 mm, or 4-8 mm, or 4-6 mm or lower, or higher or intermediate ranges or thicknesses. In some embodiments, surgical device segment thickness is 0.1-5 mm, 0.5-3 mm, or 0.1-1 mm, or lower or higher or intermediate ranges or thicknesses.

In an exemplary embodiment, a ratio between surgical device segment thickness and input device segment thickness is 1:0.5, to 1:3, or lower, or higher or intermediate ranges or ratios.

In an exemplary embodiment, a ratio between surgical device segment length and input device segment length is 1:0.5, to 1:3, or lower, or higher or intermediate ranges or ratios.

In some embodiments, a measured angle and/or change in angle between long axes of two input device segments, is used to control and/or change an angle between corresponding long axes of two surgical device segments.

In some embodiments, measurement is of a physical angle (e.g. angle $\alpha$) between long axes of two device segments and/or between effective segments (e.g. as described hereinabove). In some embodiments, measurement is of a change in angle between long axes of two device segments and/or between effective segments.

For example, in some embodiments, an angle $\alpha'$ between a long axis 4813 of a surgical device humerus 4812 and a long axis 4803 of a surgical device support 4802 is controlled by an angle $\alpha$ between a long axis 4813ip of an input device humerus 4812ip and a long axis 4803ip of an input device support 4802ip.

For example, in some embodiments, an angle $\beta'$ between a long axis 4817 of a surgical device radius 4816 and a long axis 4813 of a surgical device humerus 4812 is controlled by an angle $\beta$ between a long axis 4817ip of an input device radius 4816ip and a long axis 4813ip of an input device humerus 4812ip.

In an exemplary embodiment, a surgical device is controlled using a one-to-one mapping of an angle between adjacent input device segments and corresponding adjacent surgical device segments.

In some embodiments, rotation of an input device segment about a long axis of the segment is used to control rotation of a corresponding surgical device segment.

In some embodiments, measurement is of a physical angle of rotation. In some embodiments, measurement is of a change in angle of rotation.

FIG. 24D is a simplified schematic view of a control console, according to some embodiments of the invention. In some embodiments, a system including surgical arm/s and motor unit/s includes a control console for control of the surgical arms. In some embodiments, a user controls movement of surgical arms using a control console. In some embodiments, upon actions of a user, the control console sends signal/s (e.g. via processor/s) to instructing motor gears in motor unit/s. In some embodiments, a control console includes one or more input device arms. In an exemplary embodiments, the control console includes two input arms 2404$ip$, 2406$ip$. In some embodiments, two input arms are used to control one, two, or more than two surgical arms, for example, more than one surgical arm construct. Where, for example, a user selects surgical arms for control with the surgical arms, for example, then changing and/or switching the surgical arm selection.

In some embodiments, the control console includes a seat 2440 for a user to sit on and/or one or more arm support 2438. In some embodiments, position of seat 2440 and/or arm supports 2438 is adjustable. In some embodiments, the control console is mobile, for example, may be moved around (e.g. within an operating theatre). For example, in some embodiments, the control console is sized and/or shaped for ease of movement e.g. has less than 3×2 meter, or 2×1 meter, or lower or higher or intermediate ranges or areas footprint e.g. weighs less than 20-100 kg, or 60-80 kg, or about 72 kg or lower or higher or intermediate weights or ranges. In some embodiments, the control console includes one or more wheel 2442 mounted to a base of the control console and configured for wheeling the control console.

In some embodiments, the control console includes a display 2438, for example, for display of imaging during surgery (e.g. from a camera inserted with and/or mounted on surgical arm/s). Optionally, display 2438 is a touch screen and acts as a user interface. In some embodiments, the console includes additional user interface/s, for example, in some embodiments including an on/off switch and light indicator 2426 and and/or an emergency switch off button 2444, and/or user interface/s on the input arm/s 2404$ip$, 2406$ip$.

FIG. 24E is a simplified schematic side view of an input device arm 2404$ip$, according to some embodiments of the invention. In some embodiments, input arm 2404$ip$ includes a support segment 2402, a first input joint (also termed input device shoulder joint) 2408$ip$, a first input segment (also termed input device humerus) 2412$ip$, a second input joint (also termed input device elbow joint) 2420$ip$ and a second input segment (also termed input device radius 2416$ip$). In some embodiments, joints 2408$ip$, 2420$ip$ are pivot joints, which, in some embodiments, are separably bendable.

In some embodiments, an orientation of segments with respect to each other is adjusted by rotation of a segment and/or by rotation of a portion of a segment with respect to another portion of a segment.

For example, in some embodiments, second portion 2450$ip$ of first input segment 2412$ip$ is rotatable above a first input segment long axis, where rotation is with respect to a first portion 2452$ip$. The rotation is, for example illustrated by the arrow A in FIG. 24E.

For example, in some embodiments, support segment 2402 is rotatably attached to an input arm support 2438$ip$. For example, in some embodiments, a handle 2418$ip$ is rotatable with respect to second segment 2416$ip$.

In some embodiments, input arm support 2438$ip$ is pivotally connected to a stand 2436$ip$, rotation of the arm about the pivot connection thereby allowing a user to change an orientation of input device arm 2404$ip$ with respect to stand 2436$ip$. In some embodiments, button 2432$ip$, controls the ability to pivotally rotate the arm about the pivot connection, for example, in some embodiments, pressing on the button enables rotation.

In some embodiments, a user grasps handle 2418$ip$, for example, inserting a finger (e.g. index finger) into loop 2420$ip$. In some embodiments, while grasping handle 2428$ip$, a user interacts with user interface/s mounted on handle 2428$ip$. For example, buttons 2424$ip$ and lever 2422$ip$.

In some embodiments, the input device user interface/s are used to control the surgical arm, e.g. actuation of an arm tool e.g. opening and/or closing of a gripper.

Alternatively or additionally, in some embodiments, input device user interface/s are used to control other portions of the system, for example, the display of the control console (e.g. display 2438 FIG. 24D).

In some embodiments, input device and/or control console user interfaces control linear movement of the surgical arm (e.g. into and/or out of a patient) and/or pausing and/or resuming of control of movement of the surgical arm by the input arm.

In an exemplary embodiment, a first of buttons 2424$ip$ controls forward linear movement, a second of buttons 2424$ip$ controls backwards linear movement and a third of buttons controls pausing and resuming of control of movement of the surgical arm by the input arm.

In some embodiments, lever 2422$ip$ controls a surgical arm tool, for example controls opening and/or closing of a grasper tool (e.g. 124 FIG. 1C).

In some embodiments, 2428$ip$ and 2430$ip$ are connectors (in an exemplary embodiment, connectors 2428$ip$, 2430$ip$ are bolts) which, when removed, provide access to connection of the input arm to stand 2436$ip$ e.g. for removal and/or replacement of the input arm from the stand.

In some embodiments, 2426$ip$ is an element which enables rotation of stand 2436$ip$ about a stand long axis, enabling a user to change the orientation of the input device arm with respect to the control console.

In some embodiments, one or more control module includes one or more sensor which is configured to detect whether the control module has been connected to one or more other control module and/or a coupling arrangement of control modules. In some embodiments, a sensor detects insertion and/or attachment of a control module onto a control console. In some embodiments, each a control module (e.g. each control module) includes a sensor which senses whether the control module is attached to another control module and/or an attachment configuration. In some embodiments, a control module sensor provides a signal including attachment information (e.g. if the control module is attached and/or an attachment configuration) to a processor, for example, a control processor e.g. located at a control console.

In some embodiments, a control console (e.g. providing location for attachment of a plurality of control modules)

includes sensor/s sensing attachment and/or an attachment configuration of control modules.

In some embodiments, a processor (e.g. located at a control console) receives attachment information of surgical motor modules. In some embodiments, one or more motor unit includes a sensor configured to detect whether the motor unit has been connected to one or more other motor units and/or an attachment configuration of the motor units.

In some embodiments, a motor unit includes a plurality of motor gears where each motor gear is coupled to a gear of an extension of a surgical arm, also herein termed "surgical arm gear" or "arm gear". Surgical arm gears include, for example, bending gears and/or rotation gears, e.g. as described with reference to FIG. 6B.

In some embodiments, an axis of arm gears is positioned adjacent to one or more longitudinal face of a motor unit, with motor gear/s positioned adjacent to the arm gears. A potential benefit being the ability to place the surgical arm close to the longitudinal face (e.g. enabling a plurality of arms to be placed closely together). In some embodiments, size and/or axial positioning of motor gear/s restricts a minimum size of the motor unit thereby, in some embodiments, meaning that, for surgical arms to have a small separation, motor units may only be connected to each other at particular longitudinal faces.

In some embodiments, motor gears surround the surgical arm gears. For example, referring to FIG. 16B, in some embodiments, housing 1666 includes four axial locations surrounding surgical arm gear 1670 and configured to accept motor gears: In the top view of FIG. 16B motor gear 1662a which drives surgical arm gear 1670 is visible in one of the locations, and housing 1666 includes a further three locations 1664a, 1664b and 1664c configured for housing motor gears positioned to drive surgical arm gear 1670 or other surgical arm gears which are not visible in FIG. 16B.

In some embodiments, a lateral distance between an arm and a longitudinal face of a motor unit to which the arm is coupled, e.g. distance 803 in FIG. 8B, is restricted by a size of gears of the surgical arm (e.g. bending and/or rotation gears) and/or a size and location of motor gears driving the gears of a surgical arm (gears e.g. as described in more detail with reference to FIG. 6B).

Figure 25:
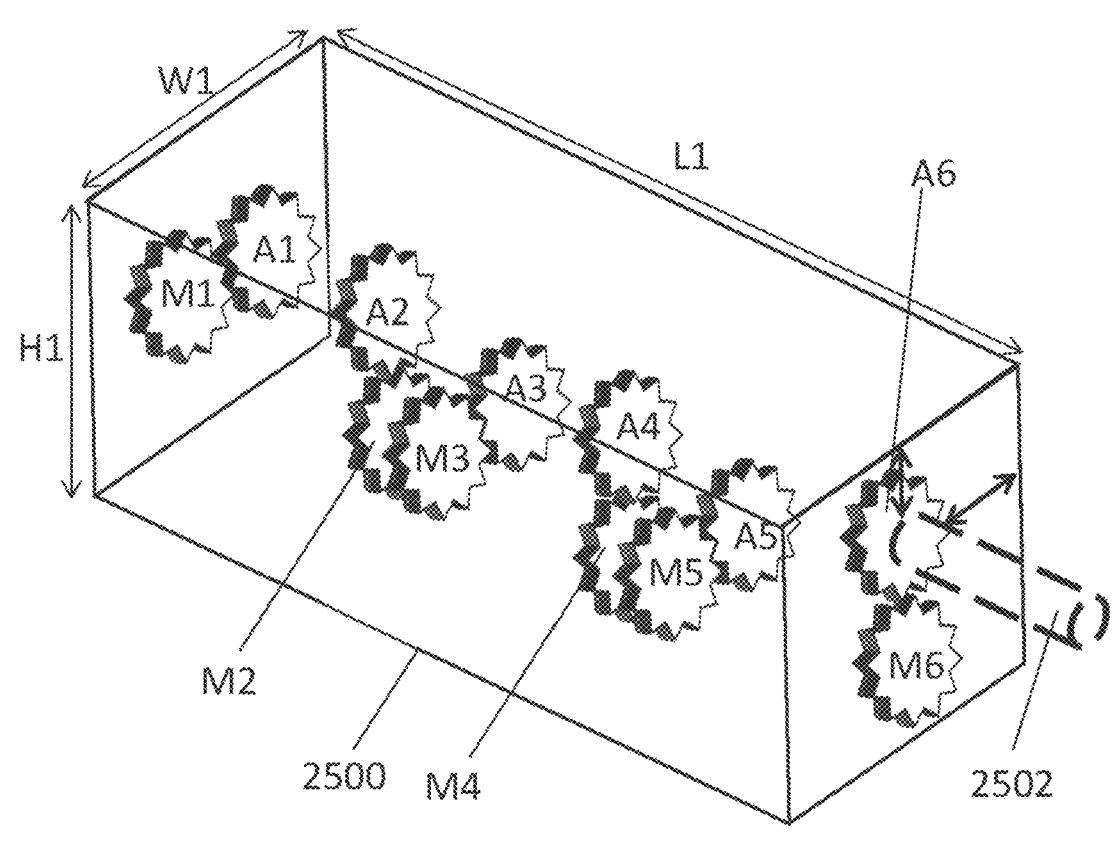
FIG. 25 is a simplified schematic of arm gears A1-6 and motor gears within a motor unit housing, according to some embodiments of the invention.
Figure 26:
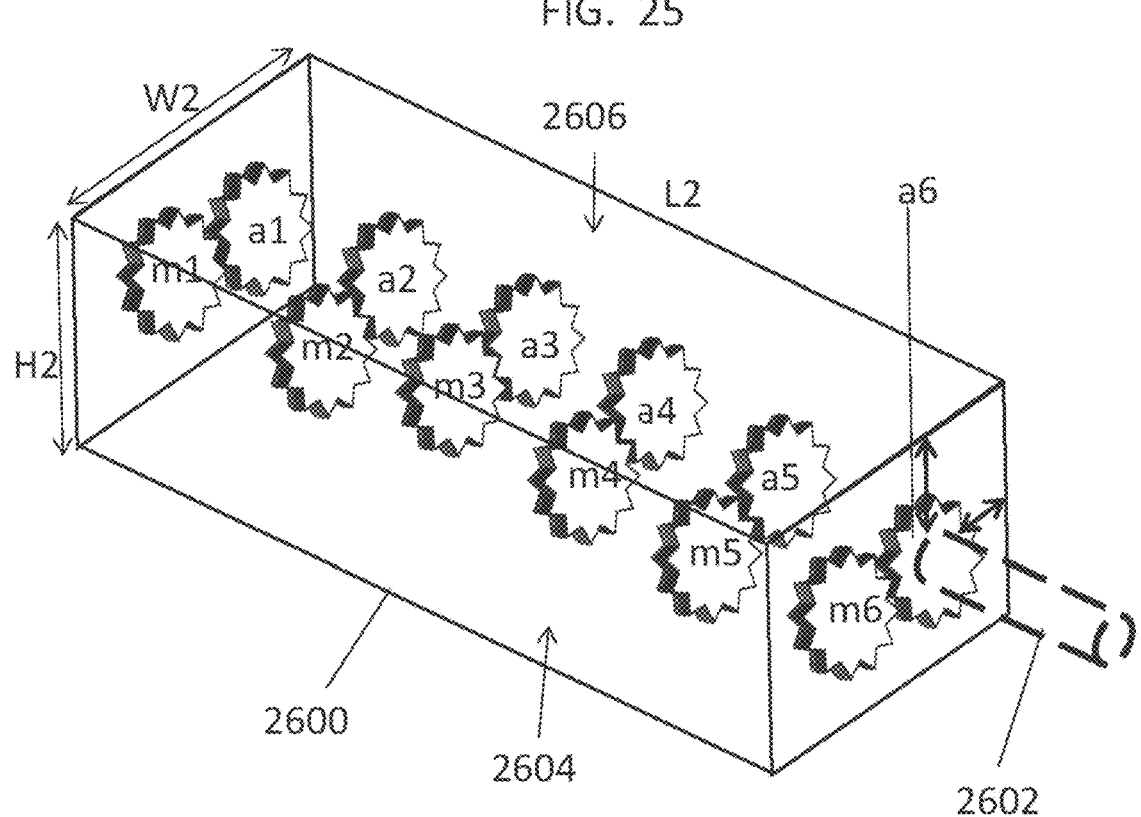
FIG. 26 is a simplified schematic of arm gears and motor gears within a motor unit housing, according to some embodiments of the invention.

In some embodiments, one or more surgical arm gear is smaller in diameter than a motor gear driving the surgical arm gear, e.g. as illustrated in FIGS. 15A-15D. A potential benefit being higher torque (e.g. than that of a gear with the same or smaller diameter as the surgical arm gear) of the driving gear on the surgical gear and/or a lower speed of rotation of the driving gear to effect a desired rotation speed of the surgical arm gear. In some embodiments, one or more motor gear has the same diameter (e.g. as illustrated in FIGS. 25-26) or smaller diameter as a surgical arm gear which it is driving.

In some embodiments, e.g. as illustrated by FIG. 16A, all surgical arm gears 1670 have about the same diameter. Alternatively, in some embodiments, one or more surgical arms gear has a different diameter. Similarly, in some embodiments, all motor gears have about the same diameter. Alternatively, in some embodiments, one or more motor gear has a different diameter.

In some embodiments, each arm gear is driven by a single motor gear.

Alternatively, in some embodiments, one or more arm gear is driven by more than one motor gear. For example, referring to FIG. 16B, where arm gear 1670 is driven by motor gear 1662a and an additional motor gear housed in one of gear locations 1664a-c. A potential advantage of driving an arm gear with more than one motor gear is the ability to achieve a certain torque with smaller gears.

In some embodiments, a motor unit includes motor gears with different axes. FIG. 25 is a simplified schematic of arm gears A1-6 and motor gears M1-6 within a motor unit housing 2500, according to some embodiments of the invention. In some embodiments, FIG. 25 illustrates the motor unit embodiment illustrated in FIG. 6B where motor gears M1, M3 and M5 are aligned axially and where motor gears M2, M4 and M6 are aligned axially in a different axial position and where surgical arm gears A1-6 are aligned axially. Where axial alignment is when central axes of the gears about which the gears rotate are collinear. An advantage of having motor gears in different axial positions is reduction of length L1 of the motor unit and/or separation between arm gears A1-6, when motors are collinear with the driving gears (e.g. as illustrated in FIG. 6B).

In some embodiments, a motor unit has motor gears where all of the gears have the same axis. FIG. 26 is a simplified schematic of arm gears a1-6 and motor gears m1-6 within a motor unit housing 2600, according to some embodiments of the invention. In some embodiments, all of the motor gears m1-6 are aligned axially meaning that, for example, in some embodiments, the gears are enclosed in a smaller height H2 motor unit housing 2600 e.g. H2<H1. A potential benefit being a smaller distance between an surgical arm 2602 and longitudinal faces 2604, 2606 of motor housing 2600.

Figure 27:
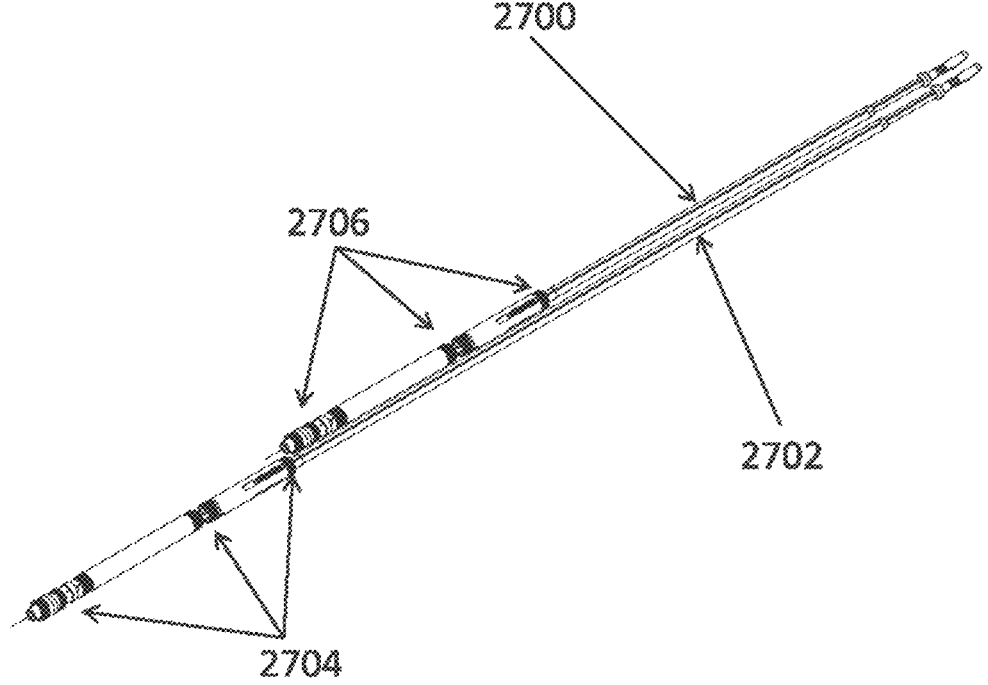
FIG. 27 is a simplified schematic of a first and a second surgical arm, each arm including surgical arm gears, according to some embodiments of the invention.

In some embodiments, size of motor units and/or surgical arm gears does not restrict a minimum separation between surgical arms. FIG. 27 is a simplified schematic of a first 2700 and a second 2702 surgical arm, the first arm including first surgical arm gears 2704 and the second arm including surgical arm gears 2706, according to some embodiments of the invention. In some embodiments, surgical arm gears are positioned at different axial position (e.g. axially staggered). A potential benefit being the ability to place the arms close together.

In some embodiments, a motor unit is miniaturized sufficiently that one or more motor unit is inserted through a port into a body. For example, in some embodiments, the motor unit housing and/or motor gears and/or surgical arm gears are sufficiently small for insertion into a body, e.g. through a port. In some embodiments, a motor unit has a cross section where at least one dimension and, in some embodiments, all dimensions are at most 100%, or 70% or 0-70% or 0-50% or 0-20% larger than a cross sectional dimension (e.g. diameter) of the surgical arm abutting the motor unit.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A surgical system comprising:
   a. at least one first motor unit configured for receiving and actuating movement of a first surgical arm;
   b. at least one second motor unit configured for receiving and actuating movement of a second surgical arm;
   wherein said surgical system is configured for assuming:
   i. a first operational spatial configuration in which the first motor unit and the second motor unit are coupled to one another; and
   ii. a second operational spatial configuration in which the first motor unit is detached from the second motor unit;
   wherein said first motor unit and said second motor unit are configured for surgical operation when attached and wherein the surgical arms are inserted into a body through a single port, and when detached and wherein the surgical arms are inserted into a body through two separate ports.

2. The surgical system according to claim 1, wherein in said first operational spatial configuration, said first motor unit and said second motor unit are configured for being operated together.

3. The surgical system according to claim 1, wherein, in said first operational spatial configuration, at least an operative portion of the surgical arms received in the first motor unit and second motor unit are configured for being received within a single port.

4. The surgical system according to claim 1, wherein, in said first operational spatial configuration, said first motor unit and said second motor unit are configured for being moved with respect to one another.

5. The surgical system according to claim 1, wherein said first operational spatial configuration is applicable for performing single port laparoscopic surgery.

6. The surgical system according to claim 1, wherein, in said second operational spatial configuration, said first motor unit and said second motor unit are configured for being operated separately and independently from each other.

7. The surgical system according to claim 1, wherein at least a portion of said first surgical arm is configured for being inserted through a first port, and a portion of said second surgical arm is configured for being inserted through a second port.

8. The surgical system according to claim 1, wherein said second operational spatial configuration is applicable for performing multi-port laparoscopic surgery.

9. The surgical system according to claim 1, wherein said system further comprises a controller configured for sending a control signal to a plurality of motor units to control movement of surgical arms.

10. The surgical system according to claim 9, wherein said controller includes at least one input device arm, configured for selectively controlling each of said at least one first motor unit and said at least one second motor unit.

11. The surgical system according to claim 9, wherein said controller includes two or more input device arms, each configured for controlling an individual motor unit.

* * * * *